US010300458B2

(12) United States Patent
Torii et al.

(10) Patent No.: US 10,300,458 B2
(45) Date of Patent: May 28, 2019

(54) WATER-ABSORBABLE RESIN POWDER, AND METHOD FOR DETERMINING ELASTIC MODULUS OF WATER-ABSORBABLE RESIN POWDER

(71) Applicant: NIPPON SHOKUBAI CO., LTD., Osaka-shi, Osaka (JP)

(72) Inventors: Kazushi Torii, Hyogo (JP); Ryosuke Fujikawa, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 15/514,784

(22) PCT Filed: Sep. 29, 2015

(86) PCT No.: PCT/JP2015/077577
§ 371 (c)(1),
(2) Date: Mar. 27, 2017

(87) PCT Pub. No.: WO2016/052537
PCT Pub. Date: Apr. 7, 2016

(65) Prior Publication Data
US 2017/0216817 A1    Aug. 3, 2017

(30) Foreign Application Priority Data

Sep. 29, 2014  (JP) .................................. 2014-199340
Sep. 29, 2014  (JP) .................................. 2014-199341

(51) Int. Cl.
*B01J 20/26*  (2006.01)
*A61L 15/60*  (2006.01)
(Continued)

(52) U.S. Cl.
CPC ............. *B01J 20/267* (2013.01); *A61L 15/24* (2013.01); *A61L 15/60* (2013.01);
(Continued)

(58) Field of Classification Search
None
See application file for complete search history.

(56) References Cited

U.S. PATENT DOCUMENTS 5,409,771 A   4/1995 Dahmen et al.
5,629,377 A   5/1997 Burgert et al.
(Continued)

FOREIGN PATENT DOCUMENTS

CA   2433044 A1   7/2002
CN   1140458 A    1/1997
(Continued)

OTHER PUBLICATIONS

Office Action dated Jan. 9, 2018 issued in Japanese Patent Application No. 2016-552082.
(Continued)

*Primary Examiner* — Alexandre F Ferre
(74) *Attorney, Agent, or Firm* — Harness, Dickey & Pierce, P.L.C.

(57) ABSTRACT

To provide water-absorbing resin powder particularly useful for a sanitary article, water-absorbing resin powder containing a polyacrylic acid (salt)-based water-absorbing resin as a main component is surface-crosslinked, and satisfies (1) to (3) below:

(1) a proportion of a water absorbent resin powder having a particle size of not less than 150 μm and less than 850 μm is not less than 90 weight %;
(2) a water absorption time according to a vortex method is not more than 42 seconds; and
(3) an elastic modulus index (600-500) is not less than 5500.

10 Claims, 9 Drawing Sheets

(51) Int. Cl.
*A61L 15/24* (2006.01)
*B01J 20/28* (2006.01)
*C08J 3/075* (2006.01)
*C08J 3/12* (2006.01)
*C08J 3/24* (2006.01)

(52) U.S. Cl.
CPC ... *B01J 20/28004* (2013.01); *B01J 20/28016* (2013.01); *C08J 3/075* (2013.01); *C08J 3/12* (2013.01); *C08J 3/245* (2013.01); *C08J 2333/02* (2013.01)

(56) References Cited

U.S. PATENT DOCUMENTS

| | | | |
|---|---|---|---|
| 5,985,944 | A | 11/1999 | Ishizaki et al. |
| 6,156,678 | A | 12/2000 | Mukaida et al. |
| 6,251,960 | B1 | 6/2001 | Ishizaki et al. |
| 6,453,960 | B1 | 9/2002 | Kondo et al. |
| 7,638,570 | B2 * | 12/2009 | Torii ............... A61L 15/60 502/400 |
| 2002/0128618 | A1 * | 9/2002 | Frenz ............... A61L 15/60 604/368 |
| 2006/0073969 | A1 | 4/2006 | Torii et al. |
| 2006/0204755 | A1 | 9/2006 | Torii et al. |
| 2010/0270501 | A1 * | 10/2010 | Torii ............... C08L 33/02 252/194 |
| 2011/0313113 | A1 | 12/2011 | Sakamoto et al. |
| 2012/0258851 | A1 | 10/2012 | Nakatsuru et al. |
| 2013/0026412 | A1 | 1/2013 | Machida et al. |
| 2014/0193641 | A1 | 7/2014 | Torii et al. |
| 2015/0210843 | A1 | 7/2015 | Kimura et al. |
| 2015/0216740 | A1 | 8/2015 | Watanabe et al. |
| 2016/0199529 | A1 | 7/2016 | Torii et al. |
| 2016/0207226 | A1 | 7/2016 | Torii et al. |

FOREIGN PATENT DOCUMENTS

| | | |
|---|---|---|
| CN | 1187371 A | 7/1998 |
| JP | 63-7203 B2 | 2/1988 |
| JP | 5-508425 A | 11/1993 |
| JP | 8-510484 A | 11/1996 |
| JP | 2000-309655 A | 11/2000 |
| JP | 2004-517173 A | 6/2004 |
| JP | 2008-142714 A | 6/2008 |
| WO | WO-2010095427 A1 | 8/2010 |
| WO | WO-2011078298 A1 | 6/2011 |
| WO | WO-2011126079 A1 | 10/2011 |
| WO | WO-2013002387 A1 | 1/2013 |
| WO | WO-2014038324 A1 | 3/2014 |
| WO | WO-2014041969 A1 | 3/2014 |
| WO | WO-2015030129 A1 | 3/2015 |
| WO | WO-2015030130 A1 | 3/2015 |

OTHER PUBLICATIONS

International Preliminary Report on Patentability dated Apr. 13, 2017 issued in International Patent Application No. PCT/JP2015/077577.

International Search Report and Written Opinion dated Dec. 28, 2015 issued in International Patent Application No. PCT/JP2015/077577.

Office Action for Chinese Application No. 201580052551.5 dated Dec. 6, 2018 (8 pages).

* cited by examiner

WATER-ABSORBABLE RESIN POWDER, AND METHOD FOR DETERMINING ELASTIC MODULUS OF WATER-ABSORBABLE RESIN POWDER

PRIORITY STATEMENT

This patent application is a U.S. national stage filing under 35 U.S.C. § 371 of International Application No. PCT/JP2015/077577, which has an international filing date of 29 Sep. 2015 and claims priority under 35 U.S.C. § 119 to JP 2014-199340 and JP 2014-199341, both filed on 29 Sep. 2014. The entire disclosure of each of the above applications is incorporated herein by reference.

TECHNICAL FIELD

The present invention relates to water-absorbing resin powder, more specifically to water-absorbing resin powder that exhibits a particularly excellent diffusion absorbency property. The present invention also relates to a method for measuring the elastic modulus of water-absorbing resin powder.

BACKGROUND ART

Water-absorbing resin (super absorbent polymer [SAP]) is a water-swellable, water-insoluble polymer gelling agent. Water-absorbing resin is heavily used mainly for disposable purposes, i.e., for absorbent articles such as a disposable diaper and a sanitary napkin and for an agricultural and horticultural water retaining agent, an industrial waterproofing agent, and the like. Of such water-absorbing resins, a polyacrylic acid (salt)-based water-absorbing resin, in which acrylic acid and a salt thereof are used as monomers or a combination of a polyacrylic acid-based water-absorbing resin and a polyacrylic acid salt-based water-absorbing resin, is particularly industrially most widely used from the viewpoint of its high water absorption performance.

Along with the advancement of the performance of a disposable diaper, which is a main application of use of the water-absorbing resin, the water-absorbing resin is required to have various functions (physical properties). Specific examples of the physical properties of the water-absorbing resin include not only merely a high fluid retention capacity but also a gel strength, a water-soluble component, a water absorption speed, a fluid retention capacity under pressure, a liquid permeability, a particle size distribution, a urine resistance, an antibacterial property, an impact resistance (damage resistance), a powder fluidity, a deodorizing property, an anti-coloring property (whiteness), a low dustiness, and the like.

Of the physical properties mentioned above, the liquid permeability is considered to be a more important physical property in view of an increase in the amount (for example, 50 weight % or more) of a water-absorbing resin used in a disposable diaper. Further, in addition to the liquid permeability, the water absorption speed is considered to be an important fundamental physical property for a water-absorbing resin. Under the circumstances, there have been studied techniques for improving the liquid permeability of, preferably both the liquid permeability and the water absorption speed of, a water-absorbing resin.

Patent Literature 1 studies a method for producing polyacrylic acid (salt)-based water-absorbing resin powder having both a higher liquid permeability and a higher water absorption speed. Specifically, Patent Literature 1 studies control of a gel-crushing step, a drying step, and a surface treatment step that are included in a process for producing polyacrylic acid (salt)-based water-absorbing resin powder.

Patent Literature 2 discloses a method including an air-bubble forming and containing step of decreasing the solubility of dissolved gas in an aqueous monomer solution in the presence of a surfactant and/or a dispersing agent to form air bubbles in the acrylic acid-based aqueous monomer solution so that the aqueous monomer solution contains the air bubbles. The method intends to provide white water-absorbing resin powder that is high in both liquid permeability (for example, SFC) and water absorption speed (for example, FSR).

Patent Literature 3 discloses a method including a step of polymerizing, in the absence of a surfactant or in the presence of not more than 300 ppm of a surfactant, an acrylic acid-based aqueous monomer solution containing gas dissolved and/or dispersed therein by a predetermined method. The method of Patent Literature 3 intends to highly efficiently produce a water-absorbing resin with a high water absorption speed without impairing the liquid absorbing property of a sanitary article or the like to be produced and without excessively decreasing the bulk specific gravity.

Patent Literature 4 discloses a method for producing water-absorbing resin particles that are excellent in absorption capacity and centrifugal absorption capacity under load through a step of mixing a chlorine- or bromine-containing oxidizing agent with a polymerization mixture for producing a crosslinked hydrogel or with a crosslinked hydrogel and a step of heat-treating (heating) the resulting mixture.

Patent Literature 5 discloses a method including copolymerizing a compound prepared by neutralizing acrylic acid or a methacrylic acid and a crosslinking agent having two or more polymerizable unsaturated groups, the copolymerizing including first adding a radical polymerization initiator in an amount of 0.0001 mol % to 0.1 mol % per the total amount of monomers, and then adding the radical polymerization initiator in an amount of 0.01 mol % to 5 mol % in total per the total amount of monomers in one or more portions for polymerization. The method intends to easily and inexpensively produce a hydrogel that is capable of absorbing a large amount of water rapidly and retaining the water and contains only a small amount of unreacted monomer.

CITATION LIST

Patent Literature

[Patent Literature 1] International Publication WO 2011-126079 (Publication Date: Oct. 13, 2011)
[Patent Literature 2] International Publication WO 2011-078298 (Publication Date: Jun. 30, 2011)
[Patent Literature 3] International Publication WO 2010-095427 (Publication Date: Aug. 26, 2010)
[Patent Literature 4] Japanese Translation of PCT International Application, Tokuhyohei, No. 8-510484 (Publication Date: Nov. 5, 1996)
[Patent Literature 5] Japanese Patent Publication, Tokukoushou, No. 63-7203 (Publication Date: Feb. 16, 1988)

SUMMARY OF INVENTION

Technical Problem

However, a water-absorbing resin is required to further improve in physical property. In particular, there is a demand for a water-absorbing resin that is more excellent in diffusion absorbency property in addition to improvements in liquid permeability that has been demanded. An improved diffusion absorbency property makes it possible to provide water-absorbing resin powder that is excellent in liquid absorption, has a low rewet when the resin having absorbed water is under load, and is especially useful for sanitary articles such as a disposable diaper, a sanitary napkin, and a blood absorbent for medical use. To this end, a method is described below for accurately determining the elastic modulus of water-absorbing resin powder.

Solution to Problem

In order to attain the above object, the inventors of the present invention have conducted diligent research and have thus discovered that more precisely controlling the shape of particles of a water-absorbing resin powder dramatically improves the physical properties of the water-absorbing resin.

The inventors have thereby discovered that a water-absorbing resin powder that is highly elastic and has a high water absorption speed exhibits an excellent diffusion absorbency property. The inventors have further discovered that a particularly excellent diffusion absorbency property is exhibited by water-absorbing resin powder of which the "elastic modulus index" (which is derived from correcting the value of the elasticity on the basis of a theoretical surface area and fluid retention capacity without pressure of particles of swollen gel prepared by swelling a water-absorbing resin powder) and the water absorption time according to a vortex method each satisfy a predetermined requirement. The inventors have consequently completed the present invention. Specifically, the present invention covers the following aspects:

[1-1] Water absorbent resin powder, including: a polyacrylic acid (salt)-based water-absorbing resin as a main component, the water absorbent resin powder being surface-crosslinked and satisfying (1) to (3) below:

(1) a proportion of a water absorbent resin powder having a particle size of not less than 150 μm and less than 850 μm is not less than 90 weight %;

(2) a water absorption time according to a vortex method is not more than 42 seconds; and (3) an elastic modulus index (600-500) is not less than 5500.

The elastic modulus index cannot be calculated accurately unless the elastic modulus is determined accurately. In view of that, the inventors of the present invention have discovered a method for accurately determining an elastic modulus, thereby completing the present invention. Specifically, the present invention covers the following aspect:

[2-1] A method for measuring an elastic modulus of water-absorbing resin powder, the method including:

a classification step of classifying a water-absorbing resin powder (A) by using two or more sieves having different mesh sizes so as to obtain a water-absorbing resin powder (B);

a swelling step of swelling the water-absorbing resin powder (B) in a swelling liquid to obtain swollen gel;

a containing step of containing the swollen gel into a container section having a horizontal bottom surface;

a load imposing step of imposing a load perpendicularly to the swollen gel, which is held in the bottom surface that is in contact with the swollen gel, with a plate-shaped member that is parallel to the bottom surface, said load being discontinuously increased up to a target load of at least not less than 2.4 kPa; and a measurement step of measuring a storage elastic modulus under a predetermined load in the load imposing step, where at least a portion of the bottom surface and/or the plate-shaped member that comes in contact with the swollen gel is made of aluminum.

Advantageous Effects of Invention

A water-absorbing resin powder in accordance with the present invention exhibits a particularly excellent diffusion absorbency property. This yields an effect of providing sanitary materials such as a disposable diaper, a sanitary napkin, and a blood absorbent for medical use each having a more excellent physical property. Further, a method in accordance with the present invention for measuring the elastic modulus of the water-absorbing resin powder uses, as a measurement target, a water-absorbing resin powder having relatively well-adjusted particle sizes, and includes the steps of sandwiching swollen gel between members configured such that at least a portion thereof that comes in contact with the swollen gel is made of aluminum and imposing a load onto the swollen gel in a predetermined manner. This yields an effect of measuring an elastic modulus accurately.

Figure 1:
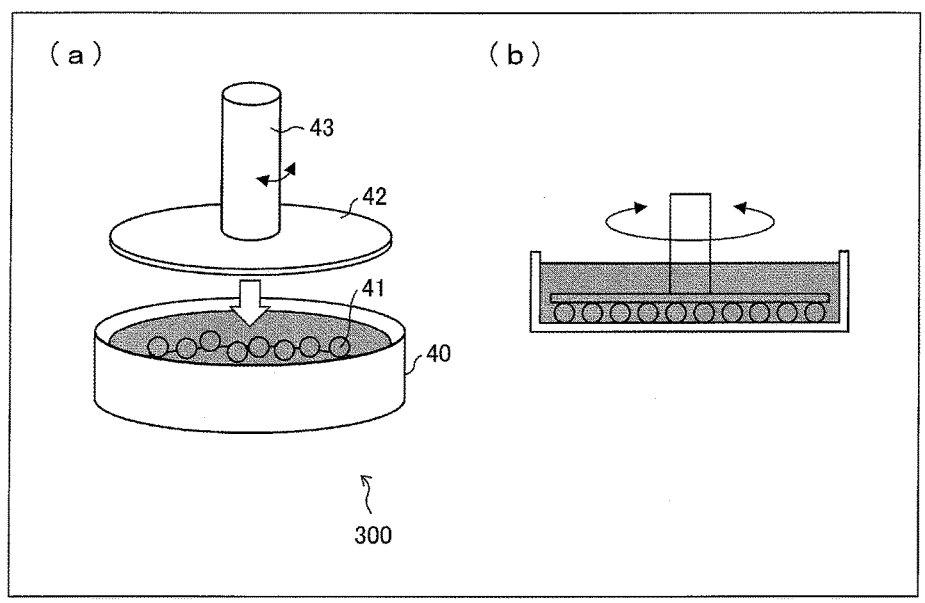
FIG. 1 shows diagrams each illustrating an appearance of an example device for use in measuring the elastic modulus of a water-absorbing resin powder.

produced in Examples and comparative water-absorbing resin powders (1) to (5) produced in Comparative Examples.

DESCRIPTION OF EMBODIMENTS

The following description will each discuss in detail a water-absorbing resin powder, a method for producing the water-absorbing resin powder, and a method for measuring the elastic modulus of a water-absorbing resin powder, in accordance with the present invention. The present invention is, however, not limited in scope to the description below, and may be altered from the examples below and practiced as appropriate as long as such alteration is not a departure from the scope of the present invention.

Specifically, the present invention should not be construed as being limited to the embodiments below, and may be modified in many ways within the scope of the claims below. The technical scope of the present invention may encompass any modifications obtainable by appropriately combining technical means disclosed in different embodiments.

[1] Definitions of Terms (1-1) "Water-Absorbing Resin"

The term "water-absorbing resin" as used for the present invention means a water-swellable, water-insoluble polymer gelling agent. The expression "water-swellable" means that CRC as defined in ERT 441.2-02 is not less than 5 g/g. The expression "water-insoluble" means that Ext as defined in ERT 470.2-02 is 0 weight % to 50 weight %.

The water-absorbing resin can be designed as appropriate according to its purpose of use, and is not limited to a particular design. The water-absorbing resin is preferably a hydrophilic crosslinked polymer that has been obtained by crosslinking and polymerizing unsaturated monomers each of which has a carboxyl group. Moreover, the water-absorbing resin is not limited to a form in which the water-absorbing resin is wholly (that is, 100 weight %) a polymer, and can be a water-absorbing resin that is surface-crosslinked or a water-absorbing resin composition that contains an additive and the like within a range in which the above-described performance is maintained.

The "water-absorbing resin" above is a resin obtained by turning the hydrophilic crosslinked polymer to powder form. For convenience, a water-absorbing resin that has not been surface-treated or surface-crosslinked is herein referred to as "water-absorbing resin particles", whereas a water-absorbing resin that has been surface-treated or surface-crosslinked is herein referred to as "water-absorbing resin powder". Further, either a water-absorbing resin that varies in form obtained in each step (examples of the form of the water-absorbing resin include a sheet form, a fiber form, a film form, a gel form, and the like) or a water-absorbing resin composition that contains an additive and the like is herein collectively referred to as "water-absorbing resin".

The "resin obtained by turning the hydrophilic crosslinked polymer to powder form" above may be a resin obtained by pulverizing the hydrophilic crosslinked polymer into powder form, or a resin that is in powder form without pulverization of the hydrophilic crosslinked polymer, such as the water-absorbing resin produced by reversed phase suspension polymerization.

(1-2) "Polyacrylic Acid (Salt)"

The term "polyacrylic acid (salt)" as used for the present invention means a polymer that has, if necessary, a graft component, and contains repeating units including acrylic acid, its salt, or a combination thereof as main components (the acrylic acid and the salt thereof are herein collectively referred to as "acrylic acid (salt)").

Specifically, the term "polyacrylic acid (salt)" according to the present invention is a polymer in which acrylic acid (salt) essentially accounts for 50 mol % to 100 mol % in the total monomer content (except an internal crosslinking agent) to be polymerized, preferably a polymer in which acrylic acid (salt) accounts for 70 mol % to 100 mol % in the total monomer content, more preferably a polymer in which acrylic acid (salt) accounts for 90 mol % to 100 mol % in the total monomer content, and even more preferably a polymer in which acrylic acid (salt) accounts for substantially 100 mol % in the total monomer content. Further, the polyacrylic acid (salt) which is used as a polymer essentially contains a water-soluble salt, and the water-soluble salt (neutralized salt) contains, as a main component, preferably a monovalent salt, more preferably an alkali metal salt or ammonium salt, even more preferably an alkali metal salt, and especially even more preferably a sodium salt.

(1-3) "EDANA" and "ERT"

The term "EDANA" is an acronym for the European Disposables and Nonwovens Associations. The term "ERT" is an acronym for EDANA Recommended Test Methods, which are European standard (de facto international standard) methods for measuring physical properties of water-absorbing resin. For the present application, unless otherwise noted, measurements are taken in accordance with the ERT (Known Literature: Revised in 2002).

(a) "CRC" (ERT 441.2-02)

The term "CRC" is an acronym for "centrifuge retention capacity", and refers to a fluid retention capacity without pressure (hereinafter referred to also as "fluid retention capacity"). Specifically, "CRC" is fluid retention capacity (unit; g/g) measured when 0.200 g of a water-absorbing resin in a nonwoven fabric bag is allowed to freely swell in a large excess of a 0.9 weight % aqueous sodium chloride solution for 30 minutes and then drained by a centrifugal separator. For the present invention, "CRC" is evaluated with use of a value calculated by correcting the weight of a water-absorbing resin on the basis of the moisture content.

(b) "AAP" (ERT 442.2-02)

The term "AAP" is an acronym for "absorption against pressure", and refers to a fluid retention capacity under pressure. Specifically, "AAP" refers to a fluid retention capacity (unit: g/g) measured after 0.9 g of a water-absorbing resin has been swollen in a large excess of a 0.9 weight % aqueous sodium chloride solution for 1 hour under a load of 2.06 kPa (0.3 psi). The present specification uses the expression "AAP 0.3". ERT 442.2-02 uses the term "Absorption Under Pressure", which refers to substantially the same thing as "AAP". For the present invention, "AAP" is evaluated on the basis of a value calculated by correcting the weight of a water-absorbing resin on the basis of the moisture content.

(c) "Ext" (ERT 470.2-02)

The term "Ext" is an abbreviation for "Extractables", and refers to a water-soluble component (water-soluble component amount) of a water-absorbing resin. Specifically, "Ext" refers to a dissolved polymer amount (unit; weight %) obtained by adding 1.0 g of a water-absorbing resin to 200 ml of a 0.9 weight % aqueous sodium chloride solution and stirring the resulting mixture at 500 rpm for 16 hours. An amount of the dissolved polymer is measured by pH titration.

(d) "PSD" (ERT 420.2-02)

The term "PSD" is an acronym for "particle size distribution", and refers to a particle size distribution of a water-absorbing resin that is measured by sieve classification. The weight average particle diameter (D50) and the logarithmic standard deviation (σζ) are measured according to a method similar to "(3) Mass-Average Particle Diameter (D50) and Logarithmic Standard Deviation (u) of Particle Diameter Distribution", which is a method disclosed in U.S. Pat. No. 7,638,570.

(e) "Moisture Content" (ERT 430.2-02)

The term "moisture content" refers to a moisture content of a water absorbent resin. Specifically, a "moisture content" is a value (unit; weight %) calculated from an amount lost from drying 1 g of a water-absorbing resin at 105° C. for 3 hours. For the present invention, the drying temperature is changed to 180° C., one sample is measured five times, and an average of the five measurements is employed. Further, the moisture content of a crosslinked hydrogel polymer is measured under a condition where the weight of a sample, the drying temperature, and the drying time are changed to 2 g, 180° C., and 16 hours, respectively. Furthermore, a value calculated by {100−moisture content (weight %)} is "resin solid content" for the present invention, and the value is applicable to both a water-absorbing resin and a crosslinked hydrogel polymer.

(1-4) "SFC"

The term "SFC" according to the present invention is an acronym for "saline flow conductivity", and refers to the liquid permeability (unit; $\times 10^{-7} \cdot cm^3 \cdot s \cdot g^{-1}$) of a water-absorbing resin per a 0.69 weight % aqueous sodium chloride solution under a load of 2.07 kPa. A larger SFC value indicates a water-absorbing resin having a higher liquid permeability. "SFC" is measured in conformity with the SFC testing method described in the specification of U.S. Pat. No. 5,849,405.

(1-5) "Water Absorption Time According to a Vortex Method"

The term "water absorption time according to a vortex method" as used for the present invention is a water absorption time determined in conformity with the "Testing Method for Water Absorption Rate of Super Absorbent Polymers" described in JIS K7224. The term refers to a time period (unit; seconds) necessary for 2 g of a water-absorbing resin to absorb 50 g of physiological saline (specifically, a 0.9 weight % aqueous sodium chloride solution). The present specification may use the expressions "water absorption time" or "Vortex" to refer to a "water absorption time according to a vortex method".

(1-6) "Elastic Modulus Index"

"Elastic modulus index" as used for the present invention is a value (unit; $Pa/m^2$) obtained from an elastic modulus measured by the method described below and correcting said elastic modulus using a theoretical surface area and a CRC of swollen gel particles, and the "elastic modulus index" is a value that serves as an index for evaluating the performance of a water-absorbing resin. The term "swollen gel particles" refers to gel particles prepared by swelling a water-absorbing resin with a swelling liquid (in particular, deionized water). The present specification may use the acronym "EMI" to refer to "elastic modulus index". The Examples below will deal with how an EMI is measured and calculated specifically.

(1-7) "Diffusion Absorbency Period"

The term "diffusion absorbency period" as used for the present invention refers to a total time period (unit; seconds) necessary for a water-absorbing resin to absorb all of a 0.9 weight % aqueous sodium chloride solution that has been injected onto the water-absorbing resin in a plurality of portions.

(1-8) Other

In the present specification, a range "X to Y" means "not less than X and not more than Y". "t (ton)", which is a unit of weight, means "metric ton". Moreover, unless otherwise specified, "ppm" means "ppm by weight". "weight" is synonymous with "mass", "weight %" is synonymous with "mass %", and "parts by weight" is synonymous with "parts by mass". Further, " . . . acid (salt)" means " . . . acid and/or salt thereof", and "(meth)acrylic" means "acrylic and/or methacrylic". In addition, "main component" means accounting for not less than 51% of the whole.

[2] Physical Properties of Water-Absorbing Resin Powder

A water-absorbing resin powder in accordance with the present invention contains a polyacrylic acid (salt)-based water-absorbing resin as a main component, is surface-crosslinked, and satisfies (1) to (3) below:

(1) a proportion of the water absorbent resin powder having a particle size of not less than 150 μm and less than 850 μm is not less than 90 weight %;

(2) a water absorption time according to a vortex method is not more than 42 seconds; and (3) an elastic modulus index (600-500) is not less than 5500.

The following description will discuss a water-absorbing resin powder in accordance with the present invention, mainly the requirements (1) to (3) above. In a case where a water-absorbing resin powder in accordance with the present invention is used as an absorbent body for an absorbing article such as a disposable diaper, the water-absorbing resin powder preferably satisfies not only the physical properties (1) to (3) above, but also one or more physical properties selected from the physical properties described below in (2-1) to (2-8).

(2-1) Particle size, weight average particle diameter (D50), and logarithmic standard deviation (σζ) of particle size distribution The term "particle size" as used for the present invention refers to a distribution of particle diameters of a water-absorbing resin powder that is defined by using a JIS standard sieve (JIS Z8801-1 (2000)). The "water-absorbing resin powder having particle sizes of not less than 150 μm to less than 850 μm" in (1) above refers to a water-absorbing resin powder that passes through a JIS standard sieve with a mesh size of 850 μm but does not pass through a JIS standard sieve with a mesh size of 150 μm.

A water-absorbing resin powder in accordance with the present invention is arranged such that a proportion of the water-absorbing resin powder having particle sizes of not less than 150 μm to less than 850 μm as stated in (1) above is essentially not less than 90 weight %, preferably not less than 95 weight %, more preferably not less than 97 weight %, even more preferably not less than 98 weight % (with the upper limit of 100 weight %).

Further, a water-absorbing resin powder in accordance with the present invention is arranged such that a proportion of the water-absorbing resin powder having particle sizes of not less than 150 μm and less than 710 μm is preferably not less than 90 weight %, more preferably not less than 95 weight %, even more preferably not less than 97 weight %, especially even more preferably not less than 98 weight % (with the upper limit of 100 weight %).

Further, from the viewpoint of improvement in physical properties of a water-absorbing resin powder, fine particles that pass through a JIS standard sieve with a mesh size of 150 µm (that is, a water-absorbing resin powder having particle sizes of less than 150 µm) are preferably fewer. Such fine particles account for preferably 0 weight % to 5 weight %, more preferably 0 weight % to 3 weight %, even more preferably 0 weight % to 1 weight %, per the entire water-absorbing resin powder. Large particles that do not pass through a JIS standard sieve with a mesh size of 850 µm or 710 µm (that is, a water-absorbing resin powder having particle sizes of not less than 850 µm or not less than 710 µm) are preferably fewer as well. Such large particles account for preferably 0 weight % to 5 weight %, more preferably 0 weight % to 3 weight %, even more preferably 0 weight % to 1 weight %, per the entire water-absorbing resin powder. The proportion of such particles (that is, fine particles and/or large particles above) is preferably lower, desirably 0 weight %, preferably not less than 0.1 weight %.

A water-absorbing resin powder in accordance with the present invention is arranged such that the content (particle size distribution) of each particle size range is as follows:

(a) The proportion of the water-absorbing resin powder having particle sizes of not less than 150 µm and less than 300 µm is preferably 5 weight % to 50 weight %, more preferably 10 weight % to 40 weight %, even more preferably 15 weight % to 35 weight %.

(b) The proportion of the water-absorbing resin powder having particle sizes of not less than 300 µm and less than 425 µm is preferably 10 weight % to 60 weight %, more preferably 15 weight % to 35 weight %, even more preferably 20 weight % to 40 weight %.

(c) The proportion of the water-absorbing resin powder having particle sizes of not less than 425 µm and less than 500 µm is preferably 5 weight % to 50 weight %, more preferably 10 weight % to 40 weight %, even more preferably 15 weight % to 35 weight %.

(d) The proportion of the water-absorbing resin powder having particle sizes of not less than 500 µm and less than 600 µm is preferably 5 weight % to 50 weight %, more preferably 10 weight % to 40 weight %, even more preferably 15 weight % to 35 weight %.

(e) The proportion of the water-absorbing resin powder having particle sizes of not less than 600 µm and less than 850 µm or not less than 600 µm and less than 710 µm is preferably 0.1 weight % to 50 weight %, more preferably 0.5 weight % to 40 weight %, even more preferably 1 weight % to 30 weight %.

The respective proportions of (a) to (e) above can be selected for any combination as long as the above particle size (that is, not less than 150 µm and less than 850 µm or not less than 150 µm and less than 710 µm) is satisfied. Assuming that a water-absorbing resin powder in accordance with the present invention has a weight of 100 weight %, the water-absorbing resin powder in accordance with the present invention is arranged such that the total proportion of the water-absorbing resin powder having particle sizes defined in (a) to (e) above is preferably 90 weight % to 100 weight %, more preferably 95 weight % to 100 weight %, even more preferably 97 weight % to 100 weight %.

A water-absorbing resin powder in accordance with the present invention has a weight average particle diameter (D50) of preferably 300 µm to 500 µm, more preferably, 320 µm to 480 µm, even more preferably 340 µm to 460 µm, from the viewpoint of physical property improvements.

A water-absorbing resin powder in accordance with the present invention has a logarithmic standard deviation (σζ) of preferably 0.25 to 0.45, more preferably 0.27 to 0.43, even more preferably 0.29 to 0.41, from the viewpoint of physical property improvements.

A water-absorbing resin powder in accordance with the present invention is arranged such that the respective ranges of the weight average particle diameter (D50) and logarithmic standard deviation (σζ) can be combined as appropriate. For example, a water-absorbing resin powder in accordance with the present invention can have a weight average particle diameter (D50) of 300 µm to 500 µm and a logarithmic standard deviation (σζ) of 0.25 to 0.45.

(2-2) Water Absorption Time According to a Vortex Method

Water absorbent resin powder in accordance with the present invention is, from the viewpoint of water absorbency, arranged to have a water absorption time according to a vortex method that is essentially not more than 42 seconds, preferably not more than 40 seconds, more preferably not more than 35 seconds, even more preferably not more than 30 seconds, especially even more preferably not more than 25 seconds. The water absorption time is not limited to a particular length as long as the lower limit value is more than 0 seconds. A typical lower limit value is, however, preferably not less than 5 seconds, more preferably not less than 10 seconds.

A water absorption time of more than 42 seconds is not preferable because such water absorbent resin powder will be insufficient in liquid absorption and may cause discomfort to the user of the absorbing article such as a disposable diaper.

(2-3) Elastic Modulus Index

A water-absorbing resin powder in accordance with the present invention has an elastic modulus index with a preferable range that varies according to the particle size of the water-absorbing resin powder. This is because accurately measuring an elasticity for use in calculation of an elastic modulus index requires adjusting the particle sizes of a water-absorbing resin powder as a measurement target to a particular range. The following description will discuss a preferable range of the elastic modulus index for each particle size range. The description below uses the expression "EMI (600-500)" to refer to the elastic modulus index of a water-absorbing resin powder having particle sizes of not less than 500 µm and less than 600 µm.

A water-absorbing resin powder in accordance with the present invention meets the essential requirement of the elastic modulus index (600-500) of not less than 5500. The water-absorbing resin powder can, as long as it meets the above requirement, have any appropriate combination of respective preferable ranges of the elastic modulus indexes described in (2-3-1) to (2-3-5) below regarding elastic modulus indexes of other particle sizes. Examples include: a water-absorbing resin powder having an elastic modulus index (600-500) of not less than 5500, an elastic modulus index (500-425) of not less than 4500, and an elastic modulus index (425-300) of not less than 3500; a water-absorbing resin powder having an elastic modulus index (600-500) of not less than 6000 and an elastic modulus index (500-425) of not less than 4500; and a water-absorbing resin powder having an elastic modulus index (600-500) of not less than 6500, an elastic modulus index (500-425) of not less than 5000, an elastic modulus index (425-300) of not less than 4500, and an elastic modulus index (710-600) of not less than 5000.

(2-3-1) Elastic Modulus Index (600-500)

A water-absorbing resin powder in accordance with the present invention has an elastic modulus index (600-500) of essentially not less than 5500, preferably not less than 6000, more preferably not less than 6500, even more preferably not less than 7000. As demonstrated in the Examples, in a case where a water-absorbing resin powder meets the requirement of the water absorption time according to a vortex method of not more than 42 seconds, a larger elastic modulus index leads to a shorter diffusion absorbency period. In other words, a larger value of the elastic modulus index preferably allows for production of a water-absorbing resin powder having a more excellent diffusion absorbency property.

As described above, in the case where a water-absorbing resin powder meets the requirement of the water absorption time according to a vortex method of not more than 42 seconds, a larger value of the elastic modulus index is preferable. The upper limit value of the elastic modulus index is not limited to any particular value. The upper limit value is, however, typically preferably not more than 15000, more preferably not more than 11000, even more preferably not more than 7500, due to physical limitations.

A preferable range of the elastic modulus index varies according to the particle sizes of a water-absorbing resin powder as a measurement target. However, in the case where a water-absorbing resin powder meets the requirement of the water absorption time according to a vortex method of not more than 42 seconds, a larger value of the elastic modulus index should also tend to lead to a shorter diffusion absorbency period. The description below thus deals with only a preferable range of the elastic modulus index for each of the particle size ranges below.

(2-3-2) Elastic Modulus Index (500-425)

A water-absorbing resin powder in accordance with the present invention has an elastic modulus index (500-425) of preferably not less than 4500, more preferably not less than 5000, even more preferably not less than 5500, especially even more preferably not less than 6000, most preferably not less than 6500. The upper limit value of the elastic modulus index is not limited to any particular value. The upper limit value is, however, typically preferably not more than 14500, more preferably not more than 10500, even more preferably not more than 7000, due to physical limitations.

(2-3-3) Elastic Modulus Index (425-300)

A water-absorbing resin powder in accordance with the present invention has an elastic modulus index (425-300) of preferably not less than 3500, more preferably not less than 4000, even more preferably not less than 4500, further even more preferably not less than 5000, especially even more preferably not less than 5500, most preferably not less than 6000. The upper limit value of the elastic modulus index is not limited to any particular value. The upper limit value is, however, typically preferably not more than 14000, more preferably not more than 10000, even more preferably not more than 6500, due to physical limitations.

(2-3-4) Elastic Modulus Index (710-600)

A water-absorbing resin powder in accordance with the present invention has an elastic modulus index (710-600) of preferably not less than 5500, more preferably not less than 6000, even more preferably not less than 6500, especially even more preferably not less than 7000, most preferably not less than 7500. The upper limit value of the elastic modulus index is not limited to any particular value. The upper limit value is, however, typically preferably not more than 15500, more preferably not more than 11500, even more preferably not more than 8000, due to physical limitations.

(2-3-5) Elastic Modulus Index (300-150)

A water-absorbing resin powder in accordance with the present invention has an elastic modulus index (300-150) of preferably not less than 3500, more preferably not less than 4000. The upper limit value of the elastic modulus index is not limited to any particular value. The upper limit value is, however, typically preferably not more than 13500, more preferably not more than 9500, even more preferably not more than 4500, due to physical limitations.

(2-4) Internal Gas Bubble Ratio

A water-absorbing resin powder in accordance with the present invention has an internal gas bubble ratio of preferably 0% to 3.7%, more preferably 1.3% to 3.3%, even more preferably 1.7% to 3.0%. It has been known that publicly known foaming polymerization produces a water-absorbing resin powder having a high water absorption speed. In contrast, a water-absorbing resin powder in accordance with the present invention, although it has an internal gas bubble ratio lower than that (that is, an internal gas bubble ratio of approximately 4%) of a water-absorbing resin powder produced by publicly known foaming polymerization, not only has a high water absorption speed, but also has a high elasticity and an excellent diffusion absorbency property as described above. The Examples will later deal with how an internal gas bubble ratio is measured.

(2-5) Surface Tension

A water-absorbing resin powder in accordance with the present invention has a surface tension of preferably not less than 69 mN/m, more preferably not less than 70 mN/m, even more preferably not less than 71 mN/m. The upper limit value of the surface tension is preferably not more than 74 mN/m, more preferably not more than 73 mN/m, from the viewpoint of typical measurement accuracy. With the surface tension within the above range, in a case where the water-absorbing resin powder is used as an absorbent body for an absorbing article such as a disposable diaper, it is preferably possible to significantly reduce the re-wet. The Examples will deal with how a surface tension is measured.

(2-6) CRC

A water-absorbing resin powder in accordance with the present invention has a CRC (centrifuge retention capacity) of preferably 25 g/g to 50 g/g, more preferably 26 g/g to 45 g/g, even more preferably 26 g/g to 33 g/g. The CRC is preferably not less than 25 g/g from the viewpoint of sufficient liquid absorbing capability, and preferably not more than 50 g/g from the viewpoint of maintained diffusion property. The CRC can be controlled as appropriate on the basis of the amount of crosslinking agent for polymerization and later surface crosslinking (secondary crosslinking).

(2-7) Surface Crosslinking

A water-absorbing resin powder in accordance with the present invention is in a state where the crosslinking density at and in the vicinity of the surface is high, that is, it is surface-crosslinked. The water-absorbing resin powder thus has an AAP (fluid retention capacity under pressure) of preferably 8 g/g to 29 g/g, more preferably 10 g/g to 27 g/g, even more preferably 12 g/g to 25 g/g, and/or a SFC (saline flow conductivity) of preferably not less than $5 \times 10^{-7} \cdot cm^3 \cdot g^{-1}$, more preferably not less than $10 \times 10^{-7} \cdot cm^3 \cdot g^{-1}$, even more preferably not less than $20 \times 10^{-7} \cdot cm^3 \cdot g^{-1}$. In other words, a water-absorbing resin powder having an AAP and/or SFC each within the above range is surface-crosslinked.

(2-8) Diffusion Absorbency Period

A water-absorbing resin powder in accordance with the present invention has a diffusion absorbency period of preferably not more than 100 seconds, more preferably not more than 95 seconds, even more preferably not more than 90 seconds, especially even more preferably not more than 85 seconds. A shorter diffusion absorbency period is more preferable. The lower limit value thereof is thus not limited to any particular value. The lower limit value is, however, preferably more than 5 seconds, more preferably not less than 10 seconds, even more preferably not less than 20 seconds, especially even more preferably not less than 40 seconds.

A shorter diffusion absorbency period indicates a water-absorbing resin powder having an excellent diffusion absorbency property. In a case where such a water-absorbing resin powder is used as an absorbent body for an absorbing article such as a disposable diaper, it is preferably possible to achieve an unconventionally excellent liquid absorption and reduce liquid leakage.

[3] Method for Measuring Elastic Modulus of Water-Absorbing Resin Powder

The term "elastic modulus index" described above is a value obtained by correcting the elastic modulus on the basis of a theoretical surface area and CRC of swollen gel particles, and is a value that serves as an index of the performance of a water-absorbing resin powder. The term "swollen gel particles" refers to particles of a swollen gel prepared by swelling a water-absorbing resin powder with a swelling liquid. The present specification may use the acronym "EMI" to refer to "elastic modulus index".

The inventors of the present invention have discovered that a water-absorbing resin powder that is highly elastic and that has an excellent water absorption time according to a vortex method (hereinafter also referred to simply as "water absorption time") exhibits an excellent diffusion absorbency property.

It has, however, been discovered that expressing the elasticity in terms of the elastic modulus involves the following issue: The elastic modulus varies according to the fluid retention capacity. It has been known that for example, an improved fluid retention capacity leads to a reduced polymer density of a water-absorbing resin powder and a reduced elastic modulus. This has revealed that the elasticity is preferably expressed on the basis of an index that takes influence of the fluid retention capacity of a water-absorbing resin powder into consideration.

An elastic modulus can be measured with use of a rheometer described below. For the measurement, swollen gel particles are held with a surface of a dish and a surface of a parallel plate of the rheometer to impose a load. In a case where the water-absorbing resin powder has a particle size distribution at this stage, the parallel plate surface first comes into contact with swollen gel particles having large particle sizes, so that particles having small particle sizes are not sandwiched. This indicates the need to measure an elastic modulus after, for example, classification for adjusting the particle sizes of a water-absorbing resin powder to an extent.

A typical product of a water-absorbing resin powder has a particle size distribution. A water-absorbing resin powder having small particle sizes has a large surface area, and thus has an elastic modulus larger than that of a water-absorbing resin powder having larger particle sizes. However, so-called fine powder, that is, particles having particle sizes of, for example, less than 150 μm, has a poor water absorption performance, and is not suitable for practical use.

The inventors have discovered that a water-absorbing resin powder that is highly elastic and that has a short water absorption time exhibits an excellent diffusion absorbency property. However, in a case where the elasticity is expressed on the basis of the elastic modulus, the elastic modulus and the performance of the water-absorbing resin powder are unfortunately not necessarily correlated to each other.

In view of that, the inventors have derived the "elastic modulus index", which is a value obtained by correcting the elastic modulus on the basis of the fluid retention capacity of a water-absorbing resin powder and a theoretical surface area of swollen gel particles. The inventors have thus discovered that the elastic modulus index accurately expresses the elasticity of a water-absorbing resin powder in view of influence of the fluid retention capacity of a water-absorbing resin powder and the theoretical surface area of swollen gel particles on the value of the elastic modulus index and that the elastic modulus index is a value that correlates to the performance of a water-absorbing resin powder.

An elastic modulus index can be calculated on the basis of Formula (3) below. The Examples will deal in detail with how an elastic modulus index is calculated specifically.

[Math. 1]

$$\text{EMI} = \text{Elastic modulus } G'/(\text{theoretical surface area (TGS) of swollen gel particles}) \times \text{CRC} \quad \text{Formula (3)}$$

An elastic modulus index is, as described above, an important index that serves as an indicator of the performance of a water-absorbing resin powder. An elastic modulus index is, however, a value obtained by correcting the value of the elastic modulus of a water-absorbing resin powder; if the elastic modulus is not calculated correctly, the elastic modulus index cannot be calculated correctly as well.

In view of that, the inventors have conducted studies for a method for measuring an elastic modulus that allows for correct measurement of the elastic modulus, and have successfully established such a method.

A method in accordance with the present invention for measuring the elastic modulus of a water-absorbing resin powder includes: a classification step of classifying a water-absorbing resin powder (A) by using two or more sieves having different mesh sizes so as to obtain a water-absorbing resin powder (B);

a swelling step of swelling the water-absorbing resin powder (B) in a swelling liquid to obtain swollen gel;

a containing step of containing the swollen gel into a container section having a horizontal bottom surface;

a load imposing step of imposing a load perpendicularly to the swollen gel, which is held in the bottom surface that is in contact with the swollen gel, with a plate-shaped member that is parallel to the bottom surface, the load being discontinuously increased up to a target load of at least not less than 2.4 kPa; and a measurement step of measuring a storage elastic modulus under a predetermined load in the load imposing step, at least a portion of the bottom surface and/or the plate-shaped member that comes in contact with the swollen gel is made of aluminum.

With reference to FIG. 1, the following description will discuss a method for measuring the elastic modulus.

FIG. 1 shows diagrams each illustrating an appearance of an example device for use in measuring the elastic modulus of a water-absorbing resin powder. FIG. 1 illustrates the device (rheometer) 300, a dish (container section) 40 configured to contain a swollen water-absorbing resin powder (hereinafter referred to as "swollen gel"), swollen gel 41, and a parallel plate (plate-shaped member) 42 (for example, disposable plate named "Part, No. 12081SPPYU50-07", available from Anton-Paar, is used). The parallel plate (plate-shaped member) 42 is configured to be capable of being fitted in the dish (container section) 40.

(a) of FIG. 1 is a perspective view of an appearance of each member of the rheometer 300. (b) of FIG. 1 is a longitudinal cross-sectional view of the rheometer 300 in a state where the parallel plate (plate-shaped member) 42 is fitted in the dish (container section) 40. The rheometer 300, the dish 40, and the parallel plate 42 are oriented strictly horizontally.

The elastic modulus is preferably measured by using a device such as the rheometer 300, sandwiching swollen gel 41 between the dish (container section) 40 and the parallel plate (plate-shaped member) 42, and providing vibrations to the swollen gel 41. This allows for correct measurement.

FIG. 1 shows a rotary shaft 43 oriented perpendicularly to the parallel plate (plate-shaped member) 42 and the dish (container section) 40. After the parallel plate (plate-shaped member) 42 is fitted in the dish (container section) 40 as illustrated in (b) of FIG. 1, rotating the rotary shaft 43 as, for example, indicated by the arrow in FIG. 1 can provide vibrations to the swollen gel 41. During the rotation, the dish (container section) 40 is fixed and not rotated. The rotation angle during the rotation is controlled on the basis of a strain (unit; %) as a normal set value of the device. The strain is, for example, preferably 0.005% to 2%, more preferably 0.01% to 1%, even more preferably 0.02% to 0.5%.

FIG. 1 shows the rotary shaft 43 being disposed on the parallel plate (plate-shaped member) 42. The present invention is, however, not necessarily limited to such a configuration. The rheometer 300 may be configured, for example, such that the rotary shaft 43 is disposed on the dish (container section) 40 perpendicularly to the parallel plate (plate-shaped member) 42 and the dish (container section) 40. With this configuration, the parallel plate (plate-shaped member) 42 is fixed and not rotated.

In a case where particles that greatly vary in particle size are to be sandwiched as a measurement target, particles having small particle sizes cannot be sandwiched and fail to be a measurement target. This may prevent correct measurement. A measurement target is thus preferably a water-absorbing resin powder having particle sizes within a limited range.

Measuring the elastic modulus of a water-absorbing resin powder having particle sizes within a limited range makes it possible to reflect variations in the respective shapes of the particles (for example, particles each having a shape similar to a sphere and/or particles each having a flake shape) in the measurement result within the particle size range. In other words, the elastic modulus is a large value in a case where more particles have high-performance shapes similar to a sphere or in a case where fewer particles have low-performance flake shapes.

A method in accordance with the present invention for measuring the elastic modulus of a water-absorbing resin powder includes a classification step of classifying a water-absorbing resin powder (A) by using two or more sieves having different mesh sizes so as to prepare a water-absorbing resin powder (B) having particle sizes within a limited range. The water-absorbing resin powder (A) refers to a water-absorbing resin powder before classification. The water-absorbing resin powder (B) refers to a water-absorbing resin powder prepared through classification, and specifically refers to a water-absorbing resin powder that did not pass through the sieve having the smallest mesh size among the two or more sieves having different mesh sizes.

The two or more sieves having different mesh sizes are preferably selected from sieves having mesh sizes of 710 μm to 150 μm, and are each preferably a JIS standard sieve (JIS Z8801-1 (2000)) for accurate classification. The two or more sieves can each be, for example, a JIS standard sieve having a mesh size of 710 μm, 600 μm, 500 μm, 425 μm, 300 μm, 150 μm, or the like.

A water-absorbing resin powder having particle sizes of not less than 600 μm and less than 710 μm is prepared, for example, as follows: A water-absorbing resin powder (A) is classified by using the sieve having a mesh size of 710 μm. A water-absorbing resin powder that has passed through the above sieve is further classified by using a JIS standard sieve having a mesh size of 600 μm. Particles that remain on that sieve are recovered. This makes it possible to prepare a water-absorbing resin powder having particle sizes of not less than 600 μm and less than 710 μm (corresponding to the "water-absorbing resin powder (B)" above). This is an example involving use of two sieves having different mesh sizes. The present invention is, however, not limited to such a configuration. The present invention may be configured to appropriately use three or more sieves having different mesh sizes so as to prepare a water-absorbing resin powder having desired particle sizes.

The water-absorbing resin powder (B) is preferably arranged such that the mesh size of a sieve that the water-absorbing resin powder (B) can pass and the mesh size of a sieve that the water-absorbing resin powder (B) cannot pass differ from each other by not more than 200 μm. This arrangement adjusts the particle size range to not more than 200 μm. This in turn makes it possible to prepare a measurement target having more limited particle sizes, which is preferable for correct measurement of the elastic modulus. The above water-absorbing resin powder (B) (which is arranged such that the mesh size of a sieve that the water-absorbing resin powder (B) can pass and the mesh size of a sieve that the water-absorbing resin powder (B) cannot pass differ from each other by not more than 200 μm) can be prepared by, for example, classifying a water-absorbing resin powder (A) by using two JIS standard sieves having mesh sizes different from each other by not more than 200 μm.

The water-absorbing resin powder (B), which has been prepared as described above and which has particle sizes within a limited range, is then subjected to a swelling step of swelling a water-absorbing resin powder (B) in a swelling liquid to prepare swollen gel. The swelling liquid is preferably a liquid having an ionic strength of 0 to 2.1. Examples of the swelling liquid include deionized water, deionized water, and distilled water.

A method in accordance with the present invention for measuring the elastic modulus uses, as the swelling liquid, deionized water (specifically, deionized water that has an ionic strength of substantially 0 and that meets a deionized water standard of preferably Grade 3, more preferable Grade 2, in ISO3696). In a case where the measurement method is to be improved or changed while the technical concept of the measurement method of the present invention is maintained, and deionized water having a different ionic strength is used for the measurement, such an ionic strength is preferably 0 to 1.0, more preferably 0 to 0.1, from the viewpoint of a swelling rate suitable for the measurement of the elastic modulus.

Regarding a water-absorbing resin powder (B) to be subjected to the swelling step, CRCdw thereof is measured in advance of being subjected to the swelling step. The term "CRCdw" refers to a fluid retention capacity without pressure that is calculated through an operation identical to the CRC (fluid retention capacity without pressure) measurement except that the 0.9 weight % aqueous sodium chloride solution is replaced with the above swelling liquid, the amount of a water-absorbing resin powder for use in the measurement is changed from 0.2 g to 0.05 g, and the length of the free swelling is set to 16 hours, and on the basis of Formula (4) below. The present specification may refer to CRCdw also as "centrifuge retention capacity (absorbency) after deionized water swelling"

In a case where a device such as the rheometer 300 is used and swollen gel 41 is held in the dish (container section) 40 and the parallel plate (plate-shaped member) 42 as described above, the swollen gel 41 preferably has a substantially uniform volume in order for the swollen gel 41 to be held evenly and for a load to be imposed on the swelling gel. Measuring CRCdw in advance makes it possible to predict the weight of a water-absorbing resin powder (B) that has been swollen to become swollen gel. Weighing out a water-absorbing resin powder (B) having a weight as calculated back from the above weight and subjecting the water-absorbing resin powder (B) to the swelling step makes it possible to prepare swollen gel 41 having a substantially uniform volume.

In view of that, a water-absorbing resin powder (B) is weighed out to have a weight calculated by dividing a desired weight for the swollen gel 41 by the determined CRCdw, and is mixed with a swelling liquid in, for example, a publicly known plastic container to be swollen. The above weighing is preferably as accurate as possible for correct measurement. The weighing is, for example, preferably carried out at an accuracy of not less than ±0.0005 g.

The swelling liquid is used in an amount of preferably not more than 100% of the capacity of the dish (container section), more preferably not more than 70%, even more preferably not more than 50%, in view of the limit on the capacity of the dish (container section) of the rheometer 300. The swelling time is preferably not less than 30 minutes and not more than 48 hours, more preferably not less than 12 hours and not more than 36 hours, even more preferably not less than 16 hours and not more than 24 hours, in order to prepare gel that is sufficiently in an equilibrium swelling state.

The swollen gel prepared through the swelling step is placed in the dish (container section) 40 of the rheometer 300 (corresponding to the swollen gel 41 illustrated in FIG. 1). The dish (container section) 40 has a horizontal bottom surface as illustrated in FIG. 1. The swollen gel 41 contained in the dish (container section) 40 is preferably immersed in the swelling liquid. This makes it possible to impose a load (pressure) on the swollen gel 41 more evenly and prevent the swollen gel 41 from being dried during the measurement. Regarding the degree of the immersion, the swollen gel 41 is preferably not exposed above the liquid surface of the swelling liquid.

The swollen gel 41 has a weight per bottom surface area of the dish (container section) 40 that is preferably not more than 5.0 mg/mm$^2$, more preferably not more than 3.0 mg/mm$^2$, even more preferably not more than 1.5 mg/mm$^2$, in order to reduce the measurement error during the measurement of the elastic modulus.

The swollen gel 41 is, as illustrated in (b) of FIG. 1, held in the bottom surface of the dish (container section) 40 in contact with the swollen gel 41 and the parallel plate (plate-shaped member) 42, which is parallel to the above bottom surface. As described above, the swollen gel 41 has been prepared by measuring CRCdw of the water-absorbing resin powder (B) in advance, weighing out the water-absorbing resin powder (B) to achieve a desired weight, and swelling the water-absorbing resin powder (B). The swollen gel 41 thus has a substantially uniform volume, making it possible to substantially evenly sandwich all the swollen gel 41 contained in the dish (container section) 40.

The inner diameter of the dish (container section) 40, which has a horizontal bottom surface, and the outer diameter of the parallel plate (plate-shaped member) 42 are different in size by preferably not more than 3 mm, more preferably not more than 2 mm, even more preferably not more than 1 mm, in order for the parallel plate (plate-shaped member) 42 to be fitted smoothly in the dish (container section) 40.

The phrase "horizontal bottom surface" means that the dish (container section) 40 has a bottom surface that is substantially free from unevenness.

The bottom surface of the dish (container section) 40 or at least that portion of the parallel plate (plate-shaped member) 42 which comes in contact with the swollen gel 41 is made of aluminum. This configuration can increase the tightness of the contact between the swollen gel 41 and both the bottom surface of the dish (container section) 40 and the parallel plate (plate-shaped member) 42. This can in turn further ensure the sandwiching, and allows the elastic modulus to be measured more accurately. This is presumably because the acrylic acid as a main component of water-absorbing resin has a negative charge and moderately interacts with the aluminum, which has a slight positive charge.

If, for example, the bottom surface of the dish (container section) 40 or that portion of the parallel plate (plate-shaped member) 42 which is in contact with the swollen gel 41 is made of stainless steel, the swollen gel 41 will not be in sufficiently tight contact with the bottom surface of the dish (container section) 40 and the parallel plate (plate-shaped member) 42, and will be slidable thereon, making it impossible to accurately measure the elastic modulus.

The above expression "at least partially" means the following: Of the bottom surface of the dish (container section) 40 or that surface of the parallel plate (plate-shaped member) 42 which is parallel to the above bottom surface, not less than 50% of that portion which is in contact with the swollen gel 41 is preferably made of aluminum to produce the above effect, or in order of increasing preference, not less than 60%, not less than 70%, not less than 80%, or not less than 90%, most preferably 100%. Aluminum can be used in combination with, for example, stainless steel, brass, and/or the like.

The bottom surface of the dish (container section) 40 and the parallel plate (plate-shaped member) 42, which is parallel to the above bottom surface, are both preferably configured such that at least the portion that comes in contact with the swollen gel 41 is made of aluminum. With this configuration, the two members that sandwich the swelling gel are both configured such that at least the portion that comes in contact with the swollen gel 41 is made of aluminum. This makes it possible to more reliably produce the above effect.

Fitting the parallel plate (plate-shaped member) 42 into the dish (container section) 40 allows the swollen gel 41 to be held in the bottom surface of the dish (container section) 40 and a surface of the parallel plate (plate-shaped member) 42 that is parallel to the above bottom surface.

The swollen gel 41 is subjected to a load imposing step of imposing a load onto the swollen gel 41 perpendicularly thereto while increasing the load discontinuously up to a target load of at least not less than 2.4 kPa. The load can be imposed, as illustrated in (a) of FIG. 1, by pressing down the parallel plate (plate-shaped member) 42 toward the dish (container section) 40 while keeping the parallel plate (plate-shaped member) 42 and the bottom surface of the dish (container section) 40 parallel to each other. Setting conditions for the rheometer 300 allows the rheometer 300 to automatically impose a load until the load reaches the target load in accordance with the set conditions.

The expression "imposing a load . . . while increasing the load discontinuously up to a target load" means increasing a load stepwise until a target load is imposed per unit area of that surface of the parallel plate (plate-shaped member) 42 which is in contact with the swollen gel 41. In other words, the above expression does not mean increasing a load continuously and gradually; it means increasing a load in such a manner that a fixed load is imposed for a certain time frame, and an increased, fixed load is imposed for the following certain time frame, and so forth. For example, the load is increased in such a manner that a load of 1 kPa is imposed for 10 seconds, after which the load is increased, so that a load of 2 kPa is imposed for the following 10 seconds.

A target load refers to a load finally imposed on swollen gel. The phrase "target load of at least not less than 2.4 kPa" may refer to a case where the target load is 2.4 kPa, and a load is imposed while the load is increased discontinuously until it reaches 2.4 kPa, or a case where the target load is more than 2.4 kPa, and a load is imposed while the load is increased discontinuously until it reaches the target load.

Imposing a load while increasing the load discontinuously up to a target load of at least not less than 2.4 kPa as described above makes it possible to produce the effect of stabilizing the arrangement of the swollen gel 41 and reducing the measurement error.

A target load of less than 2.4 kPa is not preferable because it will fail to apply a pressure to the swollen gel 41 that is necessary to measure the elastic modulus. In a case where the target load is not less than 2.4 kPa, it has an upper limit value of preferably not more than 30 kPa, more preferably not more than 26 kPa, even more preferably not more than 22 kPa, in order to prevent an excessive pressure on the swollen gel 41.

The rate at which the load is increased discontinuously is not limited to any particular rate. The rate is, however, preferably not less than 0.1 kPa/s, more preferably not less than 0.3 kPa/s, even more preferably not less than 0.5 kPa/s, in order to avoid an extra measurement time period.

The load imposing step includes a measurement step of measuring a storage elastic modulus under a predetermined load. The load imposing step is a step of imposing a load while increasing the load discontinuously up to a target load of at least not less than 2.4 kPa as described above. The phrase "measuring a storage elastic modulus under a predetermined load" means an operation of, in the process of increasing a load discontinuously, measuring the storage elastic modulus during a time frame in which a fixed load is imposed. In other words, in order to increase a load discontinuously, the operation is repeated in which a fixed load is imposed for a certain time frame, and an increased, fixed load is imposed for the following time frame as described above. The above phrase means measuring a storage elastic modulus during each time frame.

The interval of measuring a storage elastic modulus is not limited to any particular length. The interval is, however, preferably not more than 20 seconds, more preferably not more than 10 seconds, even more preferably not more than 5 seconds, in view of the risk of an increased error.

The elastic modulus can be calculated by determining the arithmetic average of, among the storage elastic moduli measured, values measured during the respective time frames in each of which a target load is imposed. Measurement values for use in determining the arithmetic average are not particularly limited. However, a larger number of measurement values are preferable. Measurement values are more stable at a later time point during time frames of measurement. The arithmetic average may thus be of measurement values at respective points from the end of the measurement time frame (preferably 1 points to 10 points, more preferably 3 points to 5 points; 5 points in the Examples). The value of the elastic modulus obtained as described above is then corrected on the basis of the CRC of the water-absorbing resin powder and a theoretical surface area of swollen gel particles as shown in Formula (3) above for determination of the elastic modulus index.

As described above, a method in accordance with the present invention for measuring the elastic modulus of a water-absorbing resin powder includes: limiting the range of particle sizes of a water-absorbing resin powder as a measurement target; sandwiching the swollen gel with use of members in tight contact with the swollen gel; and imposing a load while increasing the load discontinuously up to a predetermined target load. This makes it possible to measure the elastic modulus accurately.

[4] Method for Producing Water-Absorbing Resin Powder

A water-absorbing resin powder in accordance with the present invention is highly elastic, has a high water absorption speed, and consequently has an excellent diffusion absorbency property as described above. This is presumably because the respective shapes of the particles are controlled more strictly, so that particles having flat shapes are excluded.

The following description will first discuss two embodiments in detail of a method for controlling particle shapes so that a water-absorbing resin powder will exhibit an excellent diffusion absorbency property, and then discuss other steps included in the method for producing a water-absorbing resin powder.

(4-1) Embodiment 1

A method in accordance with Embodiment 1 for producing a water-absorbing resin powder includes a step of classifying, by using at least two sieves each having a mesh size of not less than 150 μm and not more than 850 μm, a water-absorbing resin powder containing a polyacrylic acid (salt)-based water-absorbing resin as a main component and surface-crosslinked and obtaining a water-absorbing resin powder (i) remaining on a sieve (a) having the smallest mesh size among the sieves used; and a step of classifying the water-absorbing resin powder (i) by using a sieve (b) having rectangular mesh openings and obtaining water absorbent resin powder (ii) remaining on the sieve (b), the rectangular mesh openings each having long sides with a length that is larger than the mesh openings of the sieve (a) and that is not smaller than the length of the sides of the mesh openings of a sieve (c) for use in defining the upper limit value of the particle sizes of the water-absorbing resin powder (i), the rectangular mesh openings each having short sides with a length that is preferably not larger than two-thirds (more preferably not larger than a half) of the length of the long sides.

The method in accordance with Embodiment 1 is preferably arranged such that the mesh openings of the sieve (c) each have sides each with a length of not more than 710 μm and that the rectangular mesh openings each have long sides each with a length of not less than 710 μm and short sides each with a length of not more than 350 μm.

The "water-absorbing resin powder containing a polyacrylic acid (salt)-based water-absorbing resin as a main component and surface-crosslinked" is as described above.

The sieves each having a mesh size of not less than 150 μm and not more than 850 μm are each a sieve having square mesh openings each having sides each with a length of not less than 150 μm and not more than 850 μm, and are preferably JIS standard sieves. The sieves can each be, for example, a JIS standard sieve having a mesh size of 850 μm, 710 μm, 600 μm, 500 μm, 425 μm, 300 μm, 150 μm, or the like. The method in accordance with Embodiment 1 simply needs to use at least two kinds of sieves each having a mesh size of not less than 150 μm and not more than 850 μm.

Classifying the surface-crosslinked water-absorbing resin powder with use of at least two kinds of sieves each having a mesh size of not less than 150 μm and not more than 850 μm leaves, on the sieve (a) (which has the smallest mesh size among the sieves used), a water-absorbing resin powder (i) having particle sizes not smaller than the mesh openings of the sieve (a).

The water-absorbing resin powder (i) contains many particles each having a spherical shape or a shape close thereto, but may also contain particles each having a flat shape (flake-shaped particles). Particles having flat shapes cause a water-absorbing resin powder to have a poor elasticity and poor absorbent property, and are thus preferably removed.

In view of that, to remove particles having flat shapes, the method in accordance with Embodiment 1 includes classifying the water-absorbing resin powder (i) by using a sieve (b) having rectangular mesh openings and obtaining water absorbent resin powder (ii) remaining on the sieve (b). The sieve (b) can be, for example, a sieve provided with a conventionally publicly known top-cap metal gauze.

Figure 5:
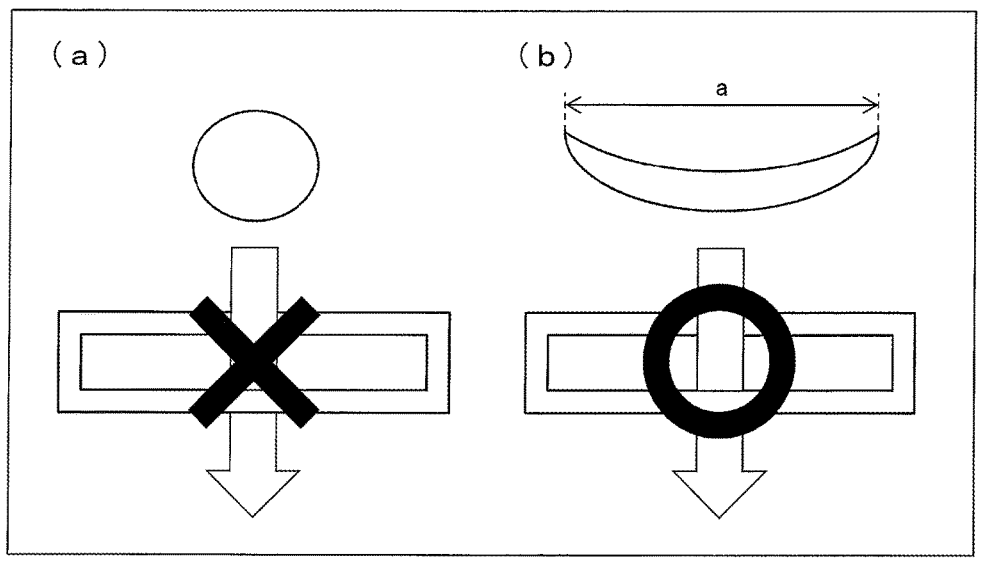
FIG. 5 shows diagrams each schematically illustrating how particles having flat shapes are removed with use of rectangular mesh openings.

FIG. 5 shows diagrams each schematically illustrating how particles having flat shapes are removed with use of rectangular mesh openings. (a) of FIG. 5 illustrates how a spherical particle cannot pass through a rectangular mesh opening. (b) of FIG. 5 illustrates how a particle having a flat shape can pass through a rectangular mesh opening in a case where the length "a" shown in FIG. 5 is smaller than the long sides of the rectangular mesh opening.

The rectangular mesh openings each have long sides with a length that is larger than the mesh openings of the sieve (a) out of the at least two kinds of sieves and that is not smaller than the length of the sides of the mesh openings of the sieve (c), which is a sieve for use in defining the upper limit value of the particle sizes of the water-absorbing resin powder (i).

The sieve (c) corresponds to a sieve having the second smallest mesh size among the at least two kinds of sieves each having a mesh size of not less than 150 μm and not more than 850 μm. Assuming, for example, that a surface-crosslinked water-absorbing resin powder is to be classified with use of three JIS standard sieves having respective mesh sizes of 850 μm, 710 μm, and 500 μm, the JIS standard sieve having a mesh size of 500 μm (that is, the smallest mesh size) corresponds to the sieve (a).

In this case, the sieve (a) catches thereon a water-absorbing resin powder (i) having particle sizes of not less than 500 μm and less than 710 μm. The upper limit value of the particle sizes of the water-absorbing resin powder (i) is defined by a sieve that has a mesh size larger than and closest to that of the sieve (a), that is, the JIS standard sieve having a mesh size of 710 μm. This corresponds to the sieve (c) above.

The rectangular mesh openings each have long sides with a length that is not smaller than the length of the sides of the mesh openings of the sieve (c), and the rectangular mesh openings each have short sides with a length that is preferably not larger than two-thirds (more preferably not larger than a half) of the length of the long sides. With this configuration, those particles of the water-absorbing resin powder (i) which pass through the sieve (c) but cannot pass through the sieve (b) (that is, the water absorbent resin powder (ii)) remain on the sieve (b). The water absorbent resin powder (ii) is formed of particles that are larger than the rectangular mesh openings, and can thus be regarded as particles having a low flatness. Particles that pass through the sieve (b) are, on the other hand, smaller than the rectangular mesh openings, and can thus be regarded as particles having a high flatness.

A water-absorbing resin powder that has passed through the sieve (a) may be mixed with a water-absorbing resin powder remaining on the sieve (b). In a case where, for example, the sieve (a) is a JIS standard sieve having a mesh size of 150 μm, a water-absorbing resin powder that has passed through the sieve (a) is regarded as so-called fine powder, whose performance as a water-absorbing resin is poor. Such a water-absorbing resin powder is not necessarily mixed with a water-absorbing resin powder remaining on the sieve (b).

The above steps may be repeated a plurality of times. For example, the following steps can be carried out:

(I) carrying out a step of classifying a surface-crosslinked water-absorbing resin powder by using a JIS standard sieve having a mesh size of 850 μm (corresponding to the sieve (c) above) and a JIS standard sieve having a mesh size of 710 μm (corresponding to the sieve (a) above) to prepare a water-absorbing resin powder (i) having particle sizes of not less than 710 μm and less than 850 μm, and removing flat-shaped particles by using a sieve (b) having mesh openings each having long sides with a length of not less than 850 μm and short sides with a length of not larger than two-thirds (more preferably not larger than a half) of 850 μm to prepare water absorbent resin powder (ii); and (II) carrying out a step of classifying, by using a JIS standard sieve having a mesh size of 500 μm (corresponding to the sieve (a) above), particles that have passed through the JIS standard sieve having a mesh size of 710 μm and that have particle sizes less than 710 μm, to prepare a water-absorbing resin powder (F) having particle sizes of not less than 500 μm and less than 710 μm, and further removing flat-shaped particles by using a sieve (b) having mesh openings each having long sides with a length of not less than 710 μm and short sides with a length of not larger than two-thirds (more preferably not larger than a half) of 710 μm to prepare water absorbent resin powder (ii').

As described above, an operation may be carried out for further removing flat-shaped particles contained among particles that have passed through a sieve corresponding to the sieve (a) above. The long sides of the mesh openings of the sieve (b) simply need to be long enough to remove flat-shaped particles contained in the water-absorbing resin powder (i). The length of the long sides thus simply needs to be not smaller than the length of the sides of the mesh openings of the sieve (c), which is a sieve for use in defining the upper limit value of the particle sizes of the water-absorbing resin powder (i). The length of the short sides of the mesh openings of the sieve (b) is, in order to keep particles each having a spherical shape or a shape similar to a cube and remove only more flat-shaped particles, preferably not larger than two-thirds, more preferably not larger than a half, of the length of the long sides.

A production method in accordance with Embodiment 1 makes it possible to produce a water-absorbing resin powder from which flat-shaped particles have been significantly removed as described above. The production method thus makes it possible to produce a water-absorbing resin powder in accordance with the present invention that is highly elastic and has a high water absorption speed, as demonstrated in Example 1 described later. Example 1 prepared a water-absorbing resin powder (1), from which flake-shaped particles (flake-shaped particles) had been removed (such flat-shaped particles were contained in a comparative water-absorbing resin powder (1)). The water-absorbing resin powder (1) clearly exhibited an elastic modulus index superior to that of the comparative water-absorbing resin powder (1).

(4-2) Embodiment 2

A method in accordance with Embodiment 2 for producing a water-absorbing resin powder is as follows:

A method in accordance with the present invention for producing a water-absorbing resin powder, the method including:

a polymerization step of polymerizing an acrylic acid (salt)-based aqueous monomer solution;

a gel-crushing step of gel-crushing a crosslinked hydrogel polymer during or after the polymerization; and a drying step of drying the crosslinked hydrogel polymer after the gel-crushing, in the gel-crushing step, a gel-crushing device (A) below being used to crush a crosslinked hydrogel polymer containing a resin solid content in an amount of 10 weight % to 80 weight %, (A) a gel-crushing device configured to produce a water-absorbing resin powder, the gel-crushing device including a screw, a feed opening, an extrusion opening, a porous plate, and a barrel, the barrel including a return preventing member on an inner surface thereof, the barrel satisfying (a) and (b) below, where YH is the height of the return preventing member that is found in a case where the barrel has been cut in a direction perpendicular to a direction in which gel of a water-absorbing resin is extruded; YF is the width of an upper surface of the return preventing member that is along a direction perpendicular to a direction in which the return preventing member extends; and N is the diameter of the inside of the barrel that does not include the return preventing member, the screw including a rotating shaft being the center of rotation of the screw and a flight spirally provided on the rotating shaft, the screw satisfying (c) and (d) below, where B is a cross-sectional area of the rotating shaft that is found in a case where the screw has been cut in a direction perpendicular to a direction in which the gel of the water-absorbing resin is extruded; A is a cross-sectional area of a rotating part of the flight; and F is the width of the flight that is along a direction perpendicular to a direction in which the flight extends, (a) $0.05 \leq YH/N \leq 0.2$
(b) $0.05 \leq YF/N \leq 0.2$
(c) $0.540 \leq B/A \leq 0.630$
(d) $0.07 < F/N \leq 0.13$ As a result of diligent research, the inventors of the present invention have discovered that a water-absorbing resin powder in accordance with the present invention can be easily prepared by crushing hydrogel in such a manner as to knead the hydrogel with use of a gel-crushing device having a particular device shape in a gel-crushing step (which is a step included in the process of producing a water-absorbing resin), and have discovered that the above technique can improve the liquid permeability of, preferably both the liquid permeability and the water absorption speed of, a water-absorbing resin powder to be produced.

A gel-crushing device for use in Embodiment 2 is a device for use to obtain a crosslinked hydrogel polymer having a desired shape (herein referred to as "particulate hydrogel") by grain-refining a crosslinked hydrogel polymer that is being polymerized or has been polymerized.

(Configuration of Gel-Crushing Device)

Figure 6:
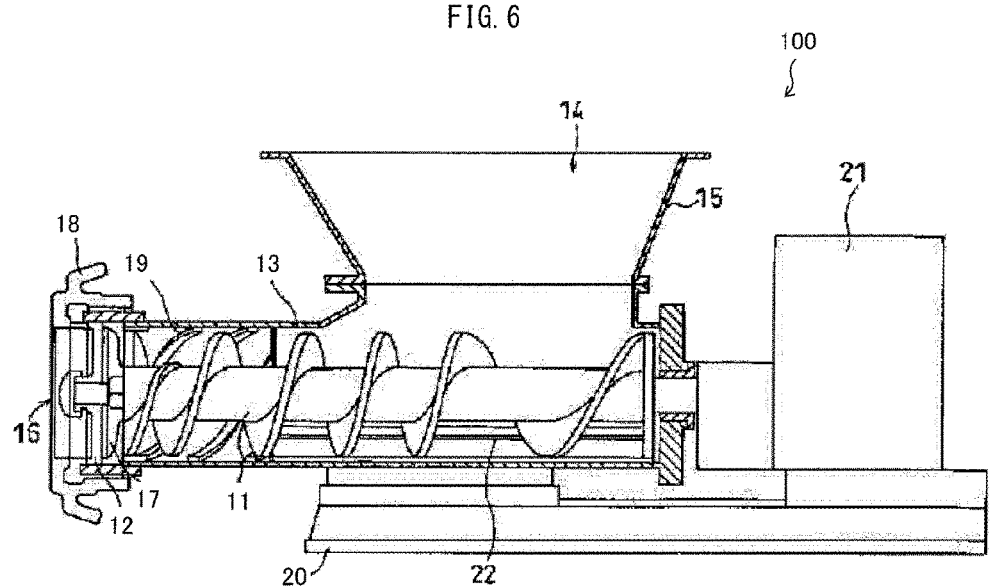
FIG. 6 is a cross-sectional view schematically illustrating an overall configuration of a gel-crushing device for use in the present embodiment.

FIG. 6 is a cross-sectional view schematically illustrating an overall configuration of a gel-crushing device 100 for use in Embodiment 2. The gel-crushing device 100 is used to obtain a particulate hydrogel having a desired shape, and corresponds to the gel-crushing device (A) above. The gel-crushing device 100 is used particularly in a gel-crushing step, which is carried out between a polymerization step and a drying step, during production of a water-absorbing resin.

As illustrated in FIG. 6, the gel-crushing device 100 includes a screw 11, a porous plate 12, a barrel 13, a feed opening 14, a hopper 15, an extrusion opening 16, a rotary blade 17, a ring 18, a return preventing member 19, a base 20, and a motor 21.

According to the gel-crushing device 100, the screw 11 is provided inside of the barrel 13, which has a cylindrical shape. The barrel 13 has one end at which the extrusion opening 16 via which to extrude hydrogel and subject the hydrogel to gel-crushing is provided and the porous plate 12 is placed upstream of the extrusion opening 16 with respect to a direction in which the hydrogel is extruded. The barrel 13 has the other end at which the motor 21 which rotates the screw 11, a driving system, and the like is provided. The base 20, which lies under the barrel 13, makes it possible to stably place a screw extruder. Meanwhile, above the barrel 13, the feed opening 14 via which to feed hydrogel is provided, and the hopper 15 is provided so as to facilitate the feed of the hydrogel.

The gel-crushing device 100 preferably maintains its durability even in a case where it is used for not less than 8000 hours per year. Thus, the gel-crushing device 100 is preferably arranged such that connecting parts of members of the gel-crushing device 100 are so attached as to be not easily disconnected from each other even under a motive power.

(Screw 11 and Barrel 13)

Figure 7:
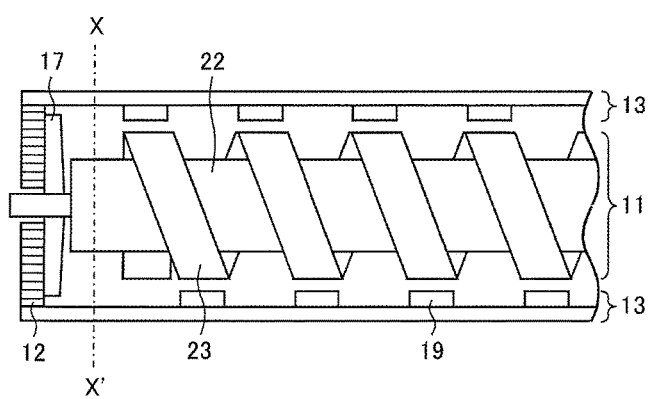
FIG. 7 is a cross-sectional view schematically illustrating the vicinity of an extrusion opening of a gel-crushing device.

FIG. 7 is a cross-sectional view schematically illustrating a vicinity of the extrusion opening 16 of the gel-crushing device 100. The screw 11 mainly includes a rotating shaft 22 and a flight section 23. The flight section 23 is spirally mounted while centering on the rotating shaft 22. The number of windings of the flight section 23 on the rotating shaft 22 refers to the number of times the flight section 23 is wound on the rotating shaft 22 from one end to the other end of the rotating shaft 22. The number of windings of the flight section, that is not particularly limited, is preferably not less than three, especially even more preferably not less than four. Further, the flight section 23 may have a single spiral, a double spiral, or a triple spiral, and the number of flight sections 23 mounted on the rotating shaft 22 is not particularly limited.

The flight section 23 is wound on the rotating shaft 22 in a direction opposite from a direction in which the rotating shaft 22 rotates. That is, in FIG. 6, in a case where the gel-crushing device in accordance with the present invention is seen in a direction from the motor 21 toward the extrusion opening 16, and the rotating shaft 22 rotates clockwise, the flight section 23 is wound counterclockwise on the rotating shaft 22.

The barrel 13 is not particularly limited in shape or size provided that the barrel 13 has a cylindrical inner surface that corresponds to the shape of the screw 11. The barrel 13 is provided with the return preventing member 19. The return preventing member 19 is not particularly limited provided that the return preventing member 19 has a structure that can prevent return of hydrogel. The return preventing member 19 can be a spiral or concentric belt-like protrusion that is provided on an inner wall of the barrel 13, or can be striped, granular, spherical, or angular protrusions that are provided on the inner wall of the barrel 13 so as to be parallel to the screw 11.

The return preventing member 19, which is provided on the inner wall of the barrel 13, yields an effect of preventing return of hydrogel. "The return preventing member 19 is parallel to the screw 11" herein only needs to mean that the return preventing member 19 is substantially parallel to the screw 11. That is, from an inlet toward an outlet of the gel-crushing device, the screw 11 side surface of the return preventing member 19 and the barrel 13 side surface of the flight section 23 of the screw 11 form an angle falling within a range of preferably 0° to 10°, more preferably 0° to 5°, even more preferably 0°.

In a case where the return preventing member 19 is spirally provided inside of the barrel 13, the return preventing member 19 is provided in the barrel 13 in a direction identical to a direction in which the rotating shaft 22 rotates. That is, in FIG. 6, in a case where the gel-crushing device is seen in a direction from the motor 21 toward the extrusion opening 16, and the rotating shaft 22 rotates clockwise, the return preventing member 19 is formed clockwise in the barrel.

In a case where the return preventing member 19 is spirally provided inside of the barrel 13, the number of windings of the return preventing member 19 from the feed opening 14 to the extrusion opening 16 is herein referred to as "barrel thread number". The barrel thread number of the present invention preferably ranges from 1 to 16, more preferably from 1 to 8, even more preferably from 1 to 7, most preferably from 1 to 4. In a case where the barrel thread number of the present invention is more than 16, a gap between barrels is clogged with gel, which resides in the gap and may deteriorate.

Further, the "protrusion", which is the shape of the return preventing member 19, is not limited to a protruding shape, and also encompasses a recessed shape (surrounding protruding shape members that form the recessed shape) obtained in a case where a groove is formed in the barrel 13 for convenience of production.

Figure 8:
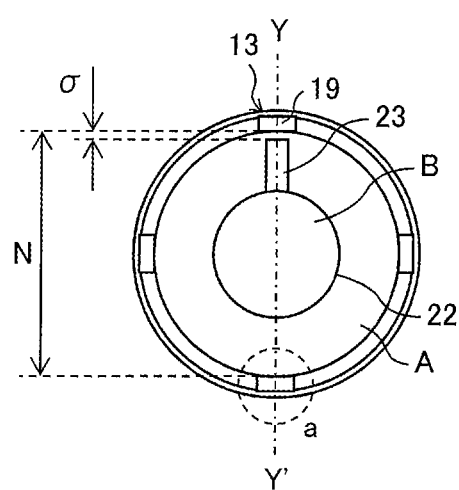
FIG. 8 is a diagram of a screw as cut along the plane X-X' in FIG. 7, and is a cross-sectional view of a screw and a barrel which have been cut in a direction perpendicular to a direction in which hydrogel is extruded.

FIG. 8, which is found in a case where a screw has been cut along X-X' in FIG. 7, is a cross-sectional view of the screw 11 and the barrel 13 which have been cut in a direction perpendicular to a direction in which hydrogel is extruded. FIG. 8 shows "N" to indicate the maximum inner diameter with which contact is prevented between the return preventing member 19 and the screw 11 which is provided inside of the barrel 13 (herein also referred to as "inner diameter N"), "A" to indicate the area of a surface whose inner diameter is N (herein also referred to as "cross-sectional area A"), and "B" to indicate the area of a surface constituted by the rotating shaft 22 and the flight section 23 (herein also referred to as "cross-sectional area B"). The rotating shaft 22 has a diameter of preferably 25 mm to 400 mm, more preferably 40 mm to 300 mm. Further, a "screw cross-sectional area ratio", which herein refers to the ratio of the cross-sectional area B to the cross-sectional area A, is expressed as "B/A".

The gel-crushing device for use in Embodiment 2 is arranged such that the screw cross-sectional area ratio B/A preferably ranges from 0.540 to 0.630. A B/A value within the above range is preferable because it increases the fluid retention capacity under pressure of a water-absorbing resin to be produced.

Assume that the gap between the return preventing member 19 which is provided inside of the barrel 13 and the flight section 23 is σ (herein also referred to as "clearance σ"). The clearance σ is preferably 0.5 mm to 7 mm, more preferably 1 mm to 5 mm, even more preferably 1 mm to 3 mm. In a case where the clearance σ is smaller than 0.5 mm, there will be a higher risk that the screw and the barrel come into contact with each other during the gel-crushing. In a case where the clearance σ is larger than 7 mm, gel is not sufficiently sheared, so that no water-absorbing resin that has intended performance may be obtained.

Figure 9:
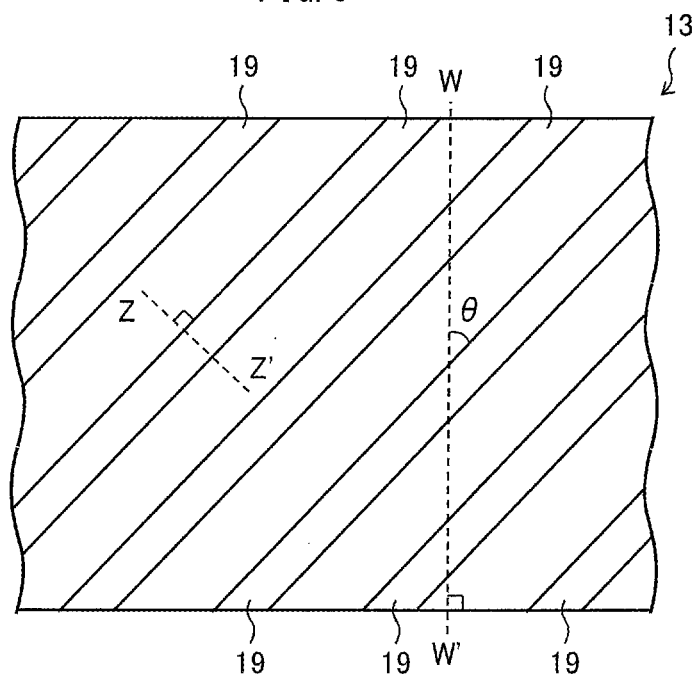
FIG. 9 is a diagram of planar development of the barrel after the screw is cut along the plane Y-Y' in FIG. 8.

Next, the configuration of the barrel 13 is further described with reference to FIGS. 9 to 11. FIG. 9 is a diagram of planar development of the barrel after the screw is cut along the plane Y-Y' in FIG. 8. The plane W-W' in FIG. 9 is perpendicular to the plane Y-Y' in FIG. 8. In a case where the return preventing member 19 is spirally provided inside of the barrel 13, the return preventing member 19 is preferably provided so as to be at an angle of θ with respect to the plane W-W' (see FIG. 9). The angle θ is herein referred to as "barrel set angle".

The barrel set angle θ of the present invention ranges preferably from 10° to 90°, more preferably from 20° to 60°, even more preferably from 30° to 45°. In a case where θ is smaller than 10°, the effect of preventing return of gel is too strong, so that an insufficient shearing force may be applied to the gel. In a case where θ is larger than 90°, no effect of preventing return of gel may be exhibited.

Figure 10:
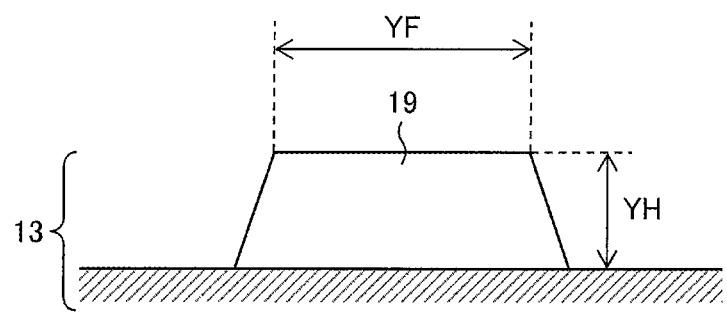
FIG. 10 is a diagram as a result of the barrel being cut along the plane Z-Z' in FIG. 9 and a single return preventing member being enlarged, and is a cross-sectional view schematically illustrating two flight sections.

FIG. 10, which is a diagram as a result of the barrel being cut along the plane Z-Z' in FIG. 9 and a single return preventing member 19 being enlarged, is a cross-sectional view schematically illustrating two flight sections 23. The term "barrel ridge height (YH)" herein refers to the distance from the inner surface of the barrel 13 to the upper surface of the protruding return preventing member 19. The barrel ridge height YH, whose optimum value varies depending on the inner diameter N, ranges preferably from 4 mm to 40 mm, more preferably from 7 mm to 30 mm.

The barrel ridge height YH has a value (YH/N) of preferably 0.05 to 0.2 with respect to the inner diameter N. A YH/N value of 0.05 to 0.2 is preferable because it allows water-absorbing resin to be kneaded sufficiently.

The term "barrel ridge width YF" herein refers to the width of a surface of the return preventing member 19 that is the closest to the screw 11, the width being along a direction perpendicular to the direction in which the return preventing member 19 extends.

The barrel ridge width YF, whose optimum value varies depending on the inner diameter N, ranges preferably from 4 mm to 40 mm, more preferably from 8 mm to 30 mm. The barrel ridge width YF has a value (YF/N) of preferably 0.05 to 0.2 with respect to the inner diameter N. A YF/N value of 0.05 to 0.2 is preferable because it allows water-absorbing resin to be kneaded sufficiently.

Next, the width of a top surface of the flight section 23 that is not in contact with the rotating shaft 22, the width being along a direction perpendicular to a direction in which the flight section 23 extends, is F (herein also referred to as "flight width F"). The flight width has a value (F/N) of preferably 0.07 to 0.13 with respect to the inner diameter N.

An F/N value within the above range is preferable because it ensures a moderate area in which gel is kneaded in the gap between the screw and the barrel protrusion and allows the gel to be sheared sufficiently, which makes it more likely to achieve intended performance. Further, a F/N value within the above range is preferable because it increases the fluid retention capacity under pressure of a water-absorbing resin to be produced.

Figure 11:
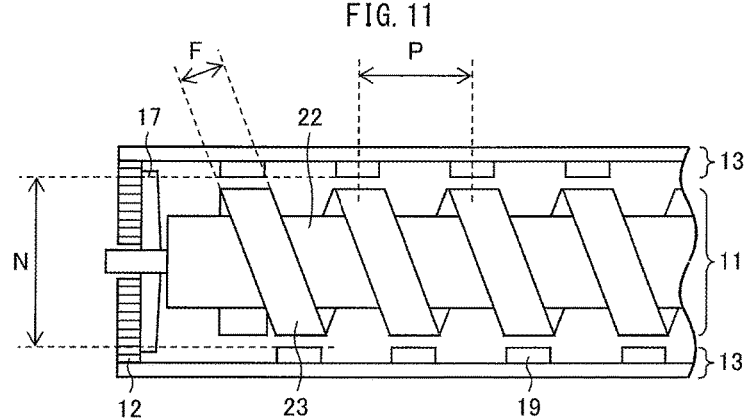
FIG. 11 is a cross-sectional view schematically illustrating the inner diameter N of a barrel, the flight width F of a screw, and a pitch length P.

Further, in FIG. 11, the distance between the respective centers of any adjacent flight widths F is P (herein also referred to as "pitch length P"). FIG. 11 is a cross-sectional view schematically illustrating the inner diameter N of a barrel, the flight width F of a screw, and a pitch length P. The pitch length P (which is equivalent to one flight winding from an end of the screw on the outlet side of the gel-crusher) with respect to the inner diameter N has a value (P/N) of preferably 0.15 to 0.68, more preferably 0.20 to 0.50, even more preferably 0.25 to 0.40. Further, in a case where a single screw has a plurality of pitch lengths, preferably any one of the plurality of pitch lengths falls within the above range, more preferably the pitch length of either one of the first winding and the second winding falls within the above range, most preferably the pitch length of the first winding falls within the above range.

In order to improve the physical properties of a water-absorbing resin powder in accordance with the present invention that is prepared with use of the gel-crushing device for use in Embodiment 2, the above YH/N, YF/N, B/A, and F/N preferably meet the respective requirements (a) to (d) above. Using a gel-crushing device that meets the above requirements facilitates producing a water-absorbing resin powder in accordance with the present invention that is highly elastic and has a high water absorption speed and an excellent diffusion absorbency property.

The respective materials of which the screw 11 and the barrel 13 are made are not particularly limited. The materials are each preferably stainless steel, even more preferably austenitic stainless steel, from the viewpoint of corrosion resistance. Specifically, the screw 11 and the barrel 13 are preferably made of SUS304.

Figure 12:
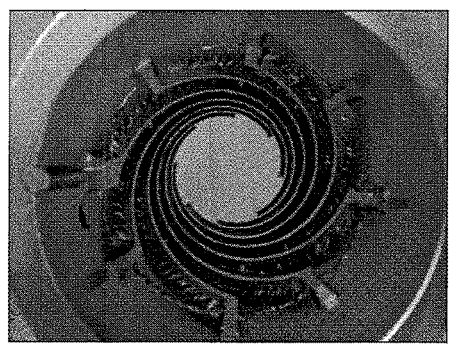
FIG. 12 shows an example of a barrel that can be used in a gel-crushing device for use in embodiments.

FIG. 12 shows an example of a barrel that can be used in the gel-crushing device for use in Embodiment 2. FIG. 12 is a view in which the barrel is seen in a direction from the extrusion opening 16 (shown in FIG. 6) toward the motor 21 (shown in FIG. 6), and is a view of barrel No. B88-874 used in the Examples.

(Porous Plate 12)

The porous plate 12 is a member that is provided in an outlet part of the gel-crushing device for use in Embodiment 2 via which to extrude hydrogel in the barrel 13. The thickness and the pore diameter or the aperture ratio of the porous plate 12 can be appropriately selected according to, for example, a processing amount per unit time of the gel-crushing device or the shape of hydrogel, and is not particularly limited. The porous plate has a thickness (herein also referred to as "die thickness") of preferably 3.5 mm to 40 mm, more preferably 8 mm to 30 mm, even more preferably 10 mm to 25 mm. Further, the porous plate has a pore diameter (herein also referred to as "die pore diameter") of preferably 3.2 mm to 30 mm, more preferably 7.5 mm to 25 mm. In addition, the porous plate has an aperture ratio (herein also referred to as "die aperture ratio") of preferably 20% to 80%, more preferably 30% to 55%.

In a case where a plurality of porous plates that differ in die pore diameter (mm) is used, a simple average value of the respective pore diameters of the plurality of porous plates is set as a pore diameter of the porous plate of the gel-crushing device. The pores of the porous plate, each of which preferably has a circular shape, are not particularly limited. In a case where the pores each have a shape different from a circular shape (for example, a quadrangular shape, an elliptical shape, a slit shape, or the like), the pore diameter (mm) is obtained by converting the aperture area of the pores having the shape different from the circular shape into the aperture area of the pores having the circular shape.

In a case where the porous plate falls under at least one of the following cases: a case where "the porous plate has a die thickness of less than 3.5 mm", a case where "the porous plate has a die pore diameter of more than 30 mm"; and a case where "the porous plate has a die aperture ratio of more than 80%", it may be impossible to apply a sufficient shearing force and a sufficient compressive force to hydrogel. Contrary to this, in a case where the porous plate falls under at least one of the following cases: a case where "the porous plate has a die thickness of more than 40 mm", a case where "the porous plate has a die pore diameter of less than 3.2 mm"; and a case where "the porous plate has a die aperture ratio of less than 20%", an excessive shearing force and an excessive compressive force may be applied to hydrogel, so that a water-absorbing resin may deteriorate in physical property. Thus, it is not preferable that the porous plate fall under at least one of the above cases.

The porous plate 12 is preferably made of a material (metal) that is different from a material (metal) of which the screw 11 and the barrel 13 are made. In a case where the porous plate 12 and the screw 11 and the barrel 13 are made of a single material, the device may break due to, for example, seizing. More specifically, the porous plate 12 is preferably made of a metal that allows the porous plate 12 to have a higher hardness by quenching (a heat treatment). The barrel 13 is preferably made of austenitic stainless steel.

(Materials for Rotating Shaft 22 and Bearing Section)

The gel-crushing device for use in Embodiment 2 can include a bearing section. The "bearing section" herein refers to a member that is provided in a space between a plate of a die and the rotating shaft. A part at which the rotating shaft 22 and the bearing section come into contact with each other and the rotating shaft and the bearing section are preferably made of respective different materials, more preferably respective metals that differ in material. In a case where the part at which the rotating shaft 22 and the bearing section come into contact with each other and the rotating shaft 22 and the bearing section are made of a single material, the device may break due to, for example, seizing, and/or metal powder may contaminate a product.

(Rotation Rate of Rotating Shaft 22 and Peripheral Rotation Speed of Flight Section 23)

The rotation rate of the rotating shaft 22 cannot be generally defined. This is because the peripheral rotation speed of the rotational blade varies depending on the inner diameter of the barrel 13. Note, however, that the rotating shaft 22 has a rotation rate of preferably 60 rpm to 500 rpm, more preferably 80 rpm to 400 rpm, even more preferably 100 rpm to 200 rpm. The rotating shaft 22 which has a rotation rate of less than 60 rpm may fail to apply a shearing force and a compressive force each required for gel-crushing. Meanwhile, the rotating shaft 22 which has a rotation rate of more than 500 rpm will apply an excessive shearing force and an excessive compressive force to hydrogel. This may cause a deterioration in physical property of a water-absorbing resin to be obtained, and/or increase a load on the gel-crushing device in accordance with Embodiment 2, and consequently break the gel-crushing device.

(Operating Temperature of Gel-Crushing Device)

The gel-crushing device 100 for use in Embodiment 2 operates at a temperature of preferably 40° C. to 120° C., more preferably 60° C. to 100° C., so as to prevent, for example, adhesion thereto of hydrogel. Further, the gel-crushing device 100 for use in Embodiment 2 preferably includes, for example, a heater and/or a thermoregulator.

(Temperature of Hydrogel to be Subjected to Gel-Crushing by Gel-Crushing Device)

Hydrogel that has not been subjected to gel-crushing and is to be fed to the gel-crushing device for use in Embodiment 2 has a temperature (herein also referred to as a "gel temperature") of preferably 40° C. to 120° C., more preferably 60° C. to 120° C., even more preferably 60° C. to 110° C., especially even more preferably 65° C. to 110° C., from the viewpoint of particle size control and physical properties.

Hydrogel that has a gel temperature of lower than 40° C. will cause an increase in hardness and elasticity of the resulting hydrogel due to the properties of the hydrogel. This may make it difficult to control the particle shape and the particle size distribution during the gel-crushing. Meanwhile, hydrogel that has a gel temperature of higher than 120° C. will cause an increase in softness of the resulting hydrogel. This may make it difficult to control the particle shape and the particle size distribution. The gel temperature can be appropriately controlled by, for example, adjusting the temperature during polymerization, or heating, heat retention, or cooling after the polymerization.

(Hydrogel Processing Amount)

The processing amount per unit time of the gel-crushing device for use in Embodiment 2 is a value depending on the inner diameter N and varies in preferable range. The processing amount per unit time of the gel-crushing device for use in Embodiment 2 can be expressed as a processing amount-to-inner diameter ratio $T/N^3$ (unit; $g/hr/mm^3$) where T is the amount of hydrogel that the gel-crushing device for use in Embodiment 2 processes per hour (unit; g/hr) and $N^3$ is the value obtained by cubing the inner diameter N (unit; $mm^3$).

The processing amount-to-inner diameter ratio ($T/N^3$) has an upper limit of preferably not more than 2.0, more preferably not more than 1.5, even more preferably not more than 1.0. In a case where the processing amount-to-inner diameter ratio ($T/N^3$) has an upper limit of more than 2.0, hydrogel will not be sufficiently sheared, so that no intended performance of a water absorbent resin may be obtained.

The processing amount-to-inner diameter ratio ($T/N^3$) has a lower limit of preferably not less than 0.05, more preferably not less than 0.10, even more preferably not less than 0.15. In a case where the processing amount-to-inner diameter ratio ($T/N^3$) has a lower limit of less than 0.05, the processing amount will be too small, so that hydrogel will reside in the gel-crushing device. This may cause the hydrogel to be excessively sheared and/or cause a deterioration in gel.

(Use of Water)

The gel-crushing device 100 for use in Embodiment 2 can carry out gel-crushing with respect to hydrogel to which water has been added. The "water" to be added for the present invention can be in the form of a solid, a liquid, or a gas. From the viewpoint of handleability, the water is preferably in the form of a liquid or a gas, or in the form of a mixture of a liquid and a gas.

How and when to add water is not particularly limited provided that the water is fed to the gel-crushing device 100 in which hydrogel resides. Alternatively, hydrogel to which water has been added in advance can be introduced into the gel-crushing device 100. Further, it is possible not only to add the "water" alone but also to add, in combination, the "water" and another additive (such as a surfactant, a base for neutralization, a crosslinking agent, or an inorganic salt) or a solvent different from water. In a case where the "water" and another additive or a solvent different from water are added in combination, the resulting solution has a water content of preferably 90 weight % to 100 weight %, more preferably 99 weight % to 100 weight %, even more preferably substantially 100 weight %.

During the addition of the water, the water is fed in an amount of preferably 0 parts by weight to 4 parts by weight, more preferably 0 parts by weight to 2 parts by weight, per 100 parts by weight of hydrogel. In a case where the water is fed in an amount exceeding 4 parts by weight, a problem such as production of an undried hydrogel during drying may occur.

The water that is fed in the form of a liquid has a temperature of preferably 10° C. to 100° C., more preferably 40° C. to 100° C. Meanwhile, the water that is fed in the form of a gas has a temperature of preferably 100° C. to 220° C., more preferably 100° C. to 160° C., even more preferably 100° C. to 130° C.

The method for preparing the water that is fed in the form of a gas is exemplified by, but not particularly limited to, for example, a method of using water vapor generated by heating a boiler and a method of using gaseous water generated from a surface of water by vibrating the water by ultrasonic waves. Further, in accordance with the present invention, the water that is fed in the form of a gas is preferably water vapor having a pressure higher than atmospheric pressure, more preferably water vapor generated by a boiler.

(Use of Additive)

As described above, it is preferable to carry out gel-crushing with respect to hydrogel to which water has been added. Further, it is also possible to carry out gel-crushing with respect to hydrogel to/with which not only water but also an additive, a neutralizing agent, or the like is added/mixed. A water-absorbing resin to be obtained can be modified as well.

Specifically, an aqueous solution containing a basic substance (for example, a 10 weight % to 50 weight % aqueous sodium hydroxide solution) can be added so as to neutralize hydrogel during the gel-crushing. Alternatively, water-absorbing resin fine powder (0.1 weight % to 30 weight % of water-absorbing resin fine powder per the resin solid content) can be added so that fine powder recycling is carried out. Further, 0.001 weight % to 3 weight % of a polymerization initiator, a reducing agent, or a chelating agent (per the resin solid content) can be added to and mixed with hydrogel during the gel-crushing so as to reduce residual monomers, improve coloring, and impart durability.

(Gel-Grinding Energy (GGE)/Gel-Grinding Energy (2) (GGE2))

According to a method in accordance with the present invention for producing a water-absorbing resin powder, gel-grinding energy (GGE) is preferably controlled so as to fall within a predetermined range.

In accordance with the present invention, gel-grinding energy (GGE) with which to carry out gel-crushing with respect to hydrogel has an upper limit value of preferably not more than 100 J/g, more preferably not more than 60 J/g, even more preferably not more than 50 J/g. Meanwhile, the grinding energy (GGE) has a lower limit value of preferably not less than 15 J/g, more preferably not less than 18 J/g, even more preferably not less than 20 J/g.

For example, in accordance with the present invention, the gel-grinding energy (GGE) with which to carry out the gel-crushing with respect to hydrogel is in a range of preferably 15 J/g to 100 J/g, more preferably 18 J/g to 60 J/g, even more preferably 20 J/g to 50 J/g. In a case where the GGE is controlled so as to fall within the above range, it is possible to carry out the gel-crushing with respect to hydrogel while applying a moderate shearing force and a moderate compressive force to the hydrogel. The foregoing gel-grinding energy (GGE) is defined to include an energy during idling of the gel crusher.

According to the gel-crushing device 100 for use in Embodiment 2, gel-grinding energy 2 (GGE2) is preferably controlled so as to fall within a predetermined range. In accordance with the present invention, gel-grinding energy (2) (GGE (2)) with which to carry out gel-crushing with respect to hydrogel has an upper limit value of preferably not more than 40 J/g, more preferably not more than 32 J/g, even more preferably not more than 25 J/g. Meanwhile, the grinding energy (2) (GGE (2)) has a lower limit value of preferably not less than 7 J/g, more preferably not less than 8 J/g, even more preferably not less than 10 J/g, especially even more preferably not less than 12 J/g.

For example, in accordance with the present invention, the gel-grinding energy (2) (GGE(2)) with which to carry out the gel-crushing with respect to hydrogel is in a range of preferably 7 J/g to 40 J/g, more preferably 8 J/g to 32 J/g, even more preferably 10 J/g to 25 J/g. In a case where the GGE is controlled so as to fall within the above range, it is possible to carry out the gel-crushing with respect to hydrogel while applying a moderate shearing force and a moderate compressive force to the hydrogel, and makes it possible to maximally produce the effect based on the shape of the gel-crushing device for use in Embodiment 2.

In a case where gel-crushing is carried out by use of a plurality of devices, for example, in a case where the gel-crushing device 100 for use in Embodiment 2 is used after kneader polymerization, or in a case where a plurality of gel-crushing devices are used, the sum of amounts of energy consumed in the respective devices is set as the gel-grinding energy (2) (GGE (2)).

Using the gel-crushing device 100 for use in Embodiment 2 makes it possible to produce a water-absorbing resin powder in accordance with the present invention that is highly elastic, has a high water absorption speed, and consequently has an excellent diffusion absorbency property as demonstrated in the Examples below. This is presumably because the above device optimizes gel-crushing to allow for production of particles each having a shape similar to a sphere and reduce the number of flat-shaped particles, which would otherwise decrease the elasticity and degrade the performance of a water-absorbing resin.

As described above, either of the respective methods described for Embodiments 1 and 2 makes it possible to produce a water-absorbing resin powder in accordance with the present invention. The method for producing the water-absorbing resin powder is, however, not limited to such methods.

[5] Process for Producing Water-Absorbing Resin Powder (5-1) Polymerization Step The polymerization step is a step of polymerizing an aqueous solution whose main component is acrylic acid (salt) to obtain a crosslinked hydrogel polymer (herein also referred to as "hydrogel").

(Monomer)

A water-absorbing resin powder in accordance with the present invention is produced from a monomer(s) (material) whose main component is acrylic acid (salt). The water-absorbing resin powder is usually polymerized in the form of an aqueous solution. An aqueous solution of a monomer(s) whose main component is acrylic acid (salt) is herein also referred to as "acrylic acid (salt)-based aqueous monomer solution". The monomer concentration in the aqueous monomer solution ranges from preferably 10 weight % to 80 weight %, more preferably 20 weight % to 80 weight %, even more preferably 30 weight % to 70 weight %, especially even more preferably 40 weight % to 60 weight %.

It is preferable, from the viewpoint of water absorption performance and residual monomers, that hydrogel obtained by the polymerization of the aqueous monomer solution have a polymer having an acid group at least part of which is neutralized. A salt resulting from neutralization is not limited to any particular one, but is, from the viewpoint of water absorption performance, preferably a monovalent salt selected from the group consisting of alkali metal salt, ammonium salt, and amine salt, more preferably alkali metal salt, even more preferably alkali metal salt selected from the group consisting of sodium salt, lithium salt, and potassium salt, especially even more preferably sodium salt.

Therefore, a basic substance to be used for such neutralization is not limited to any particular one, but is preferably a monovalent basic substance such as a hydroxide of alkali metal including sodium hydroxide, potassium hydroxide, lithium hydroxide, and the like or a carbonate (hydrogencarbonate) including sodium carbonate (sodium hydrogencarbonate), potassium carbonate (potassium hydrogencarbonate), and the like, especially even more preferably sodium hydroxide.

The neutralization can be carried out in various ways and under various conditions before, during, or after the polymerization. For example, hydrogel obtained by polymerizing acrylic acid in which the acid group is unneutralized or neutralized at a low neutralization rate (for example, 0 mol % to 30 mol % of the acid group is neutralized) can be neutralized, particularly neutralized while being subjected to gel-crushing. It is, however, preferable, from the viewpoint of improvement in, for example, productivity or physical properties, that unpolymerized acrylic acid be neutralized. That is, it is preferable that neutralized acrylic acid (partially neutralized salt of acrylic acid) be used as a monomer.

The neutralization rate of the neutralization is not limited to any particular one, but ranges, with respect to a final product of a water-absorbing resin, from preferably 10 mol % to 100 mol %, more preferably 30 mol % to 95 mol %, even more preferably 45 mol % to 90 mol %, especially even more preferably 60 mol % to 80 mol %. The temperature of the neutralization is not limited to any particular one, but ranges from preferably 10° C. to 100° C., more preferably 30° C. to 90° C. As to other neutralization process conditions, the condition disclosed in European Patent No. 574260 is preferably applied to the present invention. It is preferable that hydrogel whose neutralization rate falls within the above range be subjected to gel-crushing through the use of a gel-crushing device described for Embodiment 2 in a gel-crushing step.

In order to improve physical properties of a water-absorbing resin powder obtainable by the present invention, any component such as water-soluble resin or water-absorbing resin including starch, cellulose, polyvinyl alcohol (PVA), polyacrylic acid (salt), polyethyleneimine, and the like, a foaming agent including a carbonate, an azo compound, an air bubble generating agent, and the like, a surfactant, or an additive can be added to the aqueous monomer solution, the hydrogel, a dried polymer, the water-absorbing resin, or the like in any step of a production process of the present invention.

In a case where the water-soluble resin or the water-absorbing resin is to be added, the amount of the water-soluble resin or the water-absorbing resin to be added ranges from preferably 0 weight % to 50 weight %, more preferably 0 weight % to 20 weight %, even more preferably 0 weight % to 10 weight %, especially even more preferably 0 weight % to 3 weight %, per the monomer. In a case where the foaming agent, the surfactant, or the additive is to be added, the amount of the foaming agent, the surfactant, or the additive to be added ranges from preferably 0 weight % to 5 weight %, more preferably 0 weight % to 1 weight %.

A graft polymer or a water-absorbing resin composition can be obtained through addition of the aqueous solution resin or the water-absorbing resin. A polymer produced from starch and acrylic acid, a polymer produced from PVA and acrylic acid, and the like polymer are also regarded as a polyacrylic acid (salt)-based water-absorbing resin for the present invention.

Further, a chelating agent, an α-hydroxycarboxylic acid compound, or an inorganic reducing agent can be used in order to improve color stability of a water-absorbing resin powder obtainable by the present invention (color stability of a water-absorbing resin powder which has undergone long-term storage under high temperature and high humidity) or urine resistance (prevention of gel deterioration) of a water-absorbing resin powder. Among these, the chelating agent is especially even more preferably used.

The amount of the chelating agent, the α-hydroxycarboxylic acid compound, or the inorganic reducing agent to be used ranges from preferably 10 ppm to 5000 ppm, more preferably 10 ppm to 1000 ppm, even more preferably 50 ppm to 1000 ppm, especially even more preferably 100 ppm to 1000 ppm, per the water-absorbing resin. One of the compounds disclosed in U.S. Pat. No. 6,599,989 and the compound disclosed in International Publication No. 2008/090961 is employed as the chelating agent for the present invention. Among these compounds, an aminocarboxylic acid-based metal chelating agent or a polyvalent phosphoric acid-based compound is preferably used as the chelating agent.

In a case where acrylic acid (salt) is used as a main component for the present invention, a hydrophilic or hydrophobic unsaturated monomer(s) (herein referred to as "other monomer(s)") other than the acrylic acid (salt) can be used in combination with the acrylic acid (salt). Such other monomer(s) is not limited to any particular one. Examples of the other monomer(s) include methacrylic acid, (anhydrous) maleic acid, 2-(meth)acrylamide-2-methylpropanesulfonic acid, (meth)acryloxyalkanesulfonic acid, N-vinyl-2-pyrrolidone, N-vinylacetamide, (meth)acrylamide, N-isopropyl (meth)acrylamide, N,N-dimethyl (meth)acrylamide, 2-hydroxyethyl (meth)acrylate, methoxypolyethyleneglycol (meth)acrylate, polyethyleneglycol (meth)acrylate, stearylacrylate, salts thereof, and the like.

In a case where the other monomer(s) is to be used, the amount of the other monomer(s) used is determined as appropriate so as not to impair water absorption performance of a water-absorbing resin powder to be obtained, and is not limited to any particular one, but ranges from preferably 0 mol % to 50 mol %, more preferably 0 mol % to 30 mol %, even more preferably 0 mol % to 10 mol %, per the total amount of monomers.

(Internal Crosslinking Agent)

In the present invention, it is preferable, from the viewpoint of water absorption performance of a water-absorbing resin powder to be obtained, that a crosslinking agent (herein referred to as "internal crosslinking agent") be used. The internal crosslinking agent is not limited to any particular one. Examples of the internal crosslinking agent include a polymerizable crosslinking agent that is polymerizable with acrylic acid, a reactive crosslinking agent that is reactive with a carboxyl group, a crosslinking agent that is polymerizable with acrylic acid and reactive with a carboxyl group, and the like.

Examples of the polymerizable crosslinking agent include compounds each having at least two polymerizable double bonds in a molecule, such as N,N'-methylene bisacrylamide, (poly)ethylene glycol di(meth)acrylate, (polyoxyethylene) trimethylolpropane tri(meth)acrylate, and poly(meth)allyloxy alkane.

Examples of the reactive crosslinking agent include: covalent bonding crosslinking agents such as a polyglycidyl ether (for example, ethyleneglycoldiglycidyl ether) and a polyvalent alcohol (for example, propanediol, glycerine, and sorbitol); and an ionic bonding crosslinking agent such as a polyvalent metal compound (for example, aluminum salt).

Among these, from the viewpoint of water absorption performance, the internal crosslinking agent is more preferably the polymerizable crosslinking agent that is polymerizable with acrylic acid, especially even more preferably an acrylate-based, allyl-based or acrylamide-based polymerizable crosslinking agent. These internal crosslinking agents can be used singly or in combination of two or more. In a case where the polymerizable crosslinking agent and the covalent bonding crosslinking agent are used in combination, the mixture ratio of the polymerizable crosslinking agent and the covalent bonding crosslinking agent is preferably 10:1 to 1:10.

From the viewpoint of the physical properties, the amount of the internal crosslinking agent to be used ranges from preferably 0.001 mol % to 5 mol %, more preferably 0.002 mol % to 2 mol %, even more preferably 0.04 mol % to 1 mol %, especially even more preferably 0.06 mol % to 0.5 mol %, most preferably 0.07 mol % to 0.2 mol %, per the total amount of monomers excluding a crosslinking agent. Moreover, in a particularly preferable embodiment of the present invention, the polymerizable crosslinking agent is used in an amount ranging from preferably 0.01 mol % to 1 mol %, more preferably 0.04 mol % to 0.5 mol %, even more preferably 0.06 mol % to 0.1 mol %.

(Polymerization Initiator)

A polymerization initiator for use in the present invention is selected appropriately depending on how the polymerization is carried out, and is not limited to any particular one. Examples of the polymerization initiator include photolytic-type polymerization initiators, pyrolysis-type polymerization initiators, redox-type polymerization initiators, and the like.

Examples of the photolytic-type polymerization initiators include benzoin derivatives, benzyl derivatives, acetophenone derivatives, benzophenone derivatives, azo compounds, and the like.

Examples of the pyrolysis-type polymerization initiators include: persulfates such as sodium persulfate, potassium persulfate, and ammonium persulfate; peroxides such as hydrogen peroxide, t-butyl peroxide, and methyl-ethyl-ketone peroxide; azo compounds such as 2,2'-azobis(2-amidinopropane)dihydrochloride, and 2,2'-azobis[2-(2-imidazoline 2-yl) propane]dihydrochloride; and the like.

Examples of the redox-type polymerization initiators include systems each of which is a combination of a reducing compound such as L-ascorbic acid or sodium hydrogen sulfite with any of the persulfates and peroxides.

Further, it is also a preferable embodiment to use any of the photolytic-type polymerization initiators and any of the pyrolysis-type polymerization initiators in combination.

The amount of the polymerization initiator to be used ranges from preferably 0.0001 mol % to 1 mol %, more preferably 0.0005 mol % to 0.5 mol %, per the total amount of monomers. The polymerization initiator used in an amount exceeding 1 mol % may cause a deterioration in color of a water-absorbing resin. Moreover, the polymerization initiator used in an amount of less than 0.0001 mol % is not preferable because it may increase residual monomers.

(Polymerization Method)

In the method in accordance with the present invention for producing a water-absorbing resin powder, the polymerization method to obtain a particulate hydrogel can be spraying droplet polymerization or reversed phase suspension polymerization. However, aqueous solution polymerization is employed from the viewpoint of liquid permeability (SFC) and water absorption speed (FSR) of a water-absorbing resin powder to be obtained, polymerization controllability, and others.

The aqueous solution polymerization can be tank-type (silo-type) unstirring polymerization. However, the aqueous solution polymerization is preferably kneader polymerization or belt polymerization, more preferably continuous aqueous solution polymerization, even more preferably high-concentration continuous aqueous solution polymerization, especially even more preferably high-concentration high-temperature starting continuous aqueous solution polymerization.

Stirring polymerization means polymerizing hydrogel while stirring the hydrogel, particularly polymerizing hydrogel while stirring and grain-refining the hydrogel (wherein the hydrogel is particularly hydrogel having a polymerization rate of not less than 10 mol %, further particularly hydrogel having a polymerization rate of not less than 50 mol %). An aqueous monomer solution (having a polymerization rate of 0 mol % to less than 10 mol %) can be stirred as appropriate before and/or after the unstirring polymerization is carried out.

Examples of the continuous aqueous solution polymerization include continuous kneader polymerization (disclosed in U.S. Pat. Nos. 6,987,171 and 6,710,141, and others), and continuous belt polymerization (disclosed in U.S. Pat. Nos. 4,893,999 and 6,241,928, U.S. Patent Application Publication No. 2005/215734, and others). These aqueous solution polymerizations can produce a water-absorbing resin powder with high productivity.

In the high-concentration continuous aqueous solution polymerization, the monomer concentration (solid content) is preferably not less than 35 weight %, more preferably not less than 40 weight %, even more preferably not less than 45 weight % (but not more than the saturated concentration). In high-temperature starting continuous aqueous solution polymerization, the polymerization starting temperature is preferably not lower than 30° C., more preferably not lower than 35° C., even more preferably not lower than 40° C., especially even more preferably not lower than 50° C. (but not higher than the boiling temperature). The high-concentration high-temperature starting continuous aqueous solution polymerization is a combination of the high-concentration continuous aqueous solution polymerization and the high-temperature starting continuous aqueous solution polymerization.

The high-concentration high-temperature starting continuous aqueous solution polymerization is disclosed in U.S. Pat. Nos. 6,906,159 and 7,091,253, and others. The high-concentration high-temperature starting continuous aqueous solution polymerization is preferable because it can produce a water-absorbing resin powder with a high degree of whiteness and can be easily applied to industrial-scale production.

Therefore, the polymerization method in the production method in accordance with the present invention is suitably applied to a large-scale production apparatus having a great production volume per production line. The production volume is preferably not less than 0.5 t/hr, more preferably not less than 1 t/hr, even more preferably not less than 5 t/hr, especially even more preferably not less than 10 t/hr.

The polymerization can be carried out under air atmosphere. It is, however, preferable from the viewpoint of coloring prevention that the polymerization be carried out under inert gas atmosphere such as water vapor, nitrogen, or argon (with, for example, an oxygen concentration of not more than 1 volume %). It is further preferable that the polymerization be carried out after oxygen dissolved in a monomer(s) or in a solution containing a monomer(s) is substituted (deaerated) with inert gas (by, for example, less than 1 mg/L of oxygen). Such deaeration allows for a monomer(s) having an excellent stability, without causing gelling before polymerization. This makes it possible to provide a water-absorbing resin powder with higher physical properties and a higher degree of whiteness.

The amount of inert gas to be used is preferably 0.005 weight % to 0.2 weight %, more preferably 0.01 weight % to 0.1 weight %, even more preferably 0.015 weight % to 0.5 weight %, per the total amount of monomers. Further, nitrogen is preferably used as the inert gas.

(Surfactant, Dispersant)

In the polymerization step of the present invention, a surfactant and/or a dispersant can be used if necessary. The use of the surfactant and/or the dispersing agent allows gas bubbles to be stably suspended in a water-absorbing resin during the polymerization. Further, by adjusting the type(s) or amount(s) of the surfactant and/or the dispersant as appropriate, it is possible to obtain a water-absorbing resin powder having intended physical properties. It is preferable that the surfactant be a non-polymeric surfactant, while the dispersant is a polymeric dispersant. Further, it is preferable that the surfactant and/or the dispersant be added before the aqueous monomer solution prior to or during polymerization reaches a temperature of not lower than 50° C.

The amount of the surfactant and/or the dispersant to be used can be determined as appropriate according to the type(s) of the surfactant and/or the dispersing agent. The use of the surfactant and/or the dispersant changes the surface tension of a water-absorbing resin powder to be obtained. Thus, the amount of the surfactant and/or the dispersant to be used is determined so that the surface tension of the water-absorbing resin powder to be obtained is preferably not less than 69 mN/m, more preferably not less than 70 mN/m, even more preferably not less than 71 mN/m. Suitable kind and amount of the surfactant used are as described above in [2-8].

(5-2) Gel-Crushing Step

The gel-crushing step is a step of grain-refining the above-described crosslinked hydrogel polymer during or after polymerization to obtain a particulate crosslinked hydrogel polymer. The operation carried out in this step is called "gel-crushing" as distinguished from "pulverization" in "(5-4) Pulverization step and classification step" below.

The method described above for Embodiment 1 is not intended to control the particle shape during the gel-crushing step. Thus, this step does not require the use of the gel-crushing device described for Embodiment 2. In a case where the method described for Embodiment 1 is used, the gel-crushing step may simply need to use a conventionally publicly known meat chopper or the like.

The method described for Embodiment 2 is arranged such that the gel-crushing device used in the gel-crushing step is the gel-crushing device described for Embodiment 2. The configuration, temperatures, and operation conditions of the gel-crushing device are as described for Embodiment 2.

(5-3) Drying Step

The drying step is a step of drying the particulate hydrogel obtained in the gel-crushing step to obtain a dried polymer. The following description will discuss a drying method suitably applicable to the present invention.

Examples of the drying method in the drying step of the present invention include various methods such as thermal drying, hot air drying, drying under reduced pressure, infrared drying, microwave drying, drying by use of a drum dryer, drying by azeotropic dehydration with a hydrophobic organic solvent, and high humidity drying by use of high temperature water vapor. Among the drying methods, the hot air drying is preferable. Particularly, hot air drying with a dew point of 40° C. to 100° C., more preferably a dew point of 50° C. to 90° C., is suitably adopted.

As a method of drying the particulate hydrogel for the present invention, a through-flow dryer is preferably used, and a through-flow belt hot air dryer is further preferably used. In a case where the through-flow belt hot air dryer is used, the through-flow belt hot air dryer is required to send hot air to a hydrogel layer, provided on a through-flow belt and allowed to stand still, from a direction perpendicular to the hydrogel layer (for example, from both above and below the hydrogel layer, from below the hydrogel layer, or from above the hydrogel layer). In a case where the through-flow belt-type dryer is not used or in a case where hot air is not sent from the direction perpendicular to the hydrogel layer, it will be impossible to uniformly dry the hydrogel layer. This may deteriorate physical properties (e.g. liquid permeability) of a water-absorbing resin powder to be obtained.

The "direction perpendicular to the hydrogel layer" is a state in which hot air flows through a gel layer (a layer of particulate hydrogel having a thickness in a range of 10 mm to 300 mm and laminated on a punching metal or a woven metallic wire) in a direction perpendicular to the gel layer (from above the gel layer to below the gel layer, or from below the gel layer to above the gel layer). The direction perpendicular to the gel layer is not limited to a completely perpendicular direction as long as hot air flows through the gel layer in an up-and-down direction. Therefore, hot air can be sent from an oblique direction, for example, hot air is sent from a direction preferably within 30 degrees, more preferably within 20 degrees, even more preferably within 10 degrees, especially even more preferably within 5 degrees, most preferably 0°, from the perpendicular direction.

The following description will discuss drying conditions and others of the drying step of the present invention.

(Drying Temperature)

The drying temperature in the drying step (preferably in the through-flow belt-type dryer) of the present invention ranges from preferably 100° C. to 300° C., more preferably 150° C. to 250° C., even more preferably 160° C. to 220° C., especially even more preferably 170° C. to 200° C.

A drying temperature ranging from 100° C. to 300° C. makes it possible to reduce both a drying time and coloring of a dried polymer to be obtained. Further, such a drying temperature tends to improve the liquid permeability, preferably both the liquid permeability and water absorption speed, of a water-absorbing resin powder to be obtained. Meanwhile, a drying temperature of higher than 300° C. will affect a polymer chain, thus deteriorating the physical properties of a water-absorbing resin powder to be obtained. Moreover, a drying temperature of lower than 100° C. will generate undried particulate hydrogel and cause clogging during a subsequent pulverization step, without changing the water absorption speed.

(Drying Time)

The drying time in the drying step (preferably by use of the through-flow belt-type dryer) of the present invention depends on the surface area of the particulate hydrogel, type of the dryer, and the like, and only needs to be appropriately determined so that an objective moisture content is attained. However, the drying time ranges from preferably 1 minute to 10 hours, more preferably 5 minutes to 2 hours, even more preferably 10 minutes to 1 hour, especially even more preferably 15 minutes to 45 minutes.

The period of time that elapses before the particulate hydrogel discharged from the gel-crushing step described in (5-2) above is subjected to the drying step, that is, the period of time of moving of the particulate hydrogel from the outlet of the gel-crushing device to the inlet of the dryer, is preferably as short as possible from the viewpoint of coloring of a water-absorbing resin powder. Specifically, the period of time is preferably within 2 hours, more preferably within 1 hour, even more preferably within 30 minutes, especially even more preferably within 10 minutes, most preferably within 2 minutes.

(Air Velocity)

In the drying step of the present invention, in order to further attain the object of the present invention, the through-flow dryer, especially the belt-type dryer, sends hot air in the vertical direction (an up-and-down direction) at an air velocity of preferably 0.8 m/s to 2.5 m/s, more preferably 1.0 m/s to 2.0 m/s. The air velocity in the above range makes it possible not only to control the moisture content of the dried polymer to be obtained to be in an intended range, but also to improve the water absorption speed. An air velocity of less than 0.8 m/s will result in elongation of the drying time. This may deteriorate the liquid permeability and water absorption speed of a water-absorbing resin powder to be obtained. An air velocity of more than 2.5 m/s will cause the particulate hydrogel to be blown up during drying. This may make it difficult to stably dry the particulate hydrogel.

The air velocity only needs to be controlled so as not to impair the effect of the present invention, and therefore the air velocity only needs to be controlled as described above during, for example, preferably 70% or more, more preferably 90% or more, even more preferably 95% or more, of the drying time. Note also that in a case of the through-flow belt-type dryer, the air velocity is represented by an average flow rate of hot air passing in a direction perpendicular to the surface of the through-flow belt that horizontally moves. Therefore, the average flow rate of hot air is calculated by dividing, by the area of the through-flow belt, the quantity of hot air sent to the through-flow belt dryer.

(Dew Point of Hot Air)

The hot air used by the through-flow belt-type dryer in the drying step of the present invention contains at least water vapor, and has a dew point of preferably 30° C. to 100° C., more preferably 30° C. to 80° C. Controlling the dew point of hot air in the above range or even more preferably the gel particle diameter in the above range makes it possible to reduce residual monomers and further prevent reduction in the bulk specific gravity of the dried polymer. The dew point is a value as of a point in time when the particulate hydrogel has a moisture content of at least 10 weight % or more, preferably 20 weight % or more.

Further, in the drying step of the present invention, it is preferable that the dew point in the vicinity of the inlet of the dryer (or in the early period of drying, for example, at or before timing of 50% of the drying time) be higher than the dew point in the vicinity of the outlet of the dryer (or in the last period of the drying, for example, at or after timing of 50% of the drying time) from the viewpoint of, for example, residual monomers, water absorption performance, and coloring. Specifically, it is preferable to expose the particulate hydrogel to hot air having a dew point higher by preferably 10° C. to 50° C., more preferably 15° C. to 40° C., in the vicinity of the inlet of the dryer than in the vicinity of the outlet of the dryer. Controlling the dew point in the above range makes it possible to prevent reduction in the bulk specific gravity of the dried polymer.

The particulate hydrogel obtained in the gel-crushing step is dried in the drying step to be a dried polymer. The resin solid content calculated from an amount lost of the dried polymer (heating 1 g of the powder or particles at 180° C. for three hours) is preferably more than 80 weight %, more preferably in a range of 85 weight % to 99 weight %, even more preferably in a range of 90 weight % to 98 weight %, especially even more preferably in a range of 92 weight % to 97 weight %.

(Surface Temperature of Particulate Hydrogel)

The particulate hydrogel obtained in the gel-crushing step has a surface temperature in a range of preferably 40° C. to 110° C., more preferably 60° C. to 110° C., even more preferably 60° C. to 100° C., especially even more preferably 70° C. to 100° C., immediately before being introduced into the dryer. A surface temperature of lower than 40° C. will generate a balloon-like dried substance during drying and generate plenty of fine powder during pulverization. This may deteriorate the physical properties of the water-absorbing resin. Moreover, a surface temperature of higher than 110° C. of the particulate hydrogel before drying will cause deterioration (such as, for example, an increase of a water-soluble component) or coloring of the water-absorbing resin after drying.

(5-4) Pulverization Step and Classification Step

These steps are steps of pulverizing and classifying the dried polymer obtained in the drying step to obtain water-absorbing resin particles. The pulverization step is different from the gel-crushing step described in (5-2) in terms of resin solid content during pulverization, especially in that the target to be pulverized in the pulverization step has been dried in the drying step (preferably the resin solid content also has been dried). The water-absorbing resin particles obtained after the pulverization step may be referred to as "pulverized substance".

A water-absorbing resin powder in accordance with the present invention needs to be surface-crosslinked as described in (5-5) below. It is thus preferable to control the dried polymer to have particular particle sizes in order to improve the physical properties in the surface crosslinking step. The particle sizes of the dried polymer can be appropriately controlled not only in the pulverization step or the classification step but also in the polymerization step, a fine powder recycling step, a granulation step, or the like step. The particle sizes are defined by a standard sieve (JIS Z8801-1 (2000)) as described above.

A pulverizer that can be used in the pulverization step is not limited to any particular one. Examples of the pulverizer include a vibration mill, a roll granulator, a knuckle-type pulverizer, a roll mill, a high-speed pulverizer (such as a pin mill, a hammer mill, and a screw mill), a cylindrical mixer, and the like. Among these pulverizers, it is preferable to use a multiple-stage roll mill or roll granulator from the viewpoint of particle size control.

The classification step is carried out so that the water-absorbing resin particles have the particle sizes description below. Since a water-absorbing resin powder in accordance with the present invention needs to be surface-crosslinked, it is preferable to carry out the classification step before the surface crosslinking step (first classification step). The classification step can be further carried out after the surface crosslinking step (second classification step).

The way in which the classification step is carried out is not particularly limited. For example, the classification step is carried out by use of a sieve as below. In a case where the particle diameter distribution of the water-absorbing resin particles is set at 150 μm to 850 μm, first, the pulverized substance is sieved by use of a sieve having a mesh size of 850 μm, and then the pulverized substance that has passed through the sieve is further sieved by use of a sieve having a mesh size of 150 μm or a sieve having a mesh size of more than 150 μm (for example, 200 μm). The pulverized substance left on the sieve having the mesh size of, for example, 150 μm is water-absorbing resin particles having an intended particle diameter distribution. The classification step can be carried out not only by sieve classification but also by air classification with use of any of various classifiers.

The classification step described above ensures that water-absorbing resin powder in accordance with the present invention meets the condition that a proportion of the water-absorbing resin powder that has particle sizes of not less than 150 μm to less than 850 μm is not less than 90 weight %.

(5-5) Surface-Crosslinking Step

A water-absorbing resin powder in accordance with the present invention contains a polyacrylic acid (salt)-based water-absorbing resin as a main component and is surface-crosslinked. A surface treatment step for the surface-crosslinking includes a surface crosslinking step carried out with use of a publicly known surface-crosslinking agent by a publicly known surface-crosslinking method, and if necessary, further includes an addition step.

(Covalent Bonding Surface-Crosslinking Agent)

The surface-crosslinking agent for use in the present invention can be exemplified by various organic or inorganic crosslinking agents, but it is preferable that the surface-crosslinking agent be an organic surface-crosslinking agent. In terms of the physical properties, it is preferable to use, as the surface-crosslinking agent, a dehydrative crosslinking agent such as a polyvalent alcohol compound, an epoxy compound, a polyvalent amine compound or a condensed product with a halo epoxy compound of the polyvalent amine compound, an oxazoline compound, a (mono, di, or poly)oxazolidinone compound, or an alkylene carbonate compound. In particular, it is possible to use a dehydrative crosslinking agent such as a polyvalent alcohol compound, an alkylene carbonate compound, or an oxazolidinone compound, which needs to react at a high temperature.

In a case where a dehydrative crosslinking agent is not used, the surface-crosslinking agent is more specifically exemplified by the compounds described in U.S. Pat. Nos. 6,228,930, 6,071,976, 6,254,990, and others. For example, the surface-crosslinking agent is exemplified by polyvalent alcohol compounds such as mono-, di-, tri-, tetra-propylene glycol, 1,3-propanediol, glycerin, 1,4-butanediol, 1,3-butanediol, 1,5-pentanediol, 1,6-hexanediol, and sorbitol; epoxy compounds such as ethylene glycol diglycidyl ether and glycidol; alkylene carbonate compounds such as ethylene carbonate; oxetane compounds; cyclic urea compounds such as 2-imidazolidinone; and others.

The amount of the surface-crosslinking agent to be used is determined as appropriate at approximately preferably 0.001 parts by weight to 10 parts by weight, more preferably 0.01 parts by weight to 5 parts by weight, per 100 parts by weight of the water-absorbing resin particles. In addition to the surface-crosslinking agent, water is preferably used in combination. The amount of the water to be used ranges from preferably 0.5 parts by weight to 20 parts by weight, more preferably 0.5 parts by weight to 10 parts by weight, per 100 parts by weight of the water-absorbing resin particles. In a case where an inorganic surface-crosslinking agent and an organic surface-crosslinking agent are used in combination, the surface-crosslinking agents are each used in an amount ranging from preferably 0.001 parts by weight to 10 parts by weight, more preferably 0.01 parts by weight to 5 parts by weight, per 100 parts by weight of the water-absorbing resin particles.

In this case, a hydrophilic organic solvent may be used in an amount of preferably 0 parts by weight to 10 parts by weight, more preferably 0 parts by weight to 5 parts by weight, per 100 parts by weight of the water-absorbing resin particles. In mixing a crosslinking agent solution with the water-absorbing resin particles, water-insoluble fine particle powder or a surfactant can be added as well in an amount not adversely affecting the effect of the present invention, for example, preferably 0 parts by weight to 10 parts by weight, more preferably 0 parts by weight to 5 parts by weight, further even more preferably 0 parts by weight to 1 part by weight. Examples of a usable surfactant and an amount of the surfactant used are shown in U.S. Pat. No. 7,473,739, etc.

(Mixing)

In mixing the surface-crosslinking agent with the water-absorbing resin particles, a vertical or horizontal high-speed rotation stirring mixer is suitably used. The rotation rate of the mixer is preferably 100 rpm to 10000 rpm, more preferably 300 rpm to 2000 rpm. Further, the residence time for which the water-absorbing resin resides in the mixer is preferably within 180 seconds, more preferably 0.1 seconds to 60 seconds, even more preferably 1 second to 30 seconds.

(Other Surface-Crosslinking Methods)

In the present invention, it is possible to employ, instead of a method in which the surface-crosslinking agent is used, a surface-crosslinking method in which a radical polymerization initiator is used (U.S. Pat. No. 4,783,510, and International Publication No. 2006/062258), or a surface-crosslinking method in which a monomer(s) is polymerized on a surface of water-absorbing resin (U.S. Patent Application Publication Nos. 2005/048221 and 2009/0239966, and International Publication No. 2009/048160).

In the above surface-crosslinking method, a preferable example of the radical polymerization initiator to be used is a persulfate, a preferable example of the monomer(s) to be used if necessary is acrylic acid (salt) or the above-described crosslinking agents, and a preferable example of a solvent to be used is water. The materials are added onto the surface of the water-absorbing resin, and then by an active energy line (particularly ultraviolet ray) or heat, crosslinking polymerization is carried out or a crosslinking reaction by use of the radical polymerization initiator is caused on the surface of the water-absorbing resin. The surface-crosslinking is thus carried out.

(Ionic Bonding Surface-Crosslinking Agent)

A method in accordance with the present invention for producing a polyacrylic acid (salt)-based water-absorbing resin powder may further include an addition step, carried out simultaneously with or separately from the surface-crosslinking step described above, of adding at least one of a multivalent metal salt, a cationic polymer, and inorganic microparticles. That is, the liquid permeability, the water absorption speed, and others can be improved by solely using the inorganic surface-crosslinking agent or by using the inorganic surface-crosslinking agent in combination with the organic surface-crosslinking agent. The inorganic surface-crosslinking agent can be used simultaneously with or separately from the organic surface-crosslinking agent.

Examples of the inorganic surface-crosslinking agent to be used include a divalent or more, preferably trivalent or tetravalent, metal salt (organic salt or inorganic salt), and a hydroxide. Examples of a usable polyvalent metal include aluminum, zirconium, and the like, and the polyvalent metal is also exemplified by aluminum lactate and aluminum sulfate. An aqueous solution containing aluminum sulfate is preferably employed. The inorganic surface-crosslinking agent is used simultaneously with or separately from the organic surface-crosslinking agent.

The surface-crosslinking by use of a polyvalent metal is disclosed in International Publication Nos. 2007/121037, 2008/09843, and 2008/09842, U.S. Pat. Nos. 7,157,141, 6,605,673, and 6,620,889, and U.S. Patent Application Publication Nos. 2005/0288182, 2005/0070671, 2007/0106013, and 2006/0073969.

The liquid permeability and others can be improved by simultaneous or separate use of a cationic polymer particularly having a weight average molecular weight of approximately 5,000 to 1,000,000. Preferable examples of the cationic polymer to be used include a vinyl amine polymer and the like (U.S. Pat. No. 7,098,284, International Publication Nos. 2006/082188, 2006/082189, 2006/082197, 2006/111402, 2006/111403, 2006/111404, and others).

Similarly, the inorganic microparticles can be added. Preferable examples of the inorganic microparticles include silicon dioxide and the like (U.S. Pat. No. 7,638,570 and others).

The production of a water-absorbing resin powder in accordance with the present invention preferably involves a step of adding one or more of the multivalent metal salt, the cationic polymer, and the inorganic microparticles. Such additives are preferably added simultaneously with or separately from the covalent bonding surface-crosslinking agent. This makes it possible to further attain the object (improvement in diffusion absorbency property of the liquid) of the present invention.

In order to prevent a decrease in the surface tension of a water-absorbing resin powder to be obtained, it is preferable to use a surfactant having reactivity or polymerizability with a water-absorbing resin powder or its monomer (for example, a surfactant having a polymerizable unsaturated group (in particular, an $\alpha,\beta$-unsaturated double bond) and a reactive group (a hydroxyl group or an amino group)) or a hydrophilic surfactant having a high water solubility (for example, HLB of 1 to 18, especially even more preferably 8 to 15).

As specific surfactants, surfactants shown as examples in International Publication No. 2011/078298 are suitably used. Among them, a nonionic surfactant is preferable, a nonionic surfactant having a polyoxyethylene chain in a molecule is more preferable, and polyoxyethylene sorbitan fatty acid ester is still more preferable.

The amount of any of these surfactants to be used depends on the type of the surfactant to be used or intended physical properties (in particular, water absorption speed and surface tension). However, the amount used is typically preferably more than 0 weight % and not more than 2 weight %, more preferably more than 0 weight % and not more than 0.03 weight %, even more preferably more than 0 weight % and not more than 0.015 weight %, especially even more preferably more than 0 weight % and not more than 0.01 weight %, most preferably more than 0 weight % and not more than 0.008 weight %, per the amount of a monomer(s) to be used. The amount of the surfactant to be used is applicable to a water-absorbing resin powder after polymerization, and is further applicable, if necessary, to a water-absorbing resin powder as an end product obtained after coating with a surfactant described above in "(2-6) Surface-crosslinking".

[6] Application of Water-Absorbing Resin Powder

Applications of the water-absorbing resin powder obtainable by a production method in accordance with the present invention are not particularly limited. However, the water-absorbing resin powder is preferably used for absorbent articles such as disposable diapers, sanitary napkins, and incontinence pads. The water-absorbing resin powder shows an excellent performance in a case where it is used in high-concentration diapers (disposable diapers each of which contains a large amount of water-absorbing resin).

The term "absorbent body" as used in the present specification refers to a component of the above absorbent article that contains at least a water-absorbing resin powder in accordance with the present invention and optionally contains another absorbent material(s) (fibrous substance such as pulp fiber). In other words, the above absorbent body contains a water-absorbing resin powder produced by the production method described above, and is used in an absorbent article.

The absorbent article includes an absorbent body having a water-absorbing resin content (core concentration, that is, a water-absorbing resin powder content per the total amount of the water-absorbing resin powder and the fibrous material) of preferably 30 weight % to 100 weight %, more preferably 40 weight % to 100 weight %, even more preferably 50 weight % to 100 weight %, further even more preferably 60 weight % to 100 weight %, especially even more preferably 70 weight % to 100 weight %, most preferably 75 weight % to 95 weight %.

For example, in a case where a water-absorbing resin powder in accordance with the present invention is used at a concentration within the above range, the absorbent article, which has a good diffusion absorbency property, has an excellent diffusion absorbency for an absorption liquid such as urine. Liquid is efficiently distributed in the absorbent body, the amount of the liquid to be absorbed by the entire absorbent article is increased, and the liquid is absorbed rapidly. Further, it is possible to provide an absorbent article including an excellent absorbent body.

In a case where the above absorbent body is used in absorbent articles such as disposable diapers, sanitary napkins, incontinence pads, and medical pads, an absorbent article includes (1) a liquid-permeable top sheet to be so positioned as to be adjacent to the body of the wearer, (2) a liquid-impermeable back sheet to be so positioned as to be far from the body of the wearer and adjacent to the clothes worn by the wearer, and (3) the absorbent body positioned between the top sheet and the back sheet. The absorbent body may be provided in two or more layers or be used in combination with a pulp layer or the like.

The present invention is not limited to the embodiments, but can be altered by a skilled person in the art within the scope of the claims. An embodiment derived from a proper combination of technical means each disclosed in a different embodiment is also encompassed in the technical scope of the present invention.

EXAMPLES

The following description will discuss the present invention with reference to Examples. It should be noted that the present invention is not limited to the Examples. Unless otherwise stated, physical properties specified in the claims or Examples of the present invention were obtained by EDANA and other measurement methods below under conditions where the temperature was room temperature (20° C. to 25° C.) and the humidity was 50 RH %. For electric devices used in the Examples and Comparative Examples, power sources of 200 V or 100 V and 60 Hz were used. For convenience, "liter" may be referred to as "L" and "weight %" may be referred to as "wt %"

[Measurements of Physical Properties of Water-Absorbing Resin Powder]

The following description will discuss methods for measuring physical properties of a water-absorbing resin powder in accordance with the present invention. In a case where the measurement target is not water-absorbing resin powder, for example, water-absorbing resin particles, the term "water-absorbing resin powder" in the description of the physical property measurement should be replaced with "water-absorbing resin particles" accordingly.

For the present invention, any physical property influenced by the moisture content was evaluated with use of a value obtained by correcting the actual measured value on the basis of the moisture content. A value as corrected on the basis of the moisture content is calculated by dividing the actual measured value by (1−moisture content/100). The value as corrected on the basis of the moisture content is expressed below as a value per 100 parts by weight of the solid content of a water-absorbing resin powder. A water-absorbing resin powder included in a commercially available absorbent article such as a disposable diaper has typically already absorbed moisture, and thus does not show intrinsic values for the CRC, the particle size, and the like. In view of that, in a case where the moisture content exceeds 10 weight % (in particular, 20 weight %), the water-absorbing resin powder simply needs to be dried for reduction of the moisture content to not more than 10 weight % at, for example, 60° C. for 16 hours under reduced pressure of not more than 10 mmHg before physical property measurements.

(1) Particle Size Distribution (PSD), Weight Average Particle Diameter (D50), and Logarithmic Standard Deviation (σζ) of Particle Size Distribution The particle size distribution (PSD) of a water-absorbing resin powder in accordance with the present invention was measured in conformity with an EDANA method (ERT 420.2-02). The weight average particle diameter (D50) and the logarithmic standard deviation (σζ) were measured in conformity with "(3) Mass-Average Particle Diameter (D50) and Logarithmic Standard Deviation (σζ) of Particle Diameter Distribution" of U.S. Pat. No. 7,638,570.

(2) Water Absorption Time According to a Vortex Method

The water absorption time according to a vortex method of a water-absorbing resin powder in accordance with the present invention was measured through the procedure below.

First, 0.02 parts by weight of food blue No. 1 (CAS No. 3844-45-9) as a food additive was added to 1000 parts by weight of an aqueous sodium chloride solution (physiological saline) prepared in advance at 0.90 weight % to color the physiological saline blue. Then, the temperature of the physiological saline was adjusted to 30° C. (±0.5° C.).

Next, 50 ml of the blue physiological saline was put into a 100-ml beaker. While the physiological saline was being stirred at 600 rpm with use of a magnet stirrer that was made of Teflon (registered trademark) and that had a cylindrical shape with a length of 40 mm and a thickness of 8 mm, 2.0 g of a water-absorbing resin powder was put into the physiological saline.

The starting point and ending point during measurement of a water absorption time were in conformity with the standard described in JIS K 7224 (1996) "Koukyusuiseijyushi no Kyushusokudo Shiken Houhou Kaisetsu (Explanation of Method for Testing Absorption Speed of Superabsorbent Resin)".

(3) Elastic Modulus Index (EMI)

The elastic modulus index (EMI) of a water-absorbing resin powder in accordance with the present invention was measured through the procedure below.

[Measurement of Elastic Modulus]

First, the method described below was used to measure the elastic modulus of a water-absorbing resin powder separated on the basis of the particle diameter (particle size).

(Step 1: Classifying water-absorbing resin powder)

Ten grams of water absorbent resin powder was classified with use of six JIS standard sieves (THE IIDA TESTING SIEVE, diameter: 8 cm) having respective mesh sizes of 710 μm, 600 μm, 500 μm, 425 μm, 300 μm, and 150 μm. The classification was carried out by sieving the water absorbent resin powder for 5 minutes with use of a vibration classifier (IIDA SIEVE SHAKER, TYPE: ES-65 [number of rotations: 60 Hz, 230 rpm; number of impacts: 60 Hz, 130 rpm], SER. No. 0501).

The above operation produced water-absorbing resin powder classified on the basis of the particle diameter (particle size). A sieving operation involving use of, for example, a JIS standard sieve having a mesh size of 600 μm at the upper stage and a JIS standard sieve having a mesh size of 500 μm at the lower stage will produce a water-absorbing resin powder with particle diameters of not less than 500 μm and less than 600 μm. The elastic modulus index measured of a water-absorbing resin powder having particle diameters (particle sizes) of not less than 500 μm and less than 600 μm is referred to as "elastic modulus index (600-500)".

(Step 2: Swelling water-absorbing resin powder)

An amount of the water-absorbing resin powder classified on the basis of the particle size in the step 1 above that (added amount) was calculated in accordance with Formula (9) below was put into a 10-ml plastic container. Then, 8.0 g of deionized water was added into the container, and the water-absorbing resin powder was immersed in the deionized water for 16 hours to be swollen.

[Math. 2]

Water-absorbing resin powder [g]=2.00 g/(CRCdw+1)   Formula (9)

Formula (9) above is a formula for calculating the amount of a water-absorbing resin powder with which amount swollen gel particles will have a weight of 2.00 g. With this measurement method, swollen gel particles may not have a weight of exactly 2.00 g due to a measurement error. In such a case, the weight is corrected. Specifically, in a case where swollen gel particles have a weight of 2.01 g, the elastic modulus value measured is multiplied by 0.995 (=2.00/2.01) for a corrected value. Further, "CRCdw" in Formula (9) means the CRC (centrifuge retention capacity) that water-absorbing resin powder has when it has been swollen with deionized water. The CRCdw is determined as measured in (6) below except that the 0.9 weight % aqueous sodium chloride solution is replaced with deionized water, the amount of the sample is changed from 0.2 g to 0.05 g, and the immersion time period is changed from 30 minutes to 16 hours.

(Step 3: Measuring elastic modulus)

The elastic modulus of the water-absorbing resin powder as swollen in the step 2 above (hereinafter referred to as "swollen gel") was measured with use of a rheometer (MCR301, available from Anton-Paar) (see FIG. 1). The following description will discuss the measurement method in detail with reference to FIG. 1.

First, swollen gel 41 obtained in the step 2 above was put onto a dish 40 (inner diameter: 51 mm, depth: 10 mm, made of aluminum) of a rheometer 300 together with swelling liquid (deionized water), and was leveled off to be present evenly in the dish 40. The dish 40 was fixed to the rheometer 300. The rheometer 300 and the dish 40 were oriented strictly horizontally.

Next, a parallel plate 42 (diameter: 50 mm, made of aluminum) to which a rotary shaft 43 was attached perpendicularly thereto was fitted into the dish 40, and then the rotary shaft 43 was rotated in the direction indicated by the arrow in FIG. 1 to provide vibrations to the swollen gel 41. The storage elastic modulus was measured under the measurement conditions below.

<Measurement Conditions>

Measurement mode: Vibration (dynamic) measurement

Strain: 0.02% (error: ±2%)

Angular frequency: 10 rad/s (error: ±2%)

Starting time of measurement: At the time point at which the upper parallel plate 42 came into contact with the swollen gel 41

Vertical load: 10 N to 40 N, imposed discontinuously

Increased by 5 N each time a measurement time period of 100 seconds elapsed

Measurement intervals: 5 seconds

Number of measurement points: 20 points×7 loading conditions

Measurement time period: 700 seconds (=5 seconds×20 points×7 loading conditions)

The above measurement was carried out of the water-absorbing resin powder obtained in the step 1 and having different particle sizes. The dish 40 and the parallel plate 42 for use in the measurement were, for each measurement, each replaced with a new one, or washed sufficiently, dried, polished with use of a polishing cloth (available from Trusco Nakayama Corporation, base material: cotton, abrasive:

brown alumina abrasive [particle size: #15000], with wax therein), and washed again before reuse. For each of the strain and angular frequency, conditions were selected as appropriate under which a measurement value was stable within the above range.

The arithmetic average of, among storage elastic modulus values obtained during the above measurement, a total of five-point measurement values obtained during a measurement time period of 600 seconds to 700 seconds (with a load of 40 N) was used as an elastic modulus G' (unit: Pa) of the present invention.

[Calculating Elastic Modulus Index (EMI)]

With use of the above elastic modulus and the CRC and CRCdw values below, the elastic modulus index (EMI) was calculated in accordance with Formulae (3) and (10) to (17) below. The elastic modulus index (EMI) is a value obtained by correcting the elastic modulus G' on the basis of a theoretical surface area and CRC of the swollen gel, and is a value that serves as an index for evaluation of the performance of a water-absorbing resin powder. The description below uses the acronym "EMI" to refer to "elastic modulus index".

[Math. 3]

EMI=Elastic modulus G'/(theoretical surface area (TGS) of swollen gel particles)×CRC   Formula (3)

In Formula (3) above, "CRC" refers to a CRC value measured of a water-absorbing resin powder before the step 1 is carried out for measurement of the elastic modulus, and "swelling gel" is that which is obtained in the step 2 for measurement of the elastic modulus.

The numerical values (A) to (I) necessary for the calculation of the EMI are calculated in accordance with Formulae (10) to (17) below.

[Math. 4]

TGS [cm$^2$]=theoretical surface area($A$) of single swollen gel particle [cm$^2$]×number($B$) of particles in measurement   Formula (10)

[Math. 5]

Theoretical surface area($A$) of single swollen gel particle [cm$^2$]=4×π×(theoretical radius($C$) of single swollen gel particle)$^2$   Formula (11)

[Math. 6]

Theoretical radius($C$) of single swollen gel particle [cm]=(volume($D$) of single swollen gel particle×¾×1/π)$^{1/3}$   Formula (12)

[Math. 7]

Volume($D$) of single swollen gel particle [cm$^3$] =2.00/number($B$) of particles before swelling   Formula (13)

[Math. 8]

Number($B$) of particles before swelling=weight($E$) of water-absorbing resin powder/(theoretical volume($F$) of single particle before swelling×1.6)   Formula (14)

[Math. 9]

Theoretical volume($F$) of single particle before swelling [cm$^3$]=4/3×π×(diameter($G$) of intermediate particles before swelling/2)$^3$   Formula (15)

[Math. 10]

Diameter($G$) of intermediate particles before swelling [cm]=(mesh size($H$) of upper sieve for classification+mesh size($I$) of lower sieve for classification)/2   Formula (16)

[Math. 11]

Weight($E$) of water-absorbing resin powder [g]=2.00/ (CRCdw+1)   Formula (17)

(4) Internal Gas Bubble Ratio

The internal gas bubble ratio of a water-absorbing resin powder in accordance with the present invention was measured through the procedure below.

With use of an apparent density ρ1 (unit: g/cm$^3$) measured by the method described in [Apparent density] below and a true density ρ2 (unit: g/cm$^3$) measured by the method described in [True density] below, the internal gas bubble ratio of a water-absorbing resin powder was calculated in accordance with Formula (5) below.

[Math. 12]

Internal gas bubble ratio[%]=(ρ2−ρ1)/ρ2×100   Formula (5)

[Apparent Density]

The apparent density of the water-absorbing resin powder from which water had been removed was measured by use of a dry densimeter (the volume of a water-absorbing resin powder having a predetermined weight was dry-measured). The apparent density is a density calculated in consideration of gas bubbles (internal gas bubbles) present inside a resin.

Specifically, 6.0 g of the water-absorbing resin powder was weighed and placed in an aluminum cup whose bottom surface had a diameter of approximately 5 cm. Then, the water-absorbing resin powder was dried in a windless dryer at 180° C. The water-absorbing resin powder was left to stand still for 3 hours or more until the moisture content of the water-absorbing resin powder was not more than 1 weight %, so that the water-absorbing resin powder was dried sufficiently. The apparent density (unit: g/cm$^3$) of 5.00 g of the dried water-absorbing resin powder was measured by use of an automatic dry densimeter (AccuPycII 1340TC-10CC, available from Shimadzu Corporation, carrier gas: helium). The measurement was repeated until five or more identical measured values were obtained consecutively.

[True Density]

Internal gas bubbles (closed cells) present inside the water-absorbing resin powder have a diameter of normally 1 μm to 300 μm. In pulverization, portions close to the closed cells are pulverized preferentially. For this reason, when the water-absorbing resin powder is pulverized until the particle diameters thereof are less than 45 μm, the resultant water-absorbing resin powder has almost no closed cells. Therefore, in the present invention, the dried density of the water-absorbing resin powder having been pulverized to have a size of less than 45 μm was evaluated as a true density.

Specifically, 15.0 g of the water-absorbing resin powder and 400 g of columnar porcelain balls (diameter: 13 mm, length: 13 mm) were placed in a ball mill pot (available from TERAOKA, model No. 90, internal dimensions: 80 mm in diameter and 75 mm in height, external dimensions: 90 mm in diameter and 110 mm in height), and then the ball mill pot was operated at 60 Hz for 2 hours, so that a water-absorbing resin powder which would pass through a JIS standard sieve having a mesh size of 45 μm (water-absorbing resin powder whose particle diameters were less than 45 μm) was obtained. Then, 6.0 g of that a water-absorbing resin powder whose particle diameters were less than 45 μm was dried at 180° C. for 3 hours or more as in the case of [Apparent density] described earlier, and thereafter the dried density was measured. The measurement value thus obtained was regarded as the "true density" of the present invention.

(5) Surface Tension

The surface tension of a water-absorbing resin powder in accordance with the present invention was measured through the procedure below.

First, 50 ml of physiological saline having a temperature adjusted to 20° C. was put into a sufficiently washed 100-ml beaker. Then, the surface tension of the physiological saline was measured with the use of a surface tension meter (available from KRUSS, K11 automatic surface tension meter). In this measurement, the surface tension needs to be 71 mN/m to 75 mN/m.

Next, a fluorocarbon resin rotor that had been sufficiently washed and had a length of 25 mm, and 0.5 g of a water-absorbing resin powder were put in the beaker containing the physiological saline whose temperature had been adjusted to 20° C. and surface tension had been measured, and then stirred at 500 rpm for 4 minutes. After 4 minutes, the stirring was stopped, and then, after the water-absorbing resin powder absorbed water and was precipitated, the surface tension of the supernatant liquid was measured through a similar operation. For the present invention, a plate method using a platinum plate was employed, and the plate was sufficiently washed with deionized water and also washed while being heated by the use of a gas burner before being used in each of the measurements.

(6) CRC and CRCdw

The CRC of a water-absorbing resin powder in accordance with the present invention was measured in conformity with an EDANA method (ERT 441.2-02). Specifically, 0.200 g of a water-absorbing resin powder was weighed and uniformly placed in a nonwoven fabric bag (60 mm×60 mm) and the bag was heat-sealed. Then, the bag was immersed in 1000 mL of a 0.9 weight % aqueous sodium chloride solution whose temperature had been adjusted to 25° C.±3° C. After 30 minutes, the bag was pulled out and dewatered by use of a centrifugal separator (centrifuge available from KOKUSAN Corporation, type H-122) at 250 G for 3 minutes.

Then, the weight W1 (unit: g) of the bag was measured. A similar operation was carried out without water absorbent resin powder, and the weight W2 (unit: g) of the bag in that case was measured. The CRC was calculated in accordance with Formula (4) below.

[Math. 13]

$$CRC\ (g/g) = \{(W1 - W2)/(\text{weight of water-absorbing resin powder})\} - 1 \quad \text{Formula (4)}$$

The CRCdw of a water-absorbing resin powder in accordance with the present invention was calculated through the same operation as that for the CRC above except that the 0.9 weight % aqueous sodium chloride solution was replaced with deionized water, the amount of the water-absorbing resin powder was changed from 0.200 g to 0.05 g, and the free swelling period was changed from 30 minutes to 16 hours, and in accordance with Formula (4).

(7) AAP

The AAP of a water-absorbing resin powder in accordance with the present invention was measured in conformity with an EDANA method (ERT 442.2-02).

(8) Ext

The Ext of a water-absorbing resin powder in accordance with the present invention was measured in conformity with an EDANA method (ERT 470.2-02).

(9) Moisture Content

The moisture content of a water-absorbing resin powder in accordance with the present invention was measured in conformity with an EDANA method (ERT 430.2-02). For the present invention, the amount of a sample was changed to 1.0 g, and the drying temperature was changed to 180° C. The value calculated from (100−moisture content) is defined as the resin solid content (unit: weight %).

(10) SFC

The SFC of a water-absorbing resin powder in accordance with the present invention was measured in conformity with the measurement method described in U.S. Pat. No. 5,669,894.

(11) Diffusion Absorbency Period

The diffusion absorbency period of a water-absorbing resin powder in accordance with the present invention was measured through the procedure below. The measurement involved use of a diffusion absorbency period measuring device 200 illustrated in FIG. 2. The following description will discuss the measuring device.

[Measuring Device]

Figure 2:
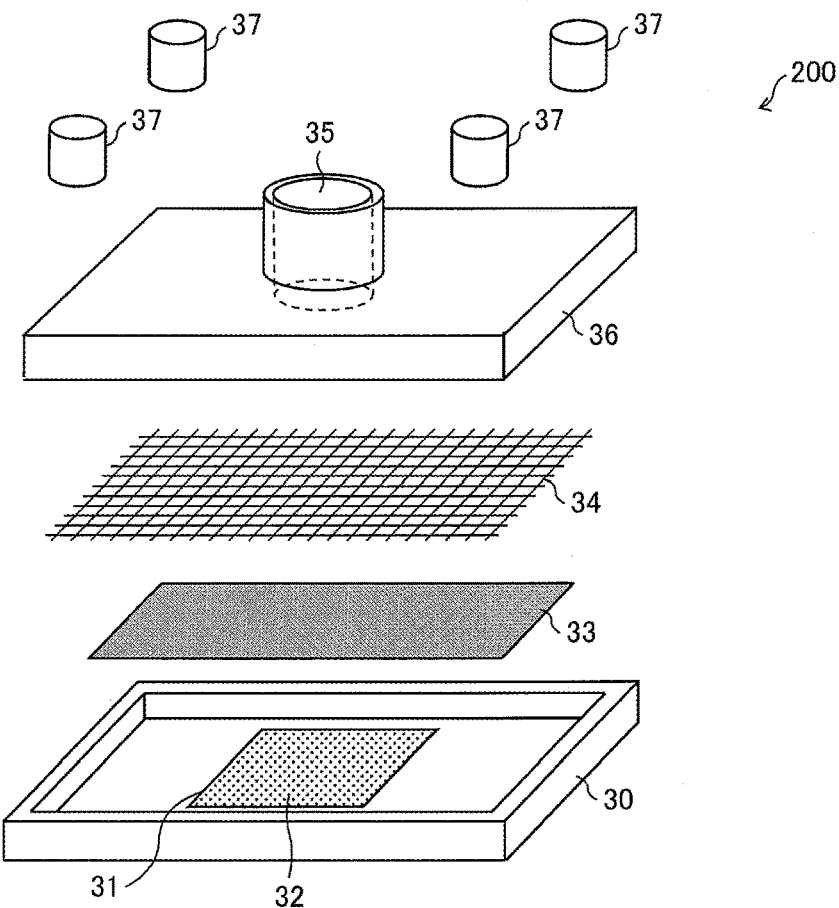
FIG. 2 is a diagram schematically illustrating respective appearances of separate members of a device for measuring a diffusion absorbency period.

The diffusion absorbency period measuring device 200 illustrated in FIG. 2 is a measuring device produced for simulated evaluation of the performance of an absorbent article such as a disposable diaper. FIG. 2 shows a tray 30, a water-absorbing resin powder dispersion region 31, a water-absorbing resin powder 32, a top sheet 33, a metal gauze 34, an inlet 35, a lid 36, and weights 37.

The respective materials of the tray 30 and the lid 36 are each not limited to any particular one. Preferable examples include acrylic resin, polypropylene, and Teflon (registered trademark) resin. The dispersion region 31 is preferably positioned at a central portion of the tray 30 with an area of approximately half the bottom surface of the depression of the tray 30 in order for an appropriate amount of a water-absorbing resin powder 32 to absorb liquid uniformly. The water-absorbing resin powder 32 preferably has an amount that allows the water-absorbing resin powder 32 to be dispersed in the dispersion region 31 uniformly so that the water-absorbing resin powder 32 is absent in as few portions as possible. For uniform absorption, a measure is preferably taken such as applying an antistatic agent to the tray 30 or blowing on the tray 30 before the dispersion to prevent static electricity.

The top sheet 33 is a sheet included in an absorbent article such as a disposable diaper that is the closest to the wearer, and contains nonwoven fabric and paper. The top sheet 33 can be a conventionally publicly known top sheet, for example, a top sheet recovered from an absorbent article such as the above. The measurement method below uses, as the top sheet 33, a top sheet taken out from a Mamy Poko (product name) tape type (size L, purchased in Japan in June 2014; number on the package bottom surface: 404088043) available from Unicharm Corporation. The top sheet 33 is, however, not limited to this.

The top sheet 33 is preferably so sized as to entirely cover the dispersion region 31 and not extend beyond the depression of the tray 30. Further, the top sheet 33 is preferably so placed that the distance from an inner wall of the tray 30 is equal in the left-and-right direction and the up-and-down direction. In FIG. 2, the left-and-right direction corresponds to the direction in which the long sides of the tray 30 extend, whereas the up-and-down direction corresponds to the direction in which the short sides of the tray 30 extend.

The metal gauze 34 serves to allow for passage and diffusion of a 0.9 weight % aqueous sodium chloride solution put through the inlet 35. The material of the metal gauze 34 is not limited to any particular one. The metal gauze 34 is, however, preferably made of stainless steel. The metal gauze 34 has openings with a size (mesh size) of preferably 600 μm to 2000 μm, more preferably 1000 μm to 1500 μm. The measurement method below uses, as the metal gauze 34, a JIS metal gauze that is made of stainless steel, that has 14 meshes, that has a mesh size of 1.21 mm, and that has a wire diameter of 0.6 mm.

Figure 3:
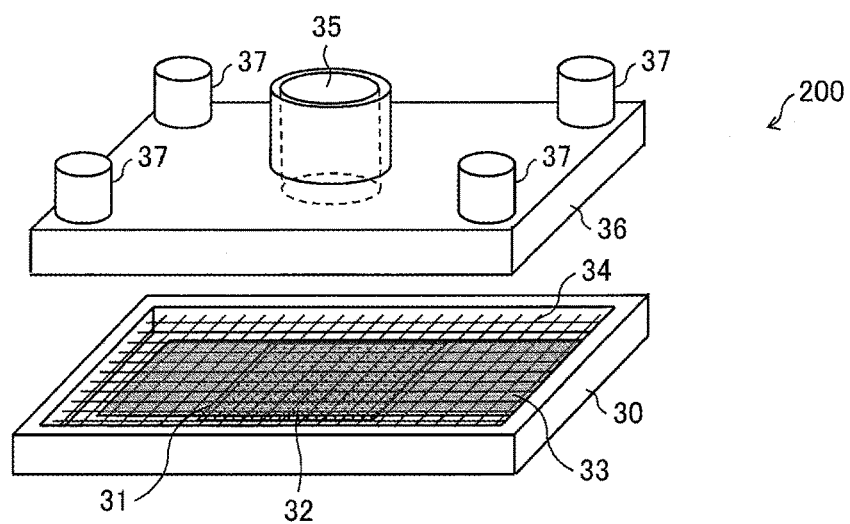
FIG. 3 is a diagram schematically illustrating a state of a device for measuring a diffusion absorbency period in which the members illustrated in FIG. 2 are placed on a tray and weights are placed on a lid provided with an inlet.

The weights 37 simply need to impose a load onto a water-absorbing resin powder 32 evenly. The material, the number, and the like thereof are not particularly limited. The load is preferably 35 g/cm$^2$ to 500 g/cm$^2$ on the area of the dispersion of a water-absorbing resin powder 32 (that is, the area of the dispersion region 31). FIG. 3 illustrates an embodiment in which four weights 37 are placed on the respective corners of the lid 36. The placement of the weights 37 is, however, not limited to such an embodiment as long as a load is imposed evenly. For example, two cuboid weights each having long sides equal in length to the short sides of the lid 36 may be so placed on the lid 36 as to lie along the respective short sides of the lid 36.

The inlet 35 is preferably positioned at a central portion of the lid 36 as illustrated in FIG. 2 for uniform absorption. The lid 36 is preferably so sized as to be slightly smaller than the internal dimensions of the tray 30 to be fitted in the depression of the tray 30.

Figure 4:
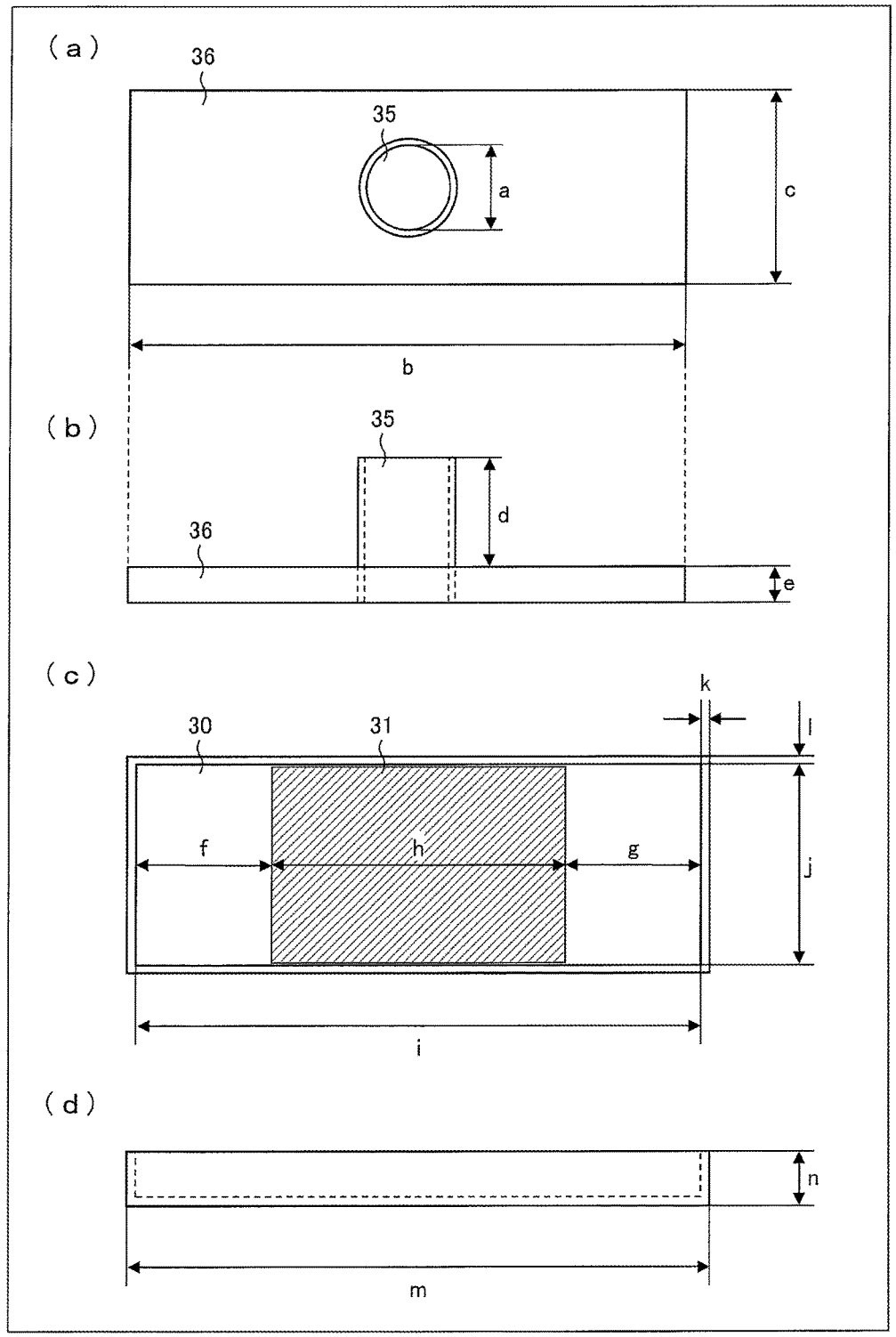
FIG. 4 shows a top view and side view of a lid for a diffusion absorbency period measuring device and a top view and side view of a tray for the diffusion absorbency period measuring device.

FIG. 4 shows a top view of the lid 36, which is provided with the inlet 35 ((a) of FIG. 4), a side view thereof ((b) of FIG. 4), a top view of the tray 30 ((c) of FIG. 4), and a side view thereof ((d) of FIG. 4).

(a) of FIG. 4 shows the symbol "a" to indicate the inner diameter of the inlet 35, the symbol "b" to indicate the width of the lid 36, and the symbol "c" to indicate the length of the lid 36. (b) of FIG. 4 shows the symbol "d" to indicate the height of the cylindrical portion of the inlet 35 and the symbol "e" to indicate the thickness of the lid 36.

(c) of FIG. 4 shows how the water-absorbing resin powder dispersion region 31 is positioned on the tray 30. (d) of FIG. 4 is a side view corresponding to (c) of FIG. 4.

(c) of FIG. 4 shows the symbols "f" and "g" to indicate that the water-absorbing resin powder dispersion region 31 is 100.5 mm apart inward from the lengthwise inner walls, the symbol "h" to indicate the width (200 mm) of the water-absorbing resin powder dispersion region 31, the symbol "i" to indicate the internal width (401 mm) of the tray 30, the symbol "j" to indicate the internal length (151 mm) of the tray 30 and the length (151 mm) of the water-absorbing resin powder dispersion region 31, and the symbols "k" and "l" to each indicate the difference (5 mm) between the internal dimension and external dimension of the tray 30. (d) of FIG. 4 shows the symbol "m" to indicate the external width (411 mm) of the tray 30 and the symbol "n" to indicate the height (35 mm) of the tray 30.

[Measurement Method]

First, 12 g of a water-absorbing resin powder 32 was dispersed evenly in a dispersion region 31 (with a width of 200 mm and a length of 151 mm; 100.5 mm inward of the lengthwise inner walls of a tray 30) in the tray 30 (internal dimensions: a width of 401 mm, a length of 151 mm, and a height of 30 mm; external dimensions: a width of 411 mm, a length of 161 mm, and a height of 35 mm; made of acrylic resin) (basis weight: 397 g/m$^2$). Before the dispersion, an antistatic agent was applied to the tray 30 for prevention of static electricity.

Subsequently, a top sheet 33 was placed on the water-absorbing resin powder 32 dispersed. The top sheet 33 was so placed that the distance from an inner wall of the tray 30 was equal in the left-and-right direction and the up-and-down direction.

The top sheet 33 was a top sheet taken out from a Mamy Poko (product name) tape type (size L, purchased in Japan in June 2014; number on the package bottom surface: 404088043) available from Unicharm Corporation. This top sheet taken out had a length of 14 cm, a width of 39 cm, and a weight of 3.3 g to 3.6 g. Pulp and the like in the disposable diaper that had adhered to the top sheet with an adhesive were sufficiently removed before the use.

Next, a metal gauze 34 (with a width of 398 mm and a length of 148 mm; JIS metal gauze made of stainless steel, 14 meshes, with a mesh size of 1.21 mm and a wire diameter of 0.6 mm) was placed on the top sheet 33. Further, an acrylic resin lid 36 (with a width of 400 mm, a length of 150 mm, and a thickness of 20 mm; the cylindrical portion having a height of 70 mm) having, at a central portion thereof, a cylindrical inlet 35 with an inner diameter of 70 mm was placed on the metal gauze 34.

Subsequently, weights 37 made of stainless steel were placed on the lid 36 for an even load on the water-absorbing resin powder 32. The respective weights of the weights 37 and/or the like were adjusted so that the total weight of the metal gauze 34, the acrylic resin lid 36, and the weights 37 was 5672 g (the load was 9.45 g/cm$^2$ on the area of the metal gauze 34 and 18.78 g/cm$^2$ on the area in which the water-absorbing resin powder 32 was dispersed).

Then, 60 g of a 0.9 weight % aqueous sodium chloride solution was put through the inlet 35 of the lid 36 in 5 seconds. The liquid put was diffused on the metal gauze 34 while passing through the metal gauze 34, and was thereafter absorbed by the water-absorbing resin powder 32. The aqueous sodium chloride solution may be colored blue through addition of blue No. 1 (0.04 g for 1000 g of the aqueous solution).

After the aqueous sodium chloride solution was put into the measuring device 200, a measurement was made of the time period (first time) needed for liquid retained in the mesh of the metal gauze 34 to be entirely absorbed by the water absorbent resin powder. Swollen gel may move beyond the outer edge of the metal gauze 34. The liquid absorption may, in this case, be difficult to determine. The above measurement of the time period thus excluded an outer-edge portion (approximately 1 cm) of the metal gauze 34.

Subsequently, 10 minutes after the start of putting the aqueous sodium chloride solution the first time, the same amount of the aqueous sodium chloride solution was put, and a measurement was made, similarly to the first time, of the time period (second time) needed for liquid retained in the mesh of the metal gauze 34 to be entirely absorbed by the water absorbent resin powder. After that, the same amount of the aqueous sodium chloride solution was put similarly at intervals of 10 minutes, and measurements were made of respective time periods for the third and fourth times.

The sum of the respective time periods measured through the above operations for the first through fourth times was used as a diffusion absorbency period for the present invention.

Comparative Example 1

The operation below was carried out with reference to Production Example 1 and Example 1 of International Publication No. WO2011/126079.

As a device for producing a polyacrylic acid (salt)-based water-absorbing resin powder, there was prepared a continuous production device for carrying out a polymerization step, a gel-crushing step, a drying step, a pulverization step, a classification step, a surface-crosslinking step, a particle sizing step, and a transportation step for linking the above individual steps. The continuous production device had a production capacity of approximately 3500 kg/hr. The above steps can each include a single line or two or more lines. In a case where the above steps each include two or more lines, the production capacity is shown as the sum of the respective production amounts of the two or more lines. The continuous production device was used to continuously produce a polyacrylic acid (salt)-based water-absorbing resin powder.

First, there was prepared an aqueous monomer solution (1) containing 193.3 parts by weight of acrylic acid, 64.4 parts by weight of a 48 weight % aqueous sodium hydroxide solution, 1.26 parts by weight of polyethylene glycol diacrylate (average n number: 9), 52 parts by weight of a 0.1 weight % aqueous pentasodium ethylenediamine tetra(methylene phosphonate) solution, and 134 parts by weight of deionized water.

Next, the aqueous monomer solution (1) whose temperature had been adjusted to 40° C. was continuously fed into the continuous production device by use of a metering pump, and then 97.1 parts by weight of a 48 weight % aqueous sodium hydroxide solution was continuously line-mixed with the aqueous monomer solution (1). At this stage, the temperature of the aqueous monomer solution (1) was raised to 85° C. due to heat of neutralization.

Furthermore, 8.05 parts by weight of a 4 weight % aqueous sodium persulfate solution was continuously line-mixed with the aqueous monomer solution (1), and then the aqueous monomer solution (1) was continuously fed into a continuous polymerization device having a planar polymerization belt with a dam at each end, so that the fed mixture had a thickness of approximately 7.5 mm. Thereafter, polymerization (polymerization time: 3 minutes) was carried out continuously, so that a hydrogel (1) in the shape of a belt was obtained.

Next, the belt-shaped hydrogel (1) was continuously cut at regular intervals in the width direction with respect to the traveling direction of the polymerization belt so that the cut length was approximately 300 mm.

The hydrogel (1), which had a cut length of approximately 300 mm, was fed into a screw extruder for gel-crushing (gel-crushing step). The screw extruder was a meat chopper provided with, at a tip thereof, a porous plate having a diameter of 340 mm, a pore diameter of 22 mm, 105 pores, an aperture ratio of 52%, and a thickness of 20 mm and having a screw including a shaft with a diameter of 152 mm. While the screw shaft of the meat chopper was being rotated at 115 rpm, the hydrogel (1) was fed at 132800 g per minute together with 70° C. warm water at 855.8 g per minute and water vapor at 3333 g per minute.

At this stage, the gel-grinding energy (GGE) was 27.8 J/g, and the gel-grinding energy (2) (GGE (2)) was 15.5 J/g. The meat chopper had a current value of 104.7 A on average during the gel-crushing. The hydrogel (1) had a temperature of 90° C. before the gel-crushing, whereas comparative crushed gel after the gel-crushing, that is, a comparative particulate hydrogel (1), had a decreased temperature of 85° C.

Next, the comparative particulate hydrogel (1) was dispersed on a through-flow belt (the comparative particulate hydrogel (1) having a temperature of 80° C. at this stage) within 1 minute of the end of the gel-crushing, and was then dried at 185° C. for 30 minutes (drying step). This produced 246 parts by weight of a comparative dried polymer (1) (total discharged amount in the drying step).

The through-flow belt was moved at a speed of 1 m/min. The hot air had an average air velocity of 1.0 m/s in the direction perpendicular to the traveling direction of the through-flow belt. The air velocity of the hot air was measured with use of Anemomaster 6162 (constant temperature thermal anemometer available from Kanomax Japan Inc.).

Next, the total amount of the comparative dried polymer (1) produced through the drying step and having a temperature of approximately 60° C. was fed continuously into a three-stage roll mill for pulverization (pulverizing step), and was further classified with use of JIS standard sieves having respective mesh sizes of 710 μm and 175 μm. This produced comparative water-absorbing resin particles (1) having uneven shapes.

The comparative water-absorbing resin particles (1) had a weight average particle diameter (D50) of 340 μm, a logarithmic standard deviation (o) of 0.32, a CRC of 32.0 g/g, a water-soluble content of 6.9 weight %, and 0.7 weight % of 150 μm passage particles (that is, a proportion of particles that would pass through a sieve having a mesh size of 150 μm).

Next, a (covalent bonding) surface-crosslinking agent solution (1) containing 0.3 parts by weight of 1,4-butanediol, 0.6 parts by weight of propylene glycol, and 3.0 parts by weight of deionized water was mixed uniformly with 100 parts by weight of the comparative water-absorbing resin particles (1). The mixture was heat-treated at 208° C. for approximately 40 minutes so that comparative water-absorbing resin powder (1) to be produced would have a CRC within a range of 26.6 g/g to 27.4 g/g.

After that, the mixture was cooled. Then, a (ionic bonding) surface-crosslinking agent solution (1) containing 1.17 parts by weight of a 27.5 weight % aqueous aluminum sulfate solution (8 weight % based on aluminum oxide), 0.196 parts by weight of a 60 weight % aqueous sodium lactate solution, and 0.029 parts by weight of propylene glycol was mixed uniformly with the above mixture. Subsequently, the resulting mixture was crushed until it passed through a JIS standard sieve having a mesh size of 710 μm (sizing step). This produced comparative water-absorbing resin powder (1).

Table 3 shows the CRC, the elastic modulus index ("EMI" in the table; the same applies below), the water absorption time according to a vortex method ("Vortex" in the table); the same applies below), and the diffusion absorbency period of the comparative water-absorbing resin powder (1) produced through the above operations. Table 4 shows the results of measuring the elastic modulus of the comparative water-absorbing resin powder (1). The EMI value shown in Table 3 was calculated with use of a comparative water-absorbing resin powder (1) having particle sizes of not less than 500 μm and less than 600 μm that was obtained through a sieving operation involving use of a JIS standard sieve having a mesh size of 600 μm at the upper stage and a JIS standard sieve having a mesh size of 500 μm at the lower stage in the step 1 of the EMI measurement method described above. The comparative water-absorbing resin powder (1) produced had an AAP 0.3 of 27.9 g/g.

The comparative water-absorbing resin powder (1) produced through the above operations was classified with use of JIS standard sieves having respective mesh sizes of 710 μm and 500 μm. This produced particles having respective particle sizes of not less than 500 μm and less than 710 μm. The proportion of flake-shaped particles (that is, particles each with a thickness of roughly not more than 300 μm) contained in the above particles having respective particle sizes of not less than 500 μm and less than 710 μm was observed under an electron microscope (with use of the 3D measurement function of VE-9800, available from Keyence Corporation). The proportion was 16% (that is, 32 particles out of 200 particles were flake-shaped particles).

Example 1

The comparative water-absorbing resin powder (1) produced in Comparative Example 1 above was classified with use of JIS standard sieves having respective mesh sizes of 710 μm and 500 μm. This produced particles having respective particle sizes of not less than 500 μm and less than 710 μm and particles having respective particle sizes of less than 500 μm. The particles having respective particle sizes of not less than 500 μm and less than 710 μm were classified by using a sieve provided with a ton-cap metal gauze having rectangular mesh openings (with a long side of 728 μm and a short side of 335 μm) for removal of flake-shaped particles. The weight of the removed flake-shaped particles had a proportion of 17.1 weight % relative to the weight of the particles having respective particle sizes of not less than 500 μm and less than 710 μm and subjected to the sieve classification. The particles as classified were observed under an electron microscope, with the result that no flake-shaped particles were found.

The particles having respective particle sizes of not less than 500 μm and less than 710μ, from which flake-shaped particles had been removed, were mixed with the particles having respective particle sizes of less than 500 μm. This produced a water-absorbing resin powder (1) from which flake-shaped particles had been removed. The water-absorbing resin powder (1) had an internal gas bubble ratio of 2.1%, a surface tension of 72 mN/m, and an AAP 0.3 of 28.3 g/g. Table 3 shows the CRC, the EMI, the water absorption time according to a vortex method, and the diffusion absorbency period of the water-absorbing resin powder (1). Table 5 shows the results of measuring the elastic modulus of the water-absorbing resin powder (1).

Comparative Example 2

An operation similar to the operation of Comparative Example 1 above was carried out except that the amount of polyethyleneglycol diacrylate (average n number: 9) to be used was changed to 1.05 parts by weight. The operation produced hydrogel (2) in the shape of a belt and cut hydrogel (2).

Subsequently, the cut hydrogel (2) produced through the above operation was fed at 360 g per minute (60 g of the gel was put at intervals of 10 seconds) into a gel-crushing device provided with a porous plate having a diameter of 100 mm, a die pore diameter of 9.5 mm, and a die thickness of 10 mm, screw No. S86-445 (see Table 1 for the shape of the screw), and barrel No. B88-874 (see Table 2 for the shape of the barrel) while the screw rotating shaft was being rotated at a rotation rate of 172 rpm for gel-crushing. This produced comparative particulate hydrogel (2).

Next, operations similar to those of Comparative Example 1 (specifically, a drying step, a pulverizing step, and classification involving use of JIS standard sieves having respective mesh sizes of 710 μm and 175 μm) were carried out on the comparative particulate hydrogel (2). This produced comparative water-absorbing resin particles (2) having uneven shapes.

Next, a (covalent bonding) surface-crosslinking agent solution (2) containing 0.3 parts by weight of ethylene carbonate, 0.6 parts by weight of propylene glycol, and 3.0 parts by weight of deionized water was mixed uniformly with 100 parts by weight of the comparative water-absorbing resin particles (2), and was heat-treated at 208° C. approximately for 40 minutes. After that, the mixture was cooled. Then, a (ionic bonding) surface-crosslinking agent solution (2) containing 1.17 parts by weight of a 27.5 weight % aqueous aluminum sulfate solution (8 weight % based on aluminum oxide), 0.196 parts by weight of a 60 weight % aqueous sodium lactate solution, and 0.029 parts by weight of propylene glycol was mixed uniformly with the above mixture.

After that, the resulting mixture was crushed until it passed through a JIS standard sieve having a mesh size of 710 μm (sizing step). This produced a comparative water-absorbing resin powder (2). Table 3 shows the CRC, the EMI, the water absorption time according to a vortex method, and the diffusion absorbency period of the comparative water-absorbing resin powder (2). Table 6 shows the results of measuring the elastic modulus of the comparative water-absorbing resin powder (2). The comparative water-absorbing resin powder (2) produced as above had an AAP 0.3 of 28.1 g/g.

Example 2

An operation similar to the operation of Comparative Example 2 above was carried out except that the screw was changed to screw No. S86-4610 (see Table 1 for the shape of the screw) and that the barrel was changed to barrel No. B88-178 (see Table 2 for the shape of the barrel). This produced water-absorbing resin particles (2) and a water-absorbing resin powder (2). The water-absorbing resin powder (2) had an internal gas bubble ratio of 1.9% and a surface tension of 72 mN/m. Table 3 shows the CRC, the EMI, the water absorption time according to a vortex method, and the diffusion absorbency period of the water-absorbing resin powder (2). Table 7 shows the results of measuring the elastic modulus of the water-absorbing resin powder (2).

Example 3

An operation similar to the operation of Comparative Example 1 above was carried out except that the amount of polyethyleneglycol diacrylate (average n number: 9) to be used was changed to 0.84 parts by weight. The operation produced hydrogel (3) in the shape of a belt and cut hydrogel (3).

Operations similar to those of Example 2 except that the die pore diameter of the porous plate for gel-crushing was changed to 8.0 mm were carried out on the cut hydrogel (3) produced through the above operation. This produced water-absorbing resin particles (3) and a water-absorbing resin powder (3). Table 3 shows the CRC, the EMI, the water absorption time according to a vortex method, and the diffusion absorbency period of the water-absorbing resin powder (3). Table 8 shows the results of measuring the elastic modulus of the water-absorbing resin powder (3). The water-absorbing resin powder (3) produced as above had an AAP 0.3 of 28.3 g/g.

Example 4

An operation similar to the operation of Comparative Example 1 above was carried out except that the amount of polyethyleneglycol diacrylate (average n number: 9) to be used was changed to 0.70 parts by weight. The operation produced hydrogel (4) in the shape of a belt and cut hydrogel (4).

Operations similar to those of Example 2 were carried out on the cut hydrogel (4) produced through the above operation. This produced water-absorbing resin particles (4) and a water-absorbing resin powder (4). Table 3 shows the CRC, the EMI, the water absorption time according to a vortex method, and the diffusion absorbency period of the water-absorbing resin powder (4). Table 9 shows the results of measuring the elastic modulus of the water-absorbing resin powder (4). The water-absorbing resin powder (4) produced as above had an AAP 0.3 of 32.0 g/g.

Comparative Example 5

A water-absorbing resin powder (particles ground to have uneven shapes) taken out from a disposable diaper (available from Kimberly-Clark Corp.; product name: HUGGIES; size: 4 Maxi) purchased in Turkey in April 2013 was used as a comparative water-absorbing resin powder (5). The comparative water-absorbing resin powder (5) had an internal gas bubble ratio of 3.8% and a surface tension of 63 mN/m. Table 3 shows the CRC, the EMI, the water absorption time according to a vortex method, and the diffusion absorbency period of the comparative water-absorbing resin powder (5). Table 12 shows the results of measuring the elastic modulus of the comparative water-absorbing resin powder (5).

TABLE 1

| Screw No. | Screw outer diameter [mm] | Screw shaft diameter [mm] | Screw flight thickness [mm] | Number of screw windings | Pitch length of single screw winding [mm] | Cross-sectional area B [mm$^2$] |
|---|---|---|---|---|---|---|
| S86-445 | 86 | 41 | 5 | 4 | 59.1 | 1433 |
| S86-4610 | 86 | 65 | 10 | 4 | 59.1 | 3423 |

TABLE 2

| Barrel No. | Barrel inner diameter N [mm] | Number of barrel spirals | Barrel ridge height YH [mm] | Barrel ridge width YF [mm] | Cross-sectional area A [mm$^2$] | Ratio YH/N of barrel ridge height to inner diameter | Ratio YF/N of barrel ridge width to inner diameter |
|---|---|---|---|---|---|---|---|
| B88-874 | 88 | 8 | 7 | 4 | 6082 | 0.080 | 0.045 |
| B88-178 | 88 | 1 | 7 | 8 | 6082 | 0.080 | 0.091 |

Comparative Example 3

A water-absorbing resin powder (particles ground to have uneven shapes) taken out from a disposable diaper (available from Procter & Gamble; product name: Pampers Easy Up Pants; size: 4 Maxi) purchased in Belgium in June 2013 was used as a comparative water-absorbing resin powder (3). Table 3 shows the CRC, the EMI, the water absorption time according to a vortex method, and the diffusion absorbency period of the comparative water-absorbing resin powder (3). Table 10 shows the results of measuring the elastic modulus of the comparative water-absorbing resin powder (3).

Comparative Example 4

A water-absorbing resin powder (spherical, granulated particles) taken out from a disposable diaper (available from Unicharm Corporation; product name: Mamy Poko Pants; size L) purchased in Indonesia in October 2011 was used as a comparative water-absorbing resin powder (4). The comparative water-absorbing resin powder (4) had an internal gas bubble ratio of 0.9% and a surface tension of 60 mN/m. Table 3 shows the CRC, the EMI, the water absorption time according to a vortex method, and the diffusion absorbency period of the comparative water-absorbing resin powder (4). Table 11 shows the results of measuring the elastic modulus of the comparative water-absorbing resin powder (4).

TABLE 3

| | | CRC [g/g] | EMI (600-500 μm) | Vortex [sec] | Diffusion absorbency period [sec] |
|---|---|---|---|---|---|
| Comparative Example 1 | Comparative water-absorbing resin powder (1) | 27.1 | 5213 | 32 | 105 |
| Example 1 | Water-absorbing resin powder (1) | 27.0 | 6793 | 32 | 86 |
| Comparative Example 2 | Comparative water-absorbing resin powder (2) | 27.6 | 5988 | 44 | 118 |
| Example 2 | Water-absorbing resin powder (2) | 27.0 | 7361 | 29 | 84 |
| Example 3 | Water-absorbing resin powder (3) | 28.5 | 6851 | 24 | 82 |
| Example 4 | Water-absorbing resin powder (4) | 30.2 | 5800 | 39 | 91 |
| Comparative Example 3 | Comparative water-absorbing resin powder (3) | 28.4 | 6037 | 74 | 146 |
| Comparative Example 4 | Comparative water-absorbing resin powder (4) | 32.8 | 4681 | 23 | 403 |
| Comparative Example 5 | Comparative water-absorbing resin powder (5) | 30.4 | 3878 | 25 | 151 |

TABLE 4

| | | Mesh size (H) of upper sieve for classification [μm] | Mesh size (I) of lower sieve for classification [μm] | CRCdw [g/g] | Elastic modulus G' [Pa] | EMI |
| --- | --- | --- | --- | --- | --- | --- |
| Comparative Example 1 | Comparative water-absorbing resin powder (1) | 710 | 600 | 181 | 6102 | 5972 |
| | | 600 | 500 | 175 | 6415 | 5213 |
| | | 500 | 425 | 160 | 7823 | 5188 |
| | | 425 | 300 | 150 | 9328 | 4746 |
| | | 300 | 150 | 124 | 12384 | 3670 |

TABLE 5

| | | Mesh size (H) of upper sieve for classification [μm] | Mesh size (I) of lower sieve for classification [μm] | CRCdw [g/g] | Elastic modulus G' [Pa] | EMI |
| --- | --- | --- | --- | --- | --- | --- |
| Example 1 | Water-absorbing resin powder (1) | 710 | 600 | 176 | 8126 | 7844 |
| | | 600 | 500 | 170 | 8472 | 6793 |
| | | 500 | 425 | 160 | 7823 | 5169 |
| | | 425 | 300 | 150 | 9328 | 4728 |
| | | 300 | 150 | 124 | 12384 | 3657 |

TABLE 6

| | | Mesh size (H) of upper sieve for classification [μm] | Mesh size (I) of lower sieve for classification [μm] | CRCdw [g/g] | Elastic modulus G' [Pa] | EMI |
| --- | --- | --- | --- | --- | --- | --- |
| Comparative Example 2 | Comparative water-absorbing resin powder (2) | 710 | 600 | 185 | 6951 | 6822 |
| | | 600 | 500 | 171 | 7450 | 5988 |
| | | 500 | 425 | 154 | 8651 | 5647 |
| | | 425 | 300 | 137 | 10325 | 5080 |
| | | 300 | 150 | 109 | 13125 | 3711 |

TABLE 7

| | | Mesh size (H) of upper sieve for classification [μm] | Mesh size (I) of lower sieve for classification [μm] | CRCdw [g/g] | Elastic modulus G' [Pa] | EMI |
| --- | --- | --- | --- | --- | --- | --- |
| Example 2 | Water-absorbing resin powder (2) | 710 | 600 | 183 | 7891 | 7722 |
| | | 600 | 500 | 171 | 9158 | 7361 |
| | | 500 | 425 | 153 | 10500 | 6837 |
| | | 425 | 300 | 135 | 12513 | 6124 |
| | | 300 | 150 | 104 | 15396 | 4287 |

TABLE 8

| | | Mesh size (H) of upper sieve for classification [μm] | Mesh size (I) of lower sieve for classification [μm] | CRCdw [g/g] | Elastic modulus G' [Pa] | EMI |
| --- | --- | --- | --- | --- | --- | --- |
| Example 3 | Water-absorbing resin powder (3) | 710 | 600 | 191 | 7021 | 7357 |
| | | 600 | 500 | 178 | 7972 | 6851 |
| | | 500 | 425 | 162 | 9101 | 6374 |
| | | 425 | 300 | 146 | 10684 | 5665 |
| | | 300 | 150 | 116 | 13689 | 4173 |

TABLE 9

|  | | Mesh size (H) of upper sieve for classification [μm] | Mesh size (I) of lower sieve for classification [μm] | CRCdw [g/g] | Elastic modulus G' [Pa] | EMI |
|---|---|---|---|---|---|---|
| Example 4 | Water-absorbing resin powder (4) | 710 | 600 | 241 | 4911 | 5892 |
|  |  | 600 | 500 | 238 | 5781 | 5800 |
|  |  | 500 | 425 | 224 | 6108 | 5050 |
|  |  | 425 | 300 | 196 | 7256 | 4497 |
|  |  | 300 | 150 | 152 | 9987 | 3530 |

TABLE 10

|  | | Mesh size (H) of upper sieve for classification [μm] | Mesh size (I) of lower sieve for classification [μm] | CRCdw [g/g] | Elastic modulus G' [Pa] | EMI |
|---|---|---|---|---|---|---|
| Comparative Example 3 | Comparative water-absorbing resin powder (3) | 710 | 600 | 186 | 6705 | 6934 |
|  |  | 600 | 500 | 176 | 7071 | 6037 |
|  |  | 500 | 425 | 167 | 8011 | 5643 |
|  |  | 425 | 300 | 157 | 8950 | 4843 |
|  |  | 300 | 150 | 130 | 12663 | 3999 |

TABLE 11

|  | | Mesh size (H) of upper sieve for classification [μm] | Mesh size (I) of lower sieve for classification [μm] | CRCdw [g/g] | Elastic modulus G' [Pa] | EMI |
|---|---|---|---|---|---|---|
| Comparative Example 4 | Comparative water-absorbing resin powder (4) | 710 | 600 | 330 | 3645 | 5277 |
|  |  | 600 | 500 | 326 | 3867 | 4681 |
|  |  | 500 | 425 | 319 | 3865 | 3906 |
|  |  | 425 | 300 | 312 | 3864 | 3038 |
|  |  | 300 | 150 | 301 | 4125 | 1988 |

TABLE 12

|  | | Mesh size (H) of upper sieve for classification [μm] | Mesh size (I) of lower sieve for classification [μm] | CRCdw [g/g] | Elastic modulus G' [Pa] | EMI |
|---|---|---|---|---|---|---|
| Comparative Example 5 | Comparative water-absorbing resin powder (5) | 710 | 600 | 324 | 3616 | 4822 |
|  |  | 600 | 500 | 343 | 3401 | 3878 |
|  |  | 500 | 425 | 344 | 3546 | 3405 |
|  |  | 425 | 300 | 346 | 3691 | 2782 |
|  |  | 300 | 150 | 316 | 4507 | 2046 |

Figure 13:
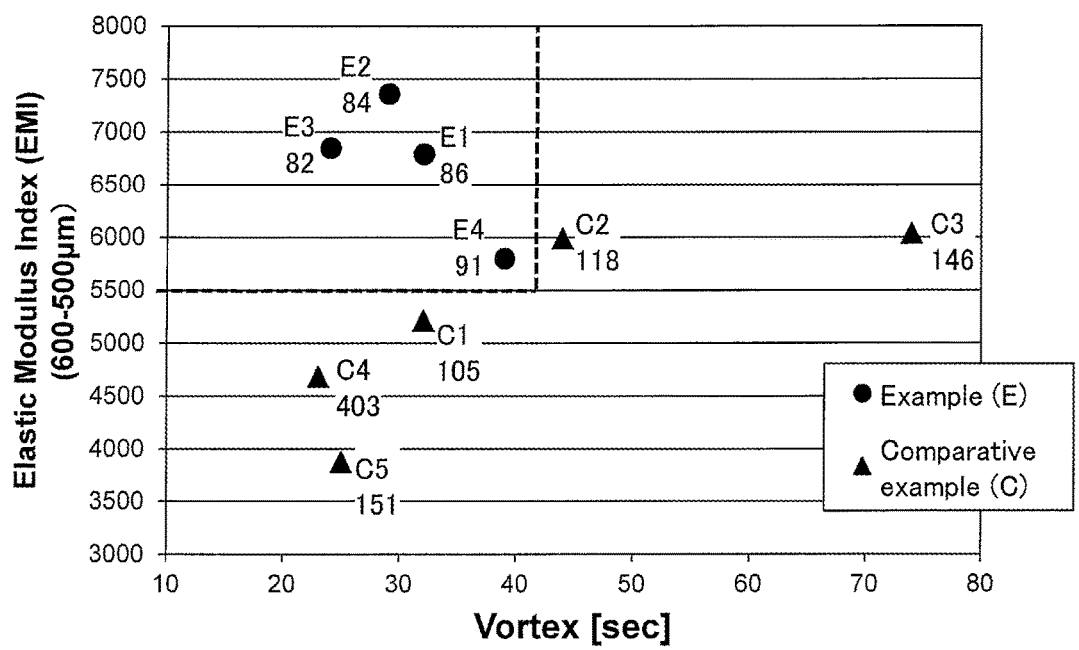
FIG. 13 is a graph that plots respective diffusion absorbency periods of water-absorbing resin powders (1) to (4)

FIG. 13 is a graph that plots the respective diffusion absorbency periods listed in Table 3 of the water-absorbing resin powders (1) to (4) produced in the Examples and the comparative water-absorbing resin powders (1) to (5) produced in the Comparative Examples. The horizontal axis indicates the water absorption time according to a vortex method (unit: seconds), whereas the vertical axis indicates the elastic modulus index (EMI). The EMI value was calculated with use of a water-absorbing resin powder having particle diameters of 600 μm to 500 μm that was obtained through a sieving operation involving use of a JIS standard sieve having a mesh size of 600 μm at the upper stage and a JIS standard sieve having a mesh size of 500 μm at the lower stage in the step 1 described above.

The values shown in FIG. 13 each indicate a diffusion absorbency period (unit: seconds), and correspond to the values listed in Table 3. FIG. 13 shows solid circles to indicate the results of the Examples and solid triangles to indicate the results of the Comparative Examples. For example, the symbol "E1" indicates the result of Example 1, and the symbol "C1" indicates the result of Comparative Example 1.

The water-absorbing resin powders (1) to (4) were each arranged such that a proportion of the water-absorbing resin powder that had particle sizes of not less than 150 μm to less than 850 μm was not less than 90 weight %. FIG. 13 also indicates that the water-absorbing resin powders (1) to (4), in each of which the water absorption time according to a vortex method was not more than 42 seconds and the elastic modulus index of a water-absorbing resin powder having particle sizes of not less than 500 μm and less than 600 μm was not less than 5500, each exhibited an excellent diffusion absorbency period of less than 100 seconds.

The water-absorbing resin powder (1) produced in Example 1 was produced by, as described above, removing flake-shaped particles from the comparative water-absorbing resin powder (1) with use of a ton-cap metal gauze having rectangular mesh openings and mixing the resulting particles with particles having particle sizes of not more than 500 μm.

The comparative water-absorbing resin powder (1) contained 16% flake-shaped particles as described for Comparative Example 1. The water-absorbing resin powder (1), from which the above flake-shaped particles had been removed with use of a ton-cap metal gauze, contained particles each having a shape so adjusted as to be close to a sphere. The water-absorbing resin powder (1), as a result, presumably exhibited an EMI value higher than that of the comparative water-absorbing resin powder (1), a shorter water absorption time (that is, more excellent water absorption speed), and an excellent diffusion absorbency period of 86 seconds.

The water-absorbing resin powders (2) to (4) were produced by gel-crushing involving use of a gel-crushing device (A) including the same screw and barrel, and were produced with use of a screw and barrel having conditions different from those for Comparative Example 2.

Carrying out gel-crushing with use of the above gel-crushing device (A), which included a screw and barrel having suitable conditions, presumably allowed for production of particles each having a shape close to a sphere, thereby making it possible to produce a water-absorbing resin powder having an excellent diffusion absorbency period. With regard to the water absorption time alone, the comparative water-absorbing resin powders (1), (4), and (5) may exhibit a more excellent value than that for a water-absorbing resin powder produced in an Example; however, the comparative water-absorbing resin powders each had an EMI of less than 5500.

FIG. 13 proves that a water-absorbing resin powder arranged such that the proportion of the water-absorbing resin powder that has particle sizes of not less than 150 μm to less than 850 μm is not less than 90 weight %, the water absorption time is not more than 42 seconds, and the elastic modulus index of a water-absorbing resin powder having particle sizes of not less than 500 μm and less than 600 μm is not less than 5500 exhibits an excellent diffusion absorbency period of less than 100 seconds.

Tables 4 to 12 prove that the elastic modulus index of a water-absorbing resin powder having particle sizes of not less than 425 μm and less than 500 μm is preferably not less than 4500 and that the elastic modulus index of a water-absorbing resin powder having particle sizes of not less than 300 μm and less than 425 μm is further preferably not less than 3500.

Table 3 proves that any water-absorbing resin powder arranged such that the proportion of the water-absorbing resin powder that has particle sizes of not less than 150 μm to less than 850 μm is not less than 90 weight %, the water absorption time is not more than 42 seconds, and the elastic modulus index of a water-absorbing resin powder having particle sizes of not less than 500 μm and less than 600 μm is not less than 5500 has a diffusion absorbency period of less than 100 seconds, indicating a particularly excellent diffusion absorbency property.

On the other hand, as in Comparative Examples 1 to 5, any water-absorbing resin powder that meets only the requirements (1) and (2) above or only the requirements (1) and (3) above has a diffusion absorbency period of more than 100 seconds, failing to exhibit a satisfactory diffusion absorbency property.

INDUSTRIAL APPLICABILITY

A water-absorbing resin powder in accordance with the present invention and water absorbent resin powder produced by a production method in accordance with the present invention are useful in a sanitary article such as a disposable diaper, a sanitary napkin, and a blood absorbent for medical use. Further, the water-absorbing resin powder can also be variously used for a pet urine absorbent, a urine gelatinizer of a portable toilet, an agent for preserving freshness of vegetables, fruit, and the like, a drip absorbent for meat and fish, a refrigerant, a disposable body warmer, a battery gelatinizer, a water retention agent for plants, soil, and the like, a condensation preventing agent, a waterproofing agent, a packing agent, artificial snow, and the like.

REFERENCE SIGNS LIST

40 Dish (container section)
41 Swollen gel
42 Parallel plate (plate-shaped member)
43 Rotary shaft
300 Rheometer
30 Tray
31 Dispersion region
32 Water-absorbing resin powder
33 Top sheet
34 Metal gauze
35 Inlet
36 Lid
37 Weight
200 Diffusion absorbency period measuring device
11 Screw
12 Porous plate
13 Barrel
14 Feed opening
15 Hopper
16 Extrusion opening
17 Rotary blade
18 Ring
19 Return preventing member
20 Base
21 Motor
22 Rotating shaft
23 Flight section
100 Gel-crushing device

The invention claimed is:
1. Water absorbent resin powder comprising:
a polyacrylic acid (salt)-based water-absorbing resin as a main component,
said water absorbent resin powder being surface-cross-linked and satisfying (1) to (3) below:

(1) a proportion of the water absorbent resin powder having a particle size of not less than 150 μm and less than 850 μm is not less than 90 weight %;
(2) a water absorption time according to a vortex method is not more than 42 seconds; and
(3) an elastic modulus index (600-500) is not less than 5500.

2. The water-absorbing resin powder according to claim 1, further satisfying (4) below:
(4) an elastic modulus index (500-425) is not less than 4500.

3. The water-absorbing resin powder according to claim 2, further satisfying (5) below:
(5) an elastic modulus index (425-300) is not less than 3500.

4. The water-absorbing resin powder according to claim 1, wherein,
(a) a proportion of the water-absorbing resin powder having a particle size of not less than 150 μm and less than 300 μm is 5 weight % to 50 weight %;
(b) a proportion of the water-absorbing resin powder having a particle size of not less than 300 μm and less than 425 μm is 10 weight % to 60 weight %;
(c) a proportion of the water-absorbing resin powder having a particle size of not less than 425 μm and less than 500 μm is 5 weight % to 50 weight %;
(d) a proportion of the water-absorbing resin powder having a particle size of not less than 500 μm and less than 600 μm is 5 weight % to 50 weight %; and
(e) a proportion of the water-absorbing resin powder having a particle size of not less than 600 μm and less than 850 μm is 0.1 weight % to 50 weight %, and
wherein a total proportion of the water-absorbing resin powder having particle sizes, each of which is defined in (a) to (e) above, is 90 weight % to 100 weight %.

5. The water-absorbing resin powder according to claim 1, wherein the water-absorbing resin powder has an internal gas bubble ratio of 0% to 3.7%.

6. The water-absorbing resin powder according to claim 1, wherein the water-absorbing resin powder has a surface tension of not less than 69 mN/m.

7. The water-absorbing resin powder according to claim 1, wherein the water-absorbing resin powder has CRC as defined in ERT 441.2-02 of 25 g/g to 50 g/g.

8. The water-absorbing resin powder according to claim 1, wherein the water-absorbing resin powder has a weight average particle diameter (D50) of 300 μm to 500 μm and a logarithmic standard deviation (σζ) of 0.25 to 0.45.

9. An absorbent body including the water-absorbing resin powder according to claim 1.

10. An absorbent article including the water-absorbing resin powder according to claim 1.

* * * * *